(12) United States Patent
Ciblat et al.

(10) Patent No.: US 10,865,206 B2
(45) Date of Patent: *Dec. 15, 2020

(54) INHIBITORS OF CYCLIN-DEPENDENT KINASE 7 (CDK7)

(71) Applicant: Syros Pharmaceuticals, Inc., Cambridge, MA (US)

(72) Inventors: Stephane Ciblat, Montreal (CA); Anzhelika Kabro, Montreal (CA); Melissa Leblanc, Laval (CA); Serge Leger, Notre-Dame-de-l'ile-Perrot (CA); Jason J. Marineau, Franklin, MA (US); Tom Miller, Wakefield, MA (US); Stephanie Roy, Lachine (CA); Darby Schmidt, Arlington, MA (US); M. Arshad Siddiqui, Newton, MA (US); Kevin Sprott, Needham, MA (US); Dana K. Winter, Rigaud (CA); Amy Ripka, Reading, MA (US); Dansu Li, Warrington, PA (US); Guoli Zhang, Tianjin (CN)

(73) Assignee: Syros Pharmaceuticals, Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/412,726

(22) Filed: May 15, 2019

(65) Prior Publication Data

US 2019/0337940 A1 Nov. 7, 2019

Related U.S. Application Data

(63) Continuation of application No. 15/519,484, filed as application No. PCT/CN2015/091996 on Oct. 15, 2015, now Pat. No. 10,308,648.

(60) Provisional application No. 62/064,737, filed on Oct. 16, 2014.

(51) Int. Cl.
*C07D 471/04* (2006.01)
*C07D 401/14* (2006.01)
*C07D 401/04* (2006.01)
*C07D 403/04* (2006.01)

(52) U.S. Cl.
CPC ......... *C07D 471/04* (2013.01); *C07D 401/04* (2013.01); *C07D 401/14* (2013.01); *C07D 403/04* (2013.01)

(58) Field of Classification Search
CPC .. C07D 471/04; C07D 401/04; C07D 401/14; C07D 403/04
See application file for complete search history.

(56) References Cited

U.S. PATENT DOCUMENTS

| | | | |
|---|---|---|---|
| 8,212,032 B2 | 7/2012 | Ding et al. | |
| 8,435,980 B2 | 5/2013 | Florjancic et al. | |
| 8,629,156 B2 | 1/2014 | Devasagayaraj et al. | |
| 8,912,180 B2 | 12/2014 | Takahashi et al. | |
| 8,993,600 B2 | 3/2015 | Hadida Ruah et al. | |
| 10,308,648 B2* | 6/2019 | Ciblat .................. | C07D 401/04 |
| 2006/0040986 A1 | 2/2006 | Imagawa et al. | |
| 2008/0045568 A1* | 2/2008 | Deng .................. | C07D 215/48 514/312 |
| 2008/0286204 A1 | 11/2008 | Hadida-Ruah et al. | |
| 2010/0249149 A1 | 9/2010 | Allgeier et al. | |
| 2012/0165309 A1 | 6/2012 | Takahashi et al. | |

(Continued)

FOREIGN PATENT DOCUMENTS

WO 0064880 A1 11/2000
WO 2005095357 A2 10/2005

(Continued)

OTHER PUBLICATIONS

C. Bruyère et al., 25 Current Opinion in Cell Biology, 772-779 (2013) (Year: 2013).*
V. Kryštof et al., 46 European Journal of Medicinal Chemistry (2011) (Year: 2011).*
C. Hutterer et al., 4 Antimicrobial Agents and Chemotherapy (2015) (Year: 2015).*
A. Leitch et al., 158 British Journal of Pharmacology, 1004-1016 (2009) (Year: 2009).*

(Continued)

*Primary Examiner* — Mark L Shibuya
*Assistant Examiner* — Ebenezer O Sackey
(74) *Attorney, Agent, or Firm* — Goodwin Procter LLP

(57) ABSTRACT

The present invention provides novel compounds of Formula (I) and pharmaceutically acceptable salts, solvates, hydrates, tautomers, stereoisomers, isotopically labeled derivatives, and compositions thereof. Also provided are methods and kits involving the compounds or compositions for treating or preventing proliferative diseases (e.g., cancers (e.g., leukemia, melanoma, multiple myeloma), benign neoplasms, angiogenesis, inflammatory diseases, autoinflammatory diseases, and autoimmune diseases) in a subject. Treatment of a subject with a proliferative disease using a compound or composition of the invention may inhibit the aberrant activity of cyclin-dependent kinase (e.g., CDK7), and therefore induce cellular apoptosis and/or inhibit transcription in the subject.

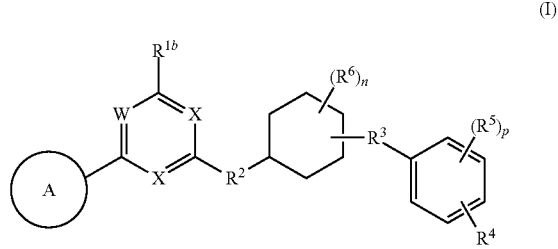

25 Claims, 5 Drawing Sheets

(56) References Cited

U.S. PATENT DOCUMENTS

| | | | | |
|---|---|---|---|---|
| 2016/0264551 A1* | 9/2016 | Ciblat | ................ | C07D 401/14 |
| 2016/0264552 A1* | 9/2016 | Ciblat | ................ | C07D 401/14 |
| 2016/0264554 A1* | 9/2016 | Gray | ................ | C07D 401/04 |
| 2017/0183355 A1* | 6/2017 | Sprott | ................ | C07D 401/14 |
| 2017/0327496 A1* | 11/2017 | Ciblat | ................ | C07D 401/04 |
| 2019/0292167 A1* | 9/2019 | Ciblat | ................ | A61K 31/506 |

FOREIGN PATENT DOCUMENTS

| | | | | |
|---|---|---|---|---|
| WO | 2007056341 A1 | 5/2007 | | |
| WO | WO-2007056341 A1 * | 5/2007 | .......... | C07D 405/12 |
| WO | 2007089768 A2 | 8/2007 | | |
| WO | 2007129195 A2 | 11/2007 | | |
| WO | 2011008915 A1 | 1/2011 | | |
| WO | WO-2011008915 A1 * | 1/2011 | .......... | C07D 471/04 |
| WO | 2015058140 A1 | 4/2015 | | |
| WO | WO-2015058140 A1 * | 4/2015 | | |

OTHER PUBLICATIONS

C. Sánchez-Martínez et al., 25 Bioorganic and Medicinal Chemistry Letters, 3420-3435 (2015) (Year: 2015).*
C. Cain, SciBX: Science-Business eXchange C (2014) (Year: 2014).*
C. Prevel et al., 88 European Journal of Medicinal Chemistry, 74-88 (2014) (Year: 2014).*
A. Abate et al., Expert Opinion on Investigational Drugs (2013) (Year: 2013).*
CAS Abstract and Indexed Compounds WO 2015/058140 (2015).

* cited by examiner

*FIG. 1A*

| Compound No. | Structure |
|---|---|
| 100 | 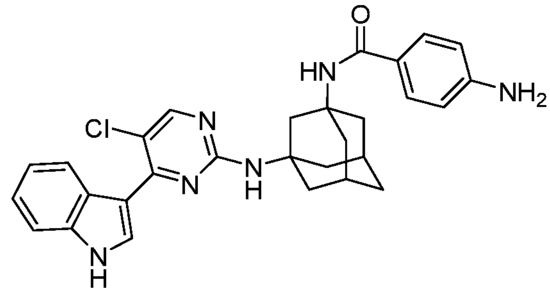 |
| 101 | 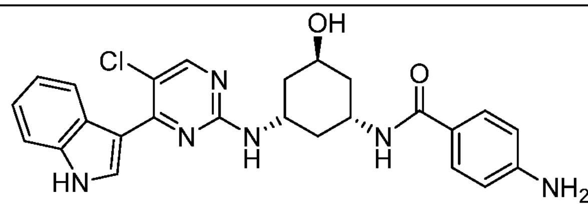 |
| 102 | 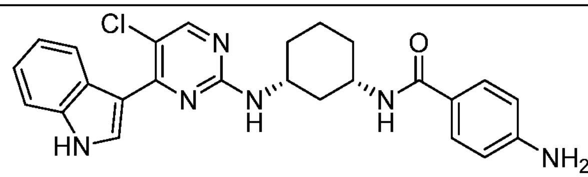 |
| 103 | 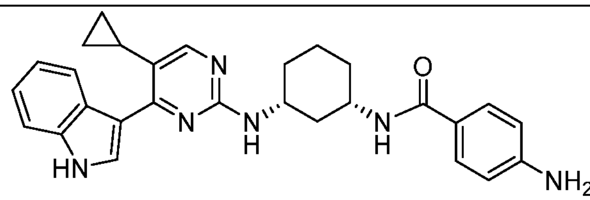 |
| 104 | 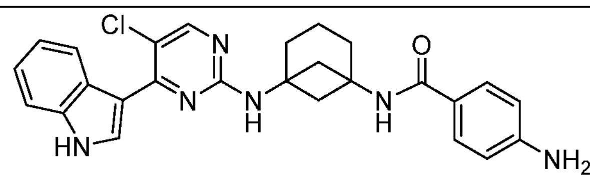 |
| 105 | 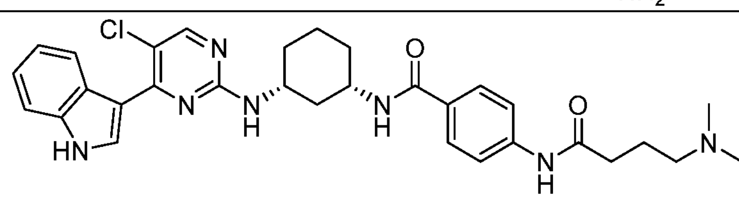 |
| 106 | 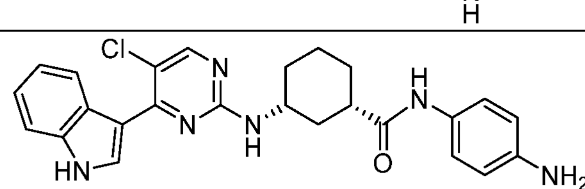 |
| 107 | 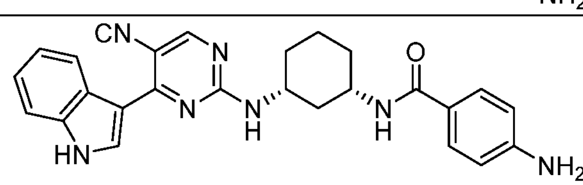 |

*FIG. 1B*

| Compound No. | Structure |
|---|---|
| 108 | 5-chloro-4-(pyridin-3-yl)pyrimidin-2-yl linked via NH to cyclohexane-1,3-diyl linked via NH-C(=O) to 4-aminobenzamide |
| 109 | 5-chloro-4-(1H-indol-3-yl)pyrimidin-2-yl linked via NH to cyclohexane-1,3-diyl linked via NH-SO₂ to 4-aminobenzenesulfonamide |
| 110-1 | 5-chloro-4-(1H-indol-3-yl)pyrimidin-2-yl linked via NH to 5-fluorocyclohexane-1,3-diyl linked via NH-C(=O) to 4-aminobenzamide |
| 110-2 | 5-chloro-4-(1H-indol-3-yl)pyrimidin-2-yl linked via NH to 5-fluorocyclohexane-1,3-diyl (alternate stereochem) linked via NH-C(=O) to 4-aminobenzamide |
| 111 | 5-chloro-4-(1H-indol-3-yl)pyrimidin-2-yl linked via NH to cyclohexane-1,3-diyl linked via NH-C(=O) to 4-amino-3-fluorobenzamide |
| 112 | 5-chloro-4-(1H-indol-3-yl)pyrimidin-2-yl linked via NH to cyclohexane-1,3-diyl linked via NH-C(=O) to 4-amino-2-fluorobenzamide |
| 113 | 5-chloro-4-(1H-indol-3-yl)pyrimidin-2-yl linked via NH to cyclohexane-1,3-diyl linked via NH-C(=O) to 4-(2-amino-2-oxoacetamido)benzamide |
| 114 | 4-(1H-indol-3-yl)pyrimidin-2-yl linked via NH to cyclohexane-1,3-diyl linked via NH-C(=O) to 4-aminobenzamide |

*FIG. 1C*

| Compound No. | Structure |
|---|---|
| 115-1 | 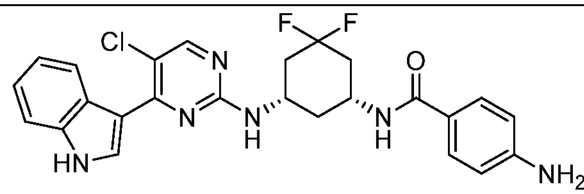 |
| 115-2 | 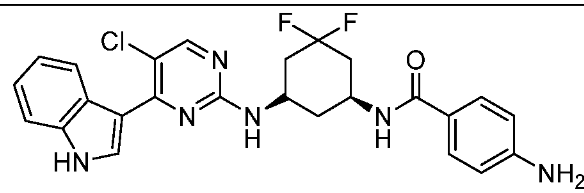 |
| 116 | 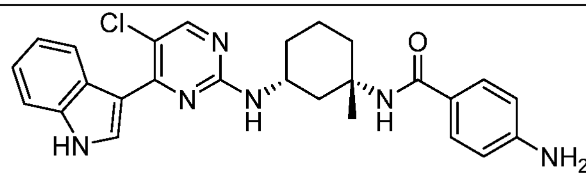 |
| 117 | 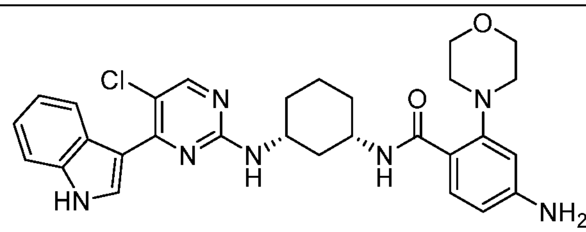 |
| 118 | 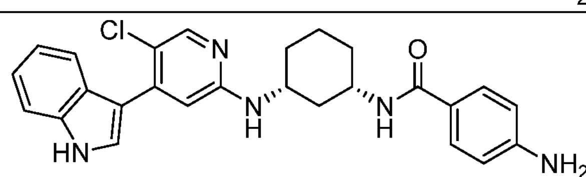 |
| 119 | 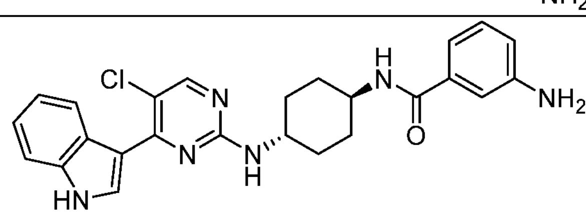 |
| 120 | 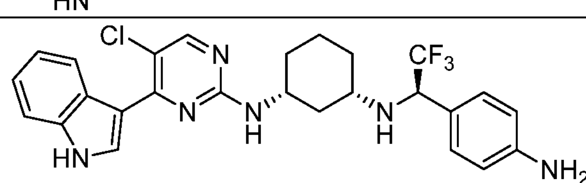 |
| 121 | 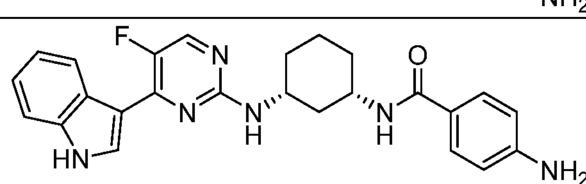 |

FIG. 1D

| Compound No. | Structure |
|---|---|
| 122 | 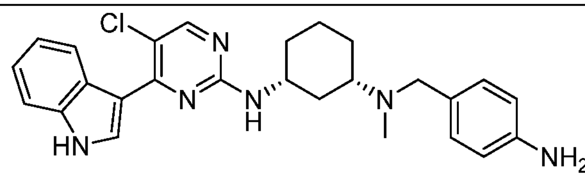 |
| 123 | 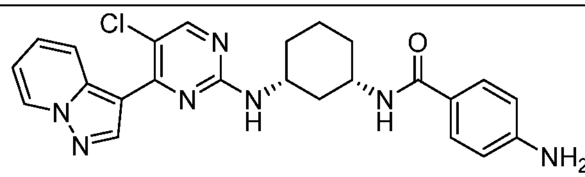 |
| 124 | 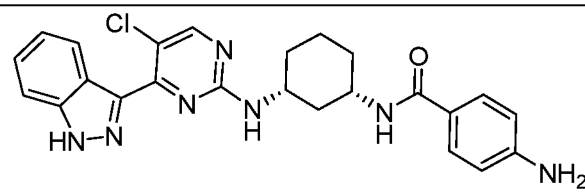 |
| 125 | 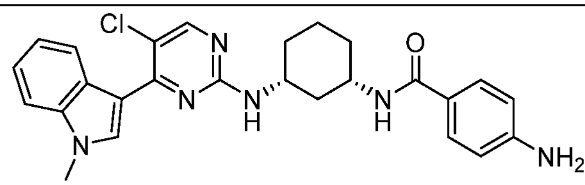 |
| 126 | 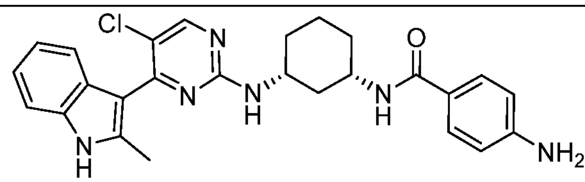 |
| 127 | 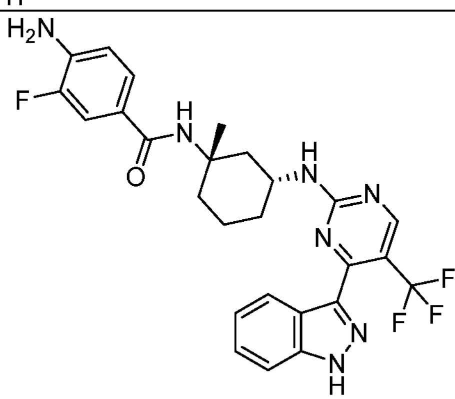 |
| 128 | 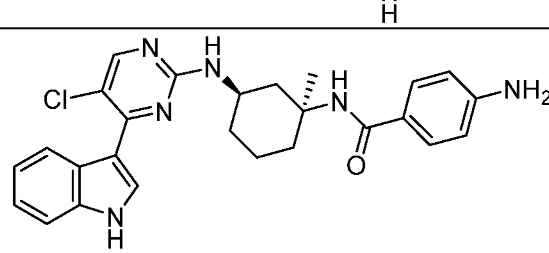 |

| Compound No. | Structure |
|---|---|
| 129 | 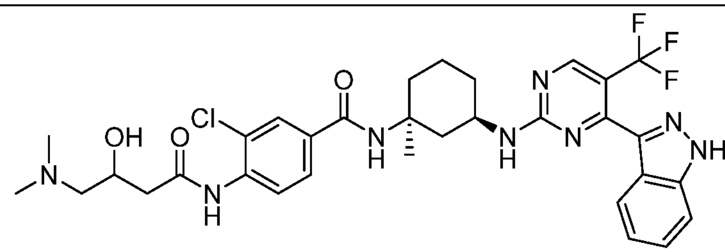 |
| 130 | 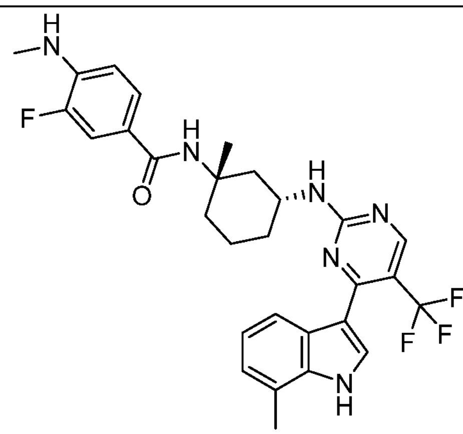 |

INHIBITORS OF CYCLIN-DEPENDENT KINASE 7 (CDK7)

CROSS REFERENCE TO RELATED APPLICATIONS

This application is a continuation of U.S. patent application Ser. No. 15/519,484, filed Apr. 14, 2017, which is a U.S. National Stage Application filed under 35 U.S.C. § 371 of International Patent Application No. PCT/CN2015/091996, filed Oct. 15, 2015, which claims the benefit of and priority to U.S. Provisional Patent Application No. 62/064,737, filed Oct. 16, 2014, the contents of each of which are hereby incorporated by reference in their entirety.

BACKGROUND OF THE INVENTION

The members of the cyclin-dependent kinase (CDK) family play critical regulatory roles in proliferation. Unique among the mammalian CDKs, CDK7 has consolidated kinase activities, regulating both the cell cycle and transcription. In the cytosol, CDK7 exists as a heterotrimeric complex and is believed to function as a CDK1/2-activating kinase (CAK), whereby phosphorylation of conserved residues in CDK1/2 by CDK7 is required for full catalytic CDK activity and cell cycle progression. In the nucleus, CDK7 forms the kinase core of the RNA polymerase (RNAP) II general transcription factor complex and is charged with phosphorylating the C-terminal domain (CTD) of RNAP II, a requisite step in gene transcriptional initiation. Together, the two functions of CDK7, i.e., CAK and CTD phosphorylation, support critical facets of cellular proliferation, cell cycling, and transcription.

Disruption of RNAP II CTD phosphorylation has been shown to preferentially affect proteins with short half-lives, including those of the anti-apoptotic BCL-2 family. Cancer cells have demonstrated ability to circumvent pro-cell death signaling through upregulation of BCL-2 family members. Therefore, inhibition of human CDK7 kinase activity is likely to result in anti-proliferative activity.

The discovery of selective inhibitors of CDK7 has been hampered by the high sequence and structural similarities of the kinase domain of CDK family members. Therefore, there is a need for the discovery and development of selective CDK7 inhibitors. Such CKD7 inhibitors hold promise as a therapeutic agent for the treatment of CLL and other cancers.

BRIEF DESCRIPTION OF THE DRAWINGS

FIGS. 1A-1E are a table of exemplary compounds of Formula I.

SUMMARY OF THE INVENTION

Figure 1E:
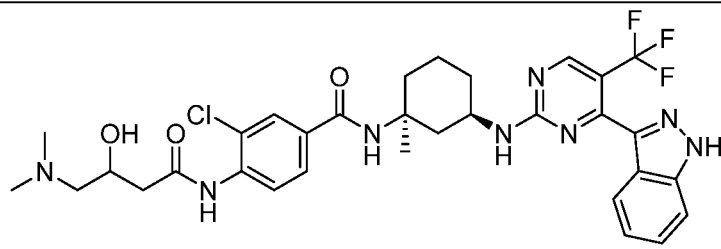
Figure 1E:
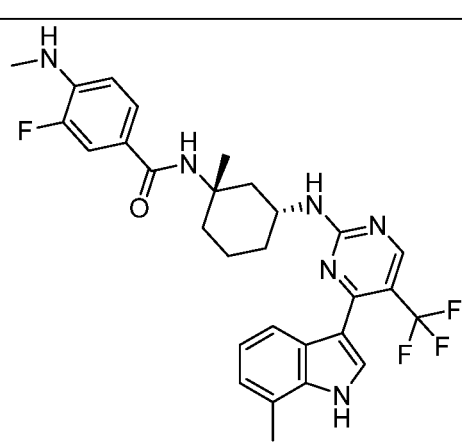

The present invention provides CDK inhibitors, more particularly CDK7, CDK12 and CDK13 inhibitors, and in particular selective CDK7 inhibitors of Formula (I), and pharmaceutically acceptable salts, solvates, hydrates, tautomers, stereoisomers, isotopically labeled derivatives, and compositions thereof. The present invention further provides methods of using the compounds of the invention, and pharmaceutically acceptable salts, solvates, hydrates, tautomers, stereoisomers, isotopically labeled derivatives, and compositions thereof, to study the inhibition of CDK7 and other CDK family members, and as therapeutics for the prevention and/or treatment of diseases associated with overexpression and/or aberrant activity of CDK7 and other CDK family members. In certain embodiments, the inventive compounds are used for the prevention and/or treatment of proliferative diseases (e.g., cancers (e.g., leukemia, melanoma, multiple myeloma), benign neoplasms, angiogenesis, inflammatory diseases, autoinflammatory diseases, and autoimmune diseases) in a subject.

In one aspect, the present invention provides compounds of Formula (I):

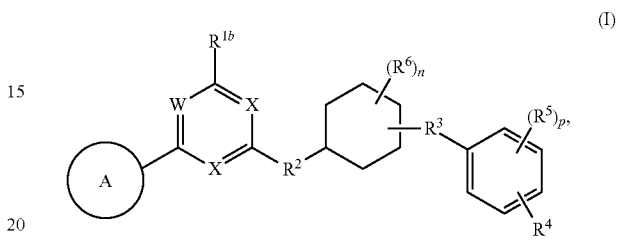

and pharmaceutically acceptable salts, solvates, hydrates, tautomers, stereoisomers, and isotopically labeled derivatives thereof, wherein Ring A, W, X, $R^{1b}$, $R^2$, $R^3$, $R^4$, $R^5$, $R^6$, n, p, and subvariables thereof are as defined herein.

In another aspect, the present invention provides pharmaceutical compositions comprising a compound of Formula (I), or a pharmaceutically acceptable salt, solvate, hydrate, tautomer, stereoisomer, or isotopically labeled derivative thereof, and optionally a pharmaceutically acceptable excipient. In certain embodiments, the pharmaceutical compositions described herein include a therapeutically effective amount of a compound of Formula (I), or a pharmaceutically acceptable salt, solvate, hydrate, tautomer, stereoisomer, or isotopically labeled derivative thereof. The pharmaceutical composition may be useful for treating and/or preventing a proliferative or infectious disease.

In another aspect, the present invention provides methods for treating and/or preventing proliferative diseases. Exemplary proliferative diseases include cancer (e.g., leukemia, melanoma, multiple myeloma), benign neoplasm, angiogenesis, inflammatory diseases, autoinflammatory diseases, and autoimmune diseases. In other embodiments, the present invention provides methods for treating and/or preventing an infectious disease (e.g., a viral infection).

In still another aspect, the present invention provides methods of down-regulating the expression of CDK7 in a biological sample or subject.

Another aspect of the invention relates to methods of inhibiting the activity of CDK7 in a biological sample or subject.

The present invention also provides methods of inhibiting cell growth in a biological sample or subject.

In still another aspect, the present invention provides methods of inducing apoptosis of a cell in a biological sample or a subject.

In yet another aspect, the present invention provides compounds of Formula (I), and pharmaceutically acceptable salts, solvates, hydrates, tautomers, stereoisomers, isotopically labeled derivatives, and compositions thereof, for use in the treatment of a proliferative disease in a subject.

In yet another aspect, the present invention provides compounds of Formula (I), and pharmaceutically acceptable salts, solvates, hydrates, tautomers, stereoisomers, isotopically labeled derivatives, and compositions thereof, for use in the treatment or prevention of an infectious disease in a subject. In certain embodiments, the infectious disease is a viral infection.

Another aspect of the present invention relates to kits comprising a container with a compound of Formula (I), or a pharmaceutically acceptable salt, solvate, hydrate, tautomer, stereoisomer, or isotopically labeled derivative thereof, or a pharmaceutical composition thereof. In certain embodiments, the kits described herein further include instructions for administering the compound of Formula (I), or the pharmaceutically acceptable salt, solvate, hydrate, tautomer, stereoisomer, or isotopically labeled derivative thereof, or the pharmaceutical composition thereof.

In still another aspect, the present invention provides methods of inhibiting other CDK family members, specifically CDK12 and/or CDK13, with a compound of Formula (I).

The details of one or more embodiments of the invention are set forth herein. Other features, objects, and advantages of the invention will be apparent from the Detailed Description, the FIGURES, the Examples, and the Claims.

Definitions

Definitions of specific functional groups and chemical terms are described in more detail below. The chemical elements are identified in accordance with the Periodic Table of the Elements, CAS version, *Handbook of Chemistry and Physics,* 75$^{th}$ Ed., inside cover, and specific functional groups are generally defined as described therein. Additionally, general principles of organic chemistry, as well as specific functional moieties and reactivity, are described in Thomas Sorrell, *Organic Chemistry,* University Science Books, Sausalito, 1999; Smith and March, *March's Advanced Organic Chemistry,* 5$^{th}$ Edition, John Wiley & Sons, Inc., New York, 2001; Larock, *Comprehensive Organic Transformations,* VCH Publishers, Inc., New York, 1989; and Carruthers, *Some Modern Methods of Organic Synthesis,* 3$^{rd}$ Edition, Cambridge University Press, Cambridge, 1987.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}$C- or $^{14}$C-enriched carbon are within the scope of this invention. Such compounds are useful, for example, as analytical tools, as probes in biological assays, or as therapeutic agents in accordance with the present invention.

Where a particular enantiomer is preferred, it may, in some embodiments be provided substantially free of the corresponding enantiomer, and may also be referred to as "optically enriched." "Optically-enriched," as used herein, means that the compound is made up of a significantly greater proportion of one enantiomer. In certain embodiments the compound is made up of at least about 90% by weight of a preferred enantiomer. In other embodiments the compound is made up of at least about 95%, 98%, or 99% by weight of a preferred enantiomer. Preferred enantiomers may be isolated from racemic mixtures by any method known to those skilled in the art, including chiral high pressure liquid chromatography (HPLC) and the formation and crystallization of chiral salts or prepared by asymmetric syntheses. See, for example, Jacques et al., *Enantiomers, Racemates and Resolutions* (Wiley Interscience, New York, 1981); Wilen, et al., *Tetrahedron* 33:2725 (1977); Eliel, E. L. *Stereochemistry of Carbon Compounds* (McGraw-Hill, N Y, 1962); Wilen, S. H. *Tables of Resolving Agents and Optical Resolutions* p. 268 (E. L. Eliel, Ed., Univ. of Notre Dame Press, Notre Dame, Ind. 1972).

The term "aliphatic" or "aliphatic group", as used herein, denotes a hydrocarbon moiety that may be straight-chain (i.e., unbranched), branched, or cyclic (including fused, bridging, and spiro-fused polycyclic) and may be completely saturated or may contain one or more units of unsaturation, but which is not aromatic. Unless otherwise specified, aliphatic groups contain 1-6 carbon atoms. In some embodiments, aliphatic groups contain 1-4 carbon atoms, and in yet other embodiments aliphatic groups contain 1-3 carbon atoms. Suitable aliphatic groups include, but are not limited to, linear or branched, alkyl, alkenyl, and alkynyl groups, and hybrids thereof such as (cycloalkyl)alkyl, (cycloalkenyl)alkyl or (cycloalkyl)alkenyl.

The term "alkyl," as used herein, refers to a monovalent saturated, straight- or branched-chain hydrocarbon such as a straight or branched group of 1-12, 1-10, or 1-6 carbon atoms, referred to herein as $C_1$-$C_{12}$ alkyl, $C_1$-$C_{10}$ alkyl, and $C_1$-$C_6$ alkyl, respectively. Examples of alkyl groups include, but are not limited to, methyl, ethyl, n-propyl, isopropyl, n-butyl, iso-butyl, sec-butyl, sec-pentyl, iso-pentyl, tert-butyl, n-pentyl, neopentyl, n-hexyl, sec-hexyl, and the like.

The terms "alkenyl" and "alkynyl" are art-recognized and refer to unsaturated aliphatic groups analogous in length and possible substitution to the alkyls described above, but that contain at least one double or triple bond, respectively. Exemplary alkenyl groups include, but are not limited to, —CH=CH$_2$ and —CH$_2$CH=CH$_2$.

The term "alkylene" refers to the diradical of an alkyl group.

The terms "alkenylene" and "alkynylene" refer to the diradicals of an alkenyl and an alkynyl group, respectively.

The term "methylene unit" refers to a divalent —CH$_2$— group present in an alkyl, alkenyl, alkynyl, alkylene, alkenylene, or alkynylene moiety.

The term "carbocyclic ring system", as used herein, means a monocyclic, or fused, spiro-fused, and/or bridged bicyclic or polycyclic hydrocarbon ring system, wherein each ring is either completely saturated or contains one or more units of unsaturation, but where no ring is aromatic.

The term "carbocyclyl" refers to a radical of a carbocyclic ring system. Representative carbocyclyl groups include cycloalkyl groups (e.g., cyclopentyl, cyclobutyl, cyclopentyl, cyclohexyl and the like), and cycloalkenyl groups (e.g., cyclopentenyl, cyclohexenyl, cyclopentadienyl, and the like).

The term "aromatic ring system" is art-recognized and refers to a monocyclic, bicyclic or polycyclic hydrocarbon ring system, wherein at least one ring is aromatic.

The term "aryl" refers to a radical of an aromatic ring system. Representative aryl groups include fully aromatic ring systems, such as phenyl, naphthyl, and anthracenyl, and ring systems where an aromatic carbon ring is fused to one or more non-aromatic carbon rings, such as indanyl, phthalimidyl, naphthimidyl, or tetrahydronaphthyl, and the like.

The term "heteroaromatic ring system" is art-recognized and refers to monocyclic, bicyclic or polycyclic ring system wherein at least one ring is both aromatic and comprises a heteroatom; and wherein no other rings are heterocyclyl (as defined below). In certain instances, a ring which is aromatic and comprises a heteroatom contains 1, 2, 3, or 4 independently selected ring heteroatoms in such ring.

The term "heteroaryl" refers to a radical of a heteroaromatic ring system. Representative heteroaryl groups include ring systems where (I) each ring comprises a heteroatom and is aromatic, e.g., imidazolyl, oxazolyl, thiazolyl, triazolyl, pyrrolyl, furanyl, thiophenyl pyrazolyl, pyridinyl, pyrazinyl, pyridazinyl, pyrimidinyl, indolizinyl, purinyl, naphthyridinyl, and pteridinyl; (ii) each ring is aromatic or carbocyclyl, at least one aromatic ring comprises a heteroatom and at least one other ring is a hydrocarbon ring or e.g., indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, carbazolyl, acridinyl, phenazinyl, phenothiazinyl, phenoxazinyl, pyrido[2,3-b]-1,4-oxazin-3(4H)-one, 5,6,7,8-tetrahydroquinolinyl and 5,6,7,8-tetrahydroisoquinolinyl; and (iii) each ring is aromatic or carbocyclyl, and at least one aromatic ring shares a bridgehead heteroatom with another aromatic ring, e.g., 4H-quinolizinyl. In certain embodiments, the heteroaryl is a monocyclic or bicyclic ring, wherein each of said rings contains 5 or 6 ring atoms where 1, 2, 3, or 4 of said ring atoms are a heteroatom independently selected from N, O, and S.

The term "heterocyclic ring system" refers to monocyclic, or fused, spiro-fused, and/or bridged bicyclic and polycyclic ring systems where at least one ring is saturated or partially unsaturated (but not aromatic) and comprises a heteroatom. A heterocyclic ring system can be attached to its pendant group at any heteroatom or carbon atom that results in a stable structure and any of the ring atoms can be optionally substituted.

The term "heterocyclyl" refers to a radical of a heterocyclic ring system. Representative heterocyclyls include ring systems in which (I) every ring is non-aromatic and at least one ring comprises a heteroatom, e.g., tetrahydrofuranyl, tetrahydrothienyl, pyrrolidinyl, pyrrolidonyl, piperidinyl, pyrrolinyl, decahydroquinolinyl, oxazolidinyl, piperazinyl, dioxanyl, dioxolanyl, diazepinyl, oxazepinyl, thiazepinyl, morpholinyl, and quinuclidinyl; (ii) at least one ring is non-aromatic and comprises a heteroatom and at least one other ring is an aromatic carbon ring, e.g., 1,2,3,4-tetrahydroquinolinyl, 1,2,3,4-tetrahydroisoquinolinyl; and (iii) at least one ring is non-aromatic and comprises a heteroatom and at least one other ring is aromatic and comprises a heteroatom, e.g., 3,4-dihydro-1H-pyrano[4,3-c]pyridine, and 1,2,3,4-tetrahydro-2,6-naphthyridine. In certain embodiments, the heterocyclyl is a monocyclic or bicyclic ring, wherein each of said rings contains 3-7 ring atoms where 1, 2, 3, or 4 of said ring atoms are a heteroatom independently selected from N, O, and S.

The term "saturated heterocyclyl" refers to a radical of heterocyclic ring system wherein every ring is saturated, e.g., tetrahydrofuran, tetrahydro-2H-pyran, pyrrolidine, piperidine and piperazine.

"Partially unsaturated" refers to a group that includes at least one double or triple bond. A "partially unsaturated" ring system is further intended to encompass rings having multiple sites of unsaturation, but is not intended to include aromatic groups (e.g., aryl or heteroaryl groups) as herein defined. Likewise, "saturated" refers to a group that does not contain a double or triple bond, i.e., contains all single bonds.

As described herein, compounds of the invention may contain "optionally substituted" moieties. In general, the term "substituted", whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at each position. Combinations of substituents envisioned under this invention are preferably those that result in the formation of stable or chemically feasible compounds. The term "stable", as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group (such as an alkyl, alkenyl, alkynyl, alkylene, alkenylene, alkynylene or the carbon atom of a carbocyclyl, aryl, heterocyclyl or heteroaryl) are independently deuterium; halogen; —$(CH_2)_{0-4}R^°$; —$(CH_2)_{0-4}OR^°$; —O—$(CH_2)_{0-4}C(O)OR^°$; —$(CH_2)_{0-4}CH(OR^°)_2$, —$(CH_2)_{0-4}SR^°$; —$(CH_2)_{0-4}Ph$ (where "Ph" is phenyl), which may be substituted with $R^°$; —$(CH_2)_{0-4}O(CH_2)_{0-1}Ph$ which may be substituted with $R^°$; —CH=CHPh, which may be substituted with —$R^°$; —$NO_2$; —CN; —$N_3$; —$(CH_2)_{0-4}N(R^°)_2$; —$(CH_2)_{0-4}N(R^°)C(O)R^°$; —$N(R^°)C(S)R^°$; —$(CH_2)_{0-4}N(R^°)C(O)NR^°_2$; —$N(R^°)C(S)NR^°_2$; —$(CH_2)_{0-4}N(R^°)C(O)OR^°$; —$N(R^°)N(R^°)C(O)R^°$; —$N(R^°)N(R^°)C(O)NR^°_2$; —$N(R^°)N(R^°)C(O)OR^°$; —$(CH_2)_{0-4}C(O)R^°$; —$C(S)R^°$; —$(CH_2)_{0-4}C(O)OR^°$; —$(CH_2)_{0-4}C(O)SR^°$; —$(CH_2)_{0-4}C(O)OSiR^°_3$; —$(CH_2)_{0-4}C(O)—N(R^°)—S(O)_2—R^°$, —$(CH_2)_{0-4}OC(O)R^°$; —OC(O)$(CH_2)_{0-4}SR^°$—, —SC(S)SR^°$; —$(CH_2)_{0-4}SC(O)R^°$; —$(CH_2)_{0-4}C(O)NR^°_2$; —$C(S)NR^°_2$; —$C(S)SR^°$; —$(CH_2)_{0-4}OC(O)NR^°_2$; —C(O)N(OR^°)R^°$; —C(O)C(O)R^°$; —C(O)CH_2C(O)R^°$; —C(NOR^°)R^°$; —$(CH_2)_{0-4}SSR^°$; —$(CH_2)_{0-4}S(O)_2R^°$; —$(CH_2)_{0-4}S(O)_2OR^°$; —$(CH_2)_{0-4}OS(O)_2R^°$; —S(O)_2NR^°_2$; —$(CH_2)_{0-4}S(O)R^°$; —$N(R^°)S(O)_2NR^°_2$; —$N(R^°)S(O)_2R^°$; —$N(OR^°)R^°$; —C(NH)NR^°_2$; —$P(O)_2R^°$; —$P(O)R^°_2$; —$OP(O)R^°_2$; —$OP(O)(OR^°)_2$; —$SiR^°_3$; —$(C_{1-4}$ straight or branched alkylene)O—$N(R^°)_2$; or —$(C_{1-4}$ straight or branched)alkylene)C(O)O—$N(R^°)_2$, wherein each $R^°$ may be substituted as defined below and is independently hydrogen, deuterium, $C_{1-6}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur, or, notwithstanding the definition above, two independent occurrences of $R^°$, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on $R^°$ (or the ring formed by taking two independent occurrences of $R^°$ together with their intervening atoms), are independently deuterium, halogen, —$(CH_2)_{0-2}R^•$, -(haloR^•$), —$(CH_2)_{0-2}$OH, —$(CH_2)_{0-2}OR^•$, —$(CH_2)_{0-2}CH(OR^•)_2$; —O(haloR^•$), —CN, —$N_3$, —$(CH_2)_{0-2}C(O)R^•$, —$(CH_2)_{0-2}C(O)OH$, —$(CH_2)_{0-2}C(O)OR^•$, —$(CH_2)_{0-2}SR^•$, —$(CH_2)_{0-2}SH$, —(CH$_2$)$_{0-2}$NH$_2$, —(CH$_2$)$_{0-2}$NHR$^\bullet$, —(CH$_2$)$_{0-2}$NR$^\bullet_2$, —NO$_2$, —SiR$^\bullet_3$, —OSiR$^\bullet_3$, —C(O)SR$^\bullet$, —(C$_{1-4}$ straight or branched alkylene)C(O)OR$^\bullet$, or —SSR$^\bullet$ wherein each R$^\bullet$ is unsubstituted or where preceded by "halo" is substituted only with one or more halogens, and is independently selected from C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur. Suitable divalent substituents on a saturated carbon atom of R° include =O and =S.

Suitable divalent substituents on a saturated carbon atom of an "optionally substituted" group include the following: =O, =S, =NNR*$_2$, =NNHC(O)R*, =NNHC(O)OR*, =NNHS(O)$_2$R*, =NR*, =NOR*, —O(C(R*$_2$))$_{2-3}$O—, or —S(C(R*$_2$))$_{2-3}$S—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include deuterium, halogen, —R$^\bullet$, -(haloR$^\bullet$), —OH, —OR*, —O(haloR$^\bullet$), —CN, —C(O)OH, —C(O)OR$^\bullet$, —NH$_2$, —NHR$^\bullet$, —NR$^\bullet_2$, or —NO$_2$, wherein each R$^\bullet$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R$^\dagger$, —NR$^\dagger_2$, —C(O)R$^\dagger$, —C(O)OR$^\dagger$, —C(O)C(O)R$^\dagger$, —C(O)CH$_2$C(O)R$^\dagger$, —S(O)$_2$R$^\dagger$, —S(O)$_2$NR$^\dagger_2$, —C(S)NR$^\dagger_2$, —C(NH)NR$^\dagger_2$, or —N(R$^\dagger$)S(O)$_2$R$^\dagger$; wherein each R$^\dagger$ is independently hydrogen, C$_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R$^\dagger$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of R$^\dagger$ are independently deuterium, halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet_2$, or —NO$_2$, wherein each R$^\bullet$ is unsubstituted or where preceded by "halo" is substituted only with one or more halogens, and is independently C$_{1-4}$aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

"Halo" or "halogen" refers to fluorine (fluoro, —F), chlorine (chloro, —Cl), bromine (bromo, —Br), or iodine (iodo, —I).

The term "one or more methylene units of the alkylene, alkenylene or alkynylene is optionally replaced with —O—, —S—, —S(=O)$_2$, or —NR$^X$—" as used herein means that none, one, more than one, or all of the methylene units present may be so replaced. Thus, for example, the moieties, —O—, —S—, and —NR$^X$— are included in this definition because in each case they represent a C$_1$ alkylene (i.e., methylene) replaced with —O—, —S—, or —NR$^X$—, respectively.

It should also be understood that reference to a variable or subvariable in Formula I (e.g., R$^2$, R$^4$ or R$^5$) being "an optionally substituted C$_1$-C$_4$ alkylene, and an optionally substituted C$_2$-C$_4$ alkenylene or alkynylene, wherein: one or more methylene units of the alkylene, alkenylene or alkynylene other than a methylene unit bound to a nitrogen atom is optionally and independently replaced with —O—, —S—, —N(R$^6$)—, or —S(=O)$_2$—" is only intended to encompass chemically stable combinations of optionally substitutions and replacements.

As used herein, the term "leaving group" is given its ordinary meaning in the art of synthetic organic chemistry and refers to an atom or a group capable of being displaced by a nucleophile. Examples of suitable leaving groups include, but are not limited to, halogen (such as F, Cl, Br, or I (iodine)), alkoxycarbonyloxy, aryloxycarbonyloxy, alkanesulfonyloxy, arenesulfonyloxy, alkyl-carbonyloxy (e.g., acetoxy), arylcarbonyloxy, aryloxy, methoxy, N,O-dimethylhydroxylamino, pixyl, and haloformates. In some cases, the leaving group is a sulfonic acid ester, such as toluenesulfonate (tosylate, —OTs), methanesulfonate (mesylate, —OMs), p-bromobenzenesulfonyloxy (brosylate, —OBs), or trifluoromethanesulfonate (triflate, —OTf). In some cases, the leaving group is a brosylate, such as p-bromobenzenesulfonyloxy. In some cases, the leaving group is a nosylate, such as 2-nitrobenzenesulfonyloxy. In some embodiments, the leaving group is a sulfonate-containing group. In some embodiments, the leaving group is a tosylate group. The leaving group may also be a phosphineoxide (e.g., formed during a Mitsunobu reaction) or an internal leaving group such as an epoxide or cyclic sulfate. Other non-limiting examples of leaving groups are water, ammonia, alcohols, ether moieties, thioether moieties, zinc halides, magnesium moieties, diazonium salts, and copper moieties.

These and other exemplary substituents are described in more detail in the Detailed Description, FIGURES, Examples, and Claims. The invention is not intended to be limited in any manner by the above exemplary listing of substituents.

Other Definitions

The following definitions are more general terms used throughout the present application:

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, Berge et al., describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid, and perchloric acid or with organic acids such as acetic acid, oxalic acid, maleic acid, tartaric acid, citric acid, succinic acid, or malonic acid or by using other methods known in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}$ alkyl$)_4^-$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

The term "solvate" refers to forms of the compound that are associated with a solvent, usually by a solvolysis reaction. This physical association may include hydrogen bonding. Conventional solvents include water, methanol, ethanol, acetic acid, DMSO, THF, diethyl ether, and the like. The compounds of Formula (I) may be prepared, e.g., in crystalline form, and may be solvated. Suitable solvates include pharmaceutically acceptable solvates and further include both stoichiometric solvates and non-stoichiometric solvates. In certain instances, the solvate will be capable of isolation, for example, when one or more solvent molecules are incorporated in the crystal lattice of a crystalline solid. "Solvate" encompasses both solution-phase and isolable solvates. Representative solvates include hydrates, ethanolates, and methanolates.

The term "hydrate" refers to a compound which is associated with water. Typically, the number of the water molecules contained in a hydrate of a compound is in a definite ratio to the number of the compound molecules in the hydrate. Therefore, a hydrate of a compound may be represented, for example, by the general formula $R.x\ H_2O$, wherein R is the compound and wherein x is a number greater than 0. A given compound may form more than one type of hydrates, including, e.g., monohydrates (x is 1), lower hydrates (x is a number greater than 0 and smaller than 1, e.g., hemihydrates ($R.0.5H_2O$)), and polyhydrates (x is a number greater than 1, e.g., dihydrates ($R.2H_2O$) and hexahydrates ($R.6H_2O$)).

The term "tautomers" refer to compounds that are interchangeable forms of a particular compound structure, and that vary in the displacement of hydrogen atoms and electrons. Thus, two structures may be in equilibrium through the movement of π electrons and an atom (usually H). For example, enols and ketones are tautomers because they are rapidly interconverted by treatment with either acid or base. Another example of tautomerism is the aci- and nitro-forms of phenylnitromethane that are likewise formed by treatment with acid or base.

Tautomeric forms may be relevant to the attainment of the optimal chemical reactivity and biological activity of a compound of interest.

It is also to be understood that compounds that have the same molecular formula but differ in the nature or sequence of bonding of their atoms or the arrangement of their atoms in space are termed "isomers". Isomers that differ in the arrangement of their atoms in space are termed "stereoisomers".

Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

A "subject" to which administration is contemplated includes, but is not limited to, humans (i.e., a male or female of any age group, e.g., a pediatric subject (e.g., infant, child, adolescent) or adult subject (e.g., young adult, middleaged adult, or senior adult)) and/or other nonhuman animals, for example, mammals (e.g., primates (e.g., cynomolgus monkeys, rhesus monkeys); commercially relevant mammals such as cattle, pigs, horses, sheep, goats, cats, and/or dogs) and birds (e.g., commercially relevant birds such as chickens, ducks, geese, and/or turkeys). In certain embodiments, the animal is a mammal. The animal may be a male or female and at any stage of development. A nonhuman animal may be a transgenic animal.

The terms "administer," "administering," or "administration," as used herein refers to implanting, absorbing, ingesting, injecting, inhaling, or otherwise introducing an inventive compound, or a pharmaceutical composition thereof.

As used herein, the terms "treatment," "treat," and "treating" refer to reversing, alleviating, delaying the onset of, or inhibiting the progress of a "pathological condition" (e.g., a disease, disorder, or condition, or one or more signs or symptoms thereof) described herein. In some embodiments, "treatment," "treat," and "treating" require that signs or symptoms of the disease disorder or condition have developed or have been observed. In other embodiments, treatment may be administered in the absence of signs or symptoms of the disease or condition. For example, treatment may be administered to a susceptible individual prior to the onset of symptoms (e.g., in light of a history of symptoms and/or in light of genetic or other susceptibility factors). Treatment may also be continued after symptoms have resolved, for example, to delay or prevent recurrence.

As used herein, the terms "condition," "disease," and "disorder" are used interchangeably.

An "effective amount" of a compound of Formula (I) refers to an amount sufficient to elicit the desired biological response, i.e., treating the condition. As will be appreciated by those of ordinary skill in this art, the effective amount of a compound of Formula (I) may vary depending on such factors as the desired biological endpoint, the pharmacokinetics of the compound, the condition being treated, the mode of administration, and the age and health of the subject. An effective amount encompasses therapeutic and prophylactic treatment. For example, in treating cancer, an effective amount of an inventive compound may reduce the tumor burden or stop the growth or spread of a tumor.

A "therapeutically effective amount" of a compound of Formula (I) is an amount sufficient to provide a therapeutic benefit in the treatment of a condition or to delay or minimize one or more symptoms associated with the condition. In some embodiments, a therapeutically effective amount is an amount sufficient to provide a therapeutic benefit in the treatment of a condition or to minimize one or more symptoms associated with the condition. A therapeutically effective amount of a compound means an amount of therapeutic agent, alone or in combination with other therapies, which provides a therapeutic benefit in the treatment of the condition. The term "therapeutically effective amount" can encompass an amount that improves overall therapy, reduces or avoids symptoms or causes of the condition, or enhances the therapeutic efficacy of another therapeutic agent.

A "prophylactically effective amount" of a compound of Formula (I) is an amount sufficient to prevent a condition, or one or more symptoms associated with the condition or prevent its recurrence. A prophylactically effective amount of a compound means an amount of a therapeutic agent, alone or in combination with other agents, which provides a prophylactic benefit in the prevention of the condition. The term "prophylactically effective amount" can encompass an amount that improves overall prophylaxis or enhances the prophylactic efficacy of another prophylactic agent.

A "proliferative disease" refers to a disease that occurs due to abnormal growth or extension by the multiplication of cells (Walker, *Cambridge Dictionary of Biology*; Cambridge University Press: Cambridge, UK, 1990). A proliferative disease may be associated with: 1) the pathological proliferation of normally quiescent cells; 2) the pathological migration of cells from their normal location (e.g., metastasis of neoplastic cells); 3) the pathological expression of proteolytic enzymes such as the matrix metalloproteinases (e.g., collagenases, gelatinases, and elastases); or 4) the pathological angiogenesis as in proliferative retinopathy and tumor metastasis. Exemplary proliferative diseases include cancers (i.e., "malignant neoplasms"), benign neoplasms, angiogenesis, inflammatory diseases, autoinflammatory diseases, and autoimmune diseases.

The terms "neoplasm" and "tumor" are used herein interchangeably and refer to an abnormal mass of tissue wherein the growth of the mass surpasses and is not coordinated with the growth of a normal tissue. A neoplasm or tumor may be "benign" or "malignant," depending on the following characteristics: degree of cellular differentiation (including morphology and functionality), rate of growth, local invasion, and metastasis. A "benign neoplasm" is generally well differentiated, has characteristically slower growth than a malignant neoplasm, and remains localized to the site of origin. In addition, a benign neoplasm does not have the capacity to infiltrate, invade, or metastasize to distant sites. Exemplary benign neoplasms include, but are not limited to, lipoma, chondroma, adenomas, acrochordon, senile angiomas, seborrheic keratoses, lentigos, and sebaceous hyperplasias. In some cases, certain "benign" tumors may later give rise to malignant neoplasms, which may result from additional genetic changes in a subpopulation of the tumor's neoplastic cells, and these tumors are referred to as "premalignant neoplasms." An exemplary pre-malignant neoplasm is a teratoma. In contrast, a "malignant neoplasm" is generally poorly differentiated (anaplasia) and has characteristically rapid growth accompanied by progressive infiltration, invasion, and destruction of the surrounding tissue. Furthermore, a malignant neoplasm generally has the capacity to metastasize to distant sites.

As used herein, the term "cancer" refers to a malignant neoplasm (*Stedman's Medical Dictionary*, 25th ed.; Hensyl ed.; Williams & Wilkins: Philadelphia, 1990). Exemplary cancers include, but are not limited to, acoustic neuroma; adenocarcinoma; adrenal gland cancer; anal cancer; angiosarcoma (e.g., lymphangiosarcoma, lymphangioendotheliosarcoma, hemangiosarcoma); appendix cancer; benign monoclonal gammopathy; biliary cancer (e.g., cholangiocarcinoma); bladder cancer; breast cancer (e.g., adenocarcinoma of the breast, papillary carcinoma of the breast, mammary cancer, medullary carcinoma of the breast); brain cancer (e.g., meningioma, glioblastomas, glioma (e.g., astrocytoma, oligodendroglioma), medulloblastoma); bronchus cancer; carcinoid tumor; cervical cancer (e.g., cervical adenocarcinoma); choriocarcinoma; chordoma; craniopharyngioma; colorectal cancer (e.g., colon cancer, rectal cancer, colorectal adenocarcinoma); connective tissue cancer; epithelial carcinoma; ependymoma; endothelio sarcoma (e.g., Kaposi's sarcoma, multiple idiopathic hemorrhagic sarcoma); endometrial cancer (e.g., uterine cancer, uterine sarcoma); esophageal cancer (e.g., adenocarcinoma of the esophagus, Barrett's adenocarcinoma); Ewing's sarcoma; eye cancer (e.g., intraocular melanoma, retinoblastoma); familiar hypereosinophilia; gall bladder cancer; gastric cancer (e.g., stomach adenocarcinoma); gastrointestinal stromal tumor (GIST); germ cell cancer; head and neck cancer (e.g., head and neck squamous cell carcinoma, oral cancer (e.g., oral squamous cell carcinoma), throat cancer (e.g., laryngeal cancer, pharyngeal cancer, nasopharyngeal cancer, oropharyngeal cancer)); hematopoietic cancers (e.g., leukemia such as acute lymphocytic leukemia (ALL) (e.g., B-cell ALL, T-cell ALL), acute myelocytic leukemia (AML) (e.g., B-cell AML, T-cell AML), chronic myelocytic leukemia (CML) (e.g., B-cell CML, T-cell CML), and chronic lymphocytic leukemia (CLL) (e.g., B-cell CLL, T-cell CLL)); lymphoma such as Hodgkin lymphoma (HL) (e.g., B-cell HL, T-cell HL) and non-Hodgkin lymphoma (NHL) (e.g., B-cell NHL such as diffuse large cell lymphoma (DLCL) (e.g., diffuse large B-cell lymphoma), follicular lymphoma, chronic lymphocytic leukemia/small lymphocytic lymphoma (CLL/SLL), mantle cell lymphoma (MCL), marginal zone B-cell lymphomas (e.g., mucosa-associated lymphoid tissue (MALT) lymphomas, nodal marginal zone B-cell lymphoma, splenic marginal zone B-cell lymphoma), primary mediastinal B-cell lymphoma, Burkitt lymphoma, lymphoplasmacytic lymphoma (i.e., Waldenström's macroglobulinemia), hairy cell leukemia (HCL), immunoblastic large cell lymphoma, precursor B-lymphoblastic lymphoma and primary central nervous system (CNS) lymphoma; and T-cell NHL such as precursor T-lymphoblastic lymphoma/leukemia, peripheral T-cell lymphoma (PTCL) (e.g., cutaneous T-cell lymphoma (CTCL) (e.g., mycosis fungoides, Sezary syndrome), angioimmunoblastic T-cell lymphoma, extranodal natural killer T-cell lymphoma, enteropathy type T-cell lymphoma, subcutaneous panniculitis-like T-cell lymphoma, and anaplastic large cell lymphoma); a mixture of one or more leukemia/lymphoma as described above; and multiple myeloma (MM)), heavy chain disease (e.g., alpha chain disease, gamma chain disease, mu chain disease); hemangioblastoma; hypopharynx cancer; inflammatory myofibroblastic tumors; immunocytic amyloidosis; kidney cancer (e.g., nephroblastoma a.k.a. Wilms' tumor, renal cell carcinoma); liver cancer (e.g., hepatocellular cancer (HCC), malignant hepatoma); lung cancer (e.g., bronchogenic carcinoma, small cell lung cancer (SCLC), non-small cell lung cancer (NSCLC), adenocarcinoma of the lung); leiomyosarcoma (LMS); mastocytosis (e.g., systemic mastocytosis); muscle cancer; myelodysplastic syndrome (MDS); mesothelioma; myeloproliferative disorder (MPD) (e.g., polycythemia vera (PV), essential thrombocytosis (ET), agnogenic myeloid metaplasia (AMM) a.k.a. myelofibrosis (MF), chronic idiopathic myelofibrosis, chronic myelocytic leukemia (CML), chronic neutrophilic leukemia (CNL), hypereosinophilic syndrome (HES)); neuroblastoma; neurofibroma (e.g., neurofibromatosis (NF) type 1 or type 2, schwannomatosis); neuroendocrine cancer (e.g., gastroenteropancreatic neuroendocrine tumor (GEP-NET), carcinoid tumor); osteosarcoma (e.g., bone cancer); ovarian cancer (e.g., cystadenocarcinoma, ovarian embryonal carcinoma, ovarian adenocarcinoma); papillary adenocarcinoma; pancreatic cancer (e.g., pancreatic adenocarcinoma, intraductal papillary mucinous neoplasm (IPMN), Islet cell tumors); penile cancer (e.g., Paget's disease of the penis and scrotum); pinealoma; primitive neuroectodermal tumor (PNT); plasma cell neoplasia; paraneoplastic syndromes; intraepithelial neoplasms; prostate cancer (e.g., prostate adenocarcinoma); rectal cancer; rhabdomyosarcoma; salivary gland cancer; skin cancer (e.g., squamous cell carcinoma (SCC), keratoacanthoma (KA), melanoma, basal cell carcinoma (BCC)); small bowel cancer (e.g., appendix cancer); soft tissue sarcoma (e.g., malignant fibrous histiocytoma (MFH), liposarcoma, malignant peripheral nerve sheath tumor (MPNST), chondrosarcoma, fibrosarcoma, myxosarcoma); sebaceous gland carcinoma; small intestine cancer; sweat gland carcinoma; synovioma; testicular cancer (e.g., seminoma, testicular embryonal carcinoma); thyroid cancer (e.g., papillary carcinoma of the thyroid, papillary thyroid carcinoma (PTC), medullary thyroid cancer); urethral cancer; vaginal cancer; and vulvar cancer (e.g., Paget's disease of the vulva).

The term "angiogenesis" refers to the formation and the growth of new blood vessels. Normal angiogenesis occurs in the healthy body of a subject for healing wounds and for restoring blood flow to tissues after injury. The healthy body controls angiogenesis through a number of means, e.g., angiogenesis-stimulating growth factors and angiogenesis inhibitors. Many disease states, such as cancer, diabetic blindness, age-related macular degeneration, rheumatoid arthritis, and psoriasis, are characterized by abnormal (i.e., increased or excessive) angiogenesis. Abnormal angiogenesis refers to angiogenesis greater than that in a normal body, especially angiogenesis in an adult not related to normal angiogenesis (e.g., menstruation or wound healing). Abnormal angiogenesis can provide new blood vessels that feed diseased tissues and/or destroy normal tissues, and in the case of cancer, the new vessels can allow tumor cells to escape into the circulation and lodge in other organs (tumor metastases).

As used herein, an "inflammatory disease" refers to a disease caused by, resulting from, or resulting in inflammation. The term "inflammatory disease" may also refer to a dysregulated inflammatory reaction that causes an exaggerated response by macrophages, granulocytes, and/or T-lymphocytes leading to abnormal tissue damage and/or cell death. An inflammatory disease can be either an acute or chronic inflammatory condition and can result from infections or non-infectious causes Inflammatory diseases include, without limitation, atherosclerosis, arteriosclerosis, autoimmune disorders, multiple sclerosis, systemic lupus erythematosus, polymyalgia rheumatica (PMR), gouty arthritis, degenerative arthritis, tendonitis, bursitis, psoriasis, cystic fibrosis, arthrosteitis, rheumatoid arthritis, inflammatory arthritis, Sjogren's syndrome, giant cell arteritis, progressive systemic sclerosis (scleroderma), ankylosing spondylitis, polymyositis, dermatomyositis, pemphigus, pemphigoid, diabetes (e.g., Type I), myasthenia gravis, Hashimoto's thyroiditis, Graves' disease, Goodpasture's disease, mixed connective tissue disease, sclerosing cholangitis, inflammatory bowel disease, Crohn's disease, ulcerative colitis, pernicious anemia, inflammatory dermatoses, usual interstitial pneumonitis (UIP), asbestosis, silicosis, bronchiectasis, berylliosis, talcosis, pneumoconiosis, sarcoidosis, desquamative interstitial pneumonia, lymphoid interstitial pneumonia, giant cell interstitial pneumonia, cellular interstitial pneumonia, extrinsic allergic alveolitis, Wegener's granulomatosis and related forms of angiitis (temporal arteritis and polyarteritis *nodosa*), inflammatory dermatoses, hepatitis, delayed-type hypersensitivity reactions (e.g., poison ivy dermatitis), pneumonia, respiratory tract inflammation, Adult Respiratory Distress Syndrome (ARDS), encephalitis, immediate hypersensitivity reactions, asthma, hayfever, allergies, acute anaphylaxis, rheumatic fever, glomerulonephritis, pyelonephritis, cellulitis, cystitis, chronic cholecystitis, ischemia (ischemic injury), reperfusion injury, allograft rejection, host-versus-graft rejection, appendicitis, arteritis, blepharitis, bronchiolitis, bronchitis, cervicitis, cholangitis, chorioamnionitis, conjunctivitis, dacryoadenitis, dermatomyositis, endocarditis, endometritis, enteritis, enterocolitis, epicondylitis, epididymitis, fasciitis, fibrositis, gastritis, gastroenteritis, gingivitis, ileitis, iritis, laryngitis, myelitis, myocarditis, nephritis, omphalitis, oophoritis, orchitis, osteitis, otitis, pancreatitis, parotitis, pericarditis, pharyngitis, pleuritis, phlebitis, pneumonitis, proctitis, prostatitis, rhinitis, salpingitis, sinusitis, stomatitis, synovitis, testitis, tonsillitis, urethritis, urocystitis, uveitis, vaginitis, vasculitis, vulvitis, vulvovaginitis, angitis, chronic bronchitis, osteomyelitis, optic neuritis, temporal arteritis, transverse myelitis, necrotizing fasciitis, and necrotizing enterocolitis.

As used herein, an "autoimmune disease" refers to a disease arising from an inappropriate immune response of the body of a subject against substances and tissues normally present in the body. In other words, the immune system mistakes some part of the body as a pathogen and attacks its own cells. This may be restricted to certain organs (e.g., in autoimmune thyroiditis) or involve a particular tissue in different places (e.g., Goodpasture's disease which may affect the basement membrane in both the lung and kidney). The treatment of autoimmune diseases is typically with immunosuppression, e.g., medications which decrease the immune response. Exemplary autoimmune diseases include, but are not limited to, glomerulonephritis, Goodpasture's syndrome, necrotizing vasculitis, lymphadenitis, peri-arteritis nodosa, systemic lupus erythematosis, rheumatoid, arthritis, psoriatic arthritis, systemic lupus erythematosis, psoriasis, ulcerative colitis, systemic sclerosis, dermatomyositis/polymyositis, anti-phospholipid antibody syndrome, scleroderma, pemphigus vulgaris, ANCA-associated vasculitis (e.g., Wegener's granulomatosis, microscopic polyangiitis), uveitis, Sjogren's syndrome, Crohn's disease, Reiter's syndrome, ankylosing spondylitis, Lyme arthritis, Guillain-Barré syndrome, Hashimoto's thyroiditis, and cardiomyopathy.

The term "autoinflammatory disease" refers to a category of diseases that are similar but different from autoimmune diseases. Autoinflammatory and autoimmune diseases share common characteristics in that both groups of disorders result from the immune system attacking a subject's own tissues and result in increased inflammation. In autoinflammatory diseases, a subject's innate immune system causes inflammation for unknown reasons. The innate immune system reacts even though it has never encountered autoantibodies or antigens in the subject. Autoinflammatory disorders are characterized by intense episodes of inflammation that result in such symptoms as fever, rash, or joint swelling. These diseases also carry the risk of amyloidosis, a potentially fatal buildup of a blood protein in vital organs. Autoinflammatory diseases include, but are not limited to, familial Mediterranean fever (FMF), neonatal onset multisystem inflammatory disease (NOMID), tumor necrosis factor (TNF) receptor-associated periodic syndrome (TRAPS), deficiency of the interleukin-1 receptor antagonist (DIRA), and Behçet's disease.

The term "biological sample" refers to any sample including tissue samples (such as tissue sections and needle biopsies of a tissue); cell samples (e.g., cytological smears (such as Pap or blood smears) or samples of cells obtained by microdissection); samples of whole organisms (such as samples of yeasts or bacteria); or cell fractions, fragments or organelles (such as obtained by lysing cells and separating the components thereof by centrifugation or otherwise). Other examples of biological samples include blood, serum, urine, semen, fecal matter, cerebrospinal fluid, interstitial fluid, mucus, tears, sweat, pus, biopsied tissue (e.g., obtained by a surgical biopsy or needle biopsy), nipple aspirates, milk, vaginal fluid, saliva, swabs (such as buccal swabs), or any material containing biomolecules that is derived from a first biological sample. Biological samples also include those biological samples that are transgenic, such as transgenic oocyte, sperm cell, blastocyst, embryo, fetus, donor cell, or cell nucleus.

DETAILED DESCRIPTION OF CERTAIN EMBODIMENTS OF THE INVENTION

Compounds

In one embodiment of the present invention, provided are compounds of Formula (I): compound having the structural formula I:

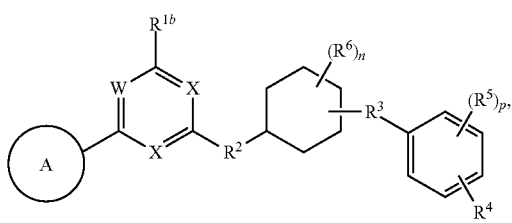

(I)

or a pharmaceutically acceptable salt, solvate, hydrate, tautomer, or stereoisomer thereof, wherein:

ring A is an optionally substituted heteroaryl ring of any one of the Formulae (i-1)-(i-6):

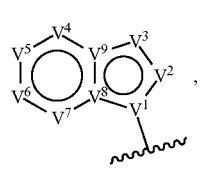

(i-1)

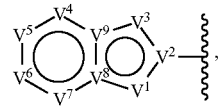

(i-2)

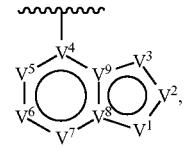

(i-3)

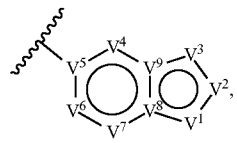

(i-4)

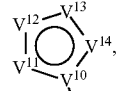

(i-5)

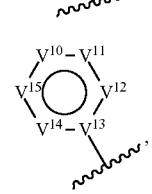

(i-6)

wherein:
each instance of $V^1$, $V^2$, $V^3$, $V^4$, $V^5$, $V^6$, $V^7$, $V^8$, $V^9$, $V^{10}$, $V^{11}$, $V^{12}$, $V^{13}$, $V^{14}$ and $V^{15}$ is independently O, S, N, N($R^{41}$), C, or C($R^{42}$);

each instance of $R^{41}$ is independently selected from hydrogen, deuterium, optionally substituted acyl, optionally substituted alkyl, optionally substituted alkenyl, optionally substituted alkynyl, optionally substituted carbocyclyl, optionally substituted heterocyclyl, optionally substituted aryl, and optionally substituted heteroaryl;

each instance of $R^{42}$ is independently selected from hydrogen, deuterium, halogen, —CN, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, —$OR^{42a}$, —$N(R^{42a})_2$, and —$SR^{42a}$, wherein each occurrence of $R^{42a}$ is independently selected from hydrogen, optionally substituted acyl, optionally substituted alkyl, optionally substituted alkenyl, optionally substituted alkynyl, optionally substituted carbocyclyl, optionally substituted heterocyclyl, optionally substituted aryl, and optionally substituted heteroaryl, or any two $R^{41}$, any two $R^{42}$, or one $R^{41}$ and one $R^{42}$ are joined to form an optionally substituted carbocyclic, optionally substituted heterocyclic, optionally substituted aryl, or optionally substituted heteroaryl ring;

each X is independently selected from N and CH, wherein at least one X is N;

W is selected from N and C($R^{1a}$);

each of $R^{1a}$, if present, and $R^{1b}$ is independently selected from hydrogen, deuterium, halogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, —CN, —OR$^{B1a}$, —N(R$^{B1a}$)$_2$, and —SR$^{B1a}$, wherein each occurrence of R$^{B1a}$ is independently selected from hydrogen, optionally substituted acyl, optionally substituted alkyl, optionally substituted alkenyl, optionally substituted alkynyl, optionally substituted carbocyclyl, optionally substituted heterocyclyl, optionally substituted aryl, and optionally substituted heteroaryl, or R$^{1a}$ and R$^{1b}$ are joined to form an optionally substituted carbocyclic, optionally substituted heterocyclic, optionally substituted aryl, or optionally substituted heteroaryl ring;

R$^2$ is an optionally substituted C$_1$-C$_4$ alkylene or an optionally substituted C$_2$-C$_4$ alkenylene or alkynylene, wherein one or more methylene units of the alkylene, alkenylene or alkynylene are optionally and independently replaced with —O—, —S—, or —N(R$^7$)—;

R$^3$ is selected from a bond, an optionally substituted C$_1$-C$_4$ alkylene, and an optionally substituted C$_2$-C$_4$ alkenylene or alkynylene, wherein one or more methylene units of the alkylene, alkenylene or alkynylene is optionally and independently replaced with —O—, —S—, —N(R$^7$)—, or —S(O)$_2$—;

R$^4$ is selected from —C$_1$-C$_8$ alkyl, —O—C$_1$-C$_8$ alkyl, —NH$_2$, —NH(C$_1$-C$_8$ alkyl), and —N(C$_1$-C$_8$ alkyl)$_2$, wherein each alkyl in R$^4$ is optionally and independently substituted.

each R$^5$, if present, is independently selected from deuterium, halogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, —OR$^{D1}$, —N(R$^{D1}$)$_2$, and —SR$^{D1}$, wherein each occurrence of R$^{D1}$ is independently selected from hydrogen, optionally substituted acyl, optionally substituted alkyl, optionally substituted alkenyl, optionally substituted alkynyl, optionally substituted carbocyclyl, optionally substituted heterocyclyl, and optionally substituted aryl, optionally substituted heteroaryl;

each R$^6$, if present, is independently selected from the group consisting of deuterium, halogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, =O, —CN, —OR$^{C1}$, —N(R$^{C1}$)$_2$, and —SR$^{C1}$, wherein each occurrence of R$^{C1}$ is independently selected from the group consisting of hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, a nitrogen protecting group when attached to a nitrogen atom, an oxygen protecting group when attached to an oxygen atom, and a sulfur protecting group when attached to a sulfur atom, or two R$^{C1}$ groups are joined to form an optionally substituted heterocyclic ring; or two R$^6$ are taken together to form a first 5-7 membered, optionally substituted, heterocyclyl or carbocyclyl ring fused to the ring to which the R$^6$ are bound, wherein two substituents on the substituted heterocyclyl or carbocyclyl ring, or one substituent on the substituted heterocyclyl or carbocyclyl ring and a third R$^6$ may be taken together with the atoms to which they are bound to form a second optionally substituted, heterocyclyl or carbocyclyl ring fused to the ring to the first optionally substituted, heterocyclyl or carbocyclyl ring and/or the ring to which the third R$^6$ is bound;

each R$^7$ is independently selected from hydrogen, and optionally substituted —C$_1$-C$_6$ alkyl;

n is 0, 1, 2, 3, 4, 5 or 6; and p is 0, 1, 2 or 3.

In certain embodiments, the compound is other than

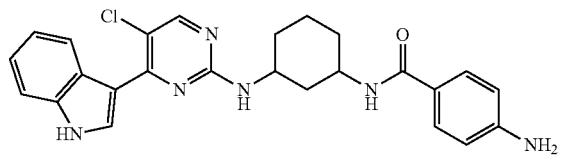 [SMILES: Nc1ccc(C(=O)NC2CCCC(Nc3ncc(Cl)c(-c4c[nH]c5ccccc45)n3)C2)cc1]

and stereoisomers and enantiomers thereof.

In certain embodiments, no more than three of V$^1$, V$^2$, V$^3$, V$^4$, V$^5$, V$^6$, V$^7$, V$^8$, and V$^9$ are each independently selected from the group consisting of O, S, N, and N(R$^{41}$).

In certain embodiments, one of V$^{10}$, V$^{11}$, V$^{12}$, V$^{13}$, V$^{14}$ and V$^{15}$ is N and the others of V$^{10}$, V$^{11}$, V$^{12}$, V$^{13}$, V$^{14}$ and V$^{15}$ are independently C(R$^{42}$).

In certain embodiments, one or two of V$^1$, V$^2$, V$^3$, V$^4$, V$^5$, V$^6$, V$^7$, V$^8$, and V$^9$ are each independently selected from the group consisting of N and N(R$^{41}$); each of V$^1$, V$^2$, V$^3$, V$^4$, V$^5$, V$^6$, and V$^7$ that is not N(R$^{41}$) is independently C(R$^{42}$); and each V$^8$ and V$^9$ that is not N is C. In one aspect of these embodiments, ring A is selected from

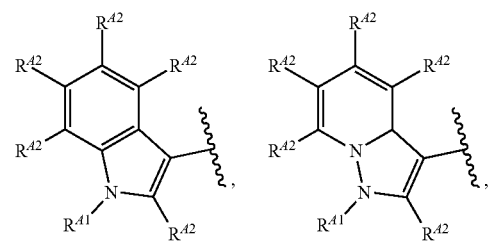

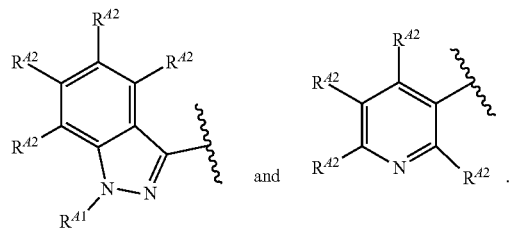

In certain embodiments of ring A, each R$^{41}$ is independently selected from hydrogen, or C$_{1-6}$ alkyl. In certain embodiments, all instances of R$^{41}$ are hydrogen.

In certain embodiments, each R$^{42}$ is independently selected from hydrogen, halogen, and optionally substituted C$_1$-C$_6$ alkyl. In one aspect of these embodiments, all instances of R$^{42}$ are hydrogen.

In certain embodiments, ring A is selected from:

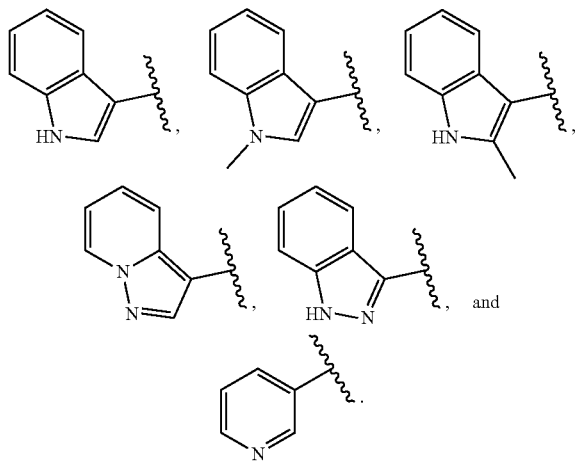

In certain embodiments, ring A is additionally selected from

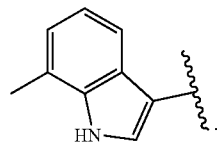 [SMILES: *c1c[nH]c2c(C)cccc12]

In certain embodiments, each X is N.
In certain embodiments, W is N.
In other embodiments, W is C($R^{1a}$).
In certain embodiments, $R^{1a}$ is selected from selected from hydrogen, halo, —OH, —$C_1$-$C_3$ alkyl, halo-substituted —$C_1$-$C_3$ alkyl, —O—$C_1$-$C_3$ alkyl, halo-substituted —O—$C_1$-$C_3$ alkyl, —CN, —$NH_2$, —NH($C_1$-$C_3$ alkyl), —N($C_1$-$C_3$ alkyl)$_2$, and $C_3$-$C_6$ cycloalkyl. In one aspect of these embodiments, $R^{1a}$ selected from hydrogen, halo, —CN and $C_3$-$C_6$ cycloalkyl. In an alternate aspect of these embodiments, $R^{1a}$ selected from hydrogen, halo, —CN, halo-substituted —$C_1$-$C_3$ alkyl and $C_3$-$C_6$ cycloalkyl. In an even more specific aspect of these embodiments, $R^{1a}$ is selected from hydrogen, chloro, fluoro, —CN and cyclopropyl. In another even more specific aspect of these embodiments, $R^{1a}$ is selected from hydrogen, chloro, fluoro, —CN, —$CF_3$ and cyclopropyl cyclopropyl.
In certain embodiments, $R^{1b}$ is selected from selected from hydrogen, halo, —OH, —$C_1$-$C_3$ alkyl, halo-substituted —$C_1$-$C_3$ alkyl, —O—$C_1$-$C_3$ alkyl, halo-substituted —O—$C_1$-$C_3$ alkyl, —CN, —$NH_2$, —NH($C_1$-$C_3$ alkyl), and —N($C_1$-$C_3$ alkyl)$_2$. In one aspect of these embodiments, $R^{1b}$ is hydrogen.
In certain embodiments, $R^2$ is selected from —NH—; —N($C_1$-$C_3$ alkyl)-; —NH—$CH_2$—*; and $C_1$-$C_2$ alkylene optionally substituted with 1 to 4 substituents independently selected from halo, —OH, —$C_1$-$C_3$ alkyl, halo-substituted —$C_1$-$C_3$ alkyl, —O—$C_1$-$C_3$ alkyl, halo-substituted —O—$C_1$-$C_3$ alkyl, —CN, —$NH_2$, —NH($C_1$-$C_3$ alkyl), —N($C_1$-$C_3$ alkyl)$_2$, wherein "*" represents a portion of $R^2$ bound to a cyclohexyl ring. In a more specific aspect of these embodiments, $R^2$ is —NH—.
In certain embodiments, $R^3$ is attached meta to $R^2$, e.g., a compound of Formula (Ia):

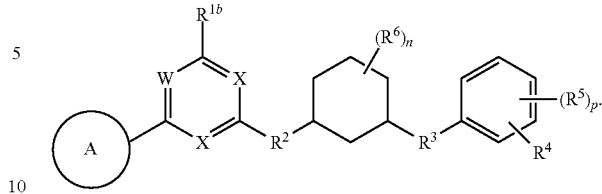

(Ia)

In certain embodiments, $R^3$ is selected from †—NH—C(O)—, †—C(O)—NH—, †—NH—S(O)$_2$—, †—NH—CH(CF$_3$)—, and —N(CH$_3$)—CH$_2$—, wherein "†" represents a portion of $R^3$ bound to a cyclohexyl ring.
In some embodiments, $R^4$ is selected from hydrogen, —($C_1$-$C_4$ alkyl), —C(O)—($C_1$-$C_4$ alkylene)-$NH_2$, —($C_1$-$C_4$ alkylene)-$NH_2$, —$NH_2$, —NH—C(O)—($C_1$-$C_4$ alkylene)-$NH_2$, —NH—C(O)—($C_1$-$C_4$ alkylene)-NH—($C_1$-$C_4$ alkyl), —NH—C(O)—($C_1$-$C_4$ alkylene)-N—($C_1$-$C_4$ alkyl)$_2$, —NH—C(O)—C(O)—($C_0$-$C_4$ alkylene)-$NH_2$, —NH—C(O)—C(O)—($C_0$-$C_4$ alkylene)-NH($C_1$-$C_4$ alkyl), —NH—C(O)—C(O)—($C_0$-$C_4$ alkylene)-N($C_1$-$C_4$ alkyl)$_2$, and —NH—C(O)—($C_1$-$C_4$ alkyl). In one aspect of these embodiments, $R^4$ is selected from —$NH_2$, —NH—C(O)—($CH_2$)$_3$—N($CH_3$)$_2$, —NH—C(O)—$CH_2$—CH(OH)—$CH_2$—N($CH_3$)$_2$, —NH—$CH_3$, and —NH—C(O)—C(O)—$NH_2$.

In some embodiments, $R^5$ is absent (i.e., p=0).
In some embodiments, p=1 or 2, and each $R^5$ is independently selected from halo and saturated heterocyclyl. In a more specific aspect of these embodiments, each $R^5$ is independently selected from fluoro, chloro and morpholin-4-yl.
In some embodiments, $R^6$ is absent (i.e., n=0).
In some embodiments, n=1 or 2 and each $R^6$ is independently selected from —OH, halo, and $C_1$-$C_3$ alkyl, or two or three $R^6$ bound to separate carbon atoms are taken together with the carbon atoms to form a second cycloalkyl ring fused to the cyclohexyl ring depicted in Formula I, and wherein the second cycloalkyl ring is optionally substituted and wherein a substituent on the second cycloalkyl ring is optionally taken together with a third $R^6$ to form a third cycloalkyl ring fused to both the second cycloalkyl ring and the cyclohexyl ring. In a more specific aspect of these embodiments, each $R^6$ is independently selected from —OH, fluoro, and methyl, or two or three $R^6$ are taken together with the carbon atoms in the cyclohexyl ring depicted in Formula I to form:

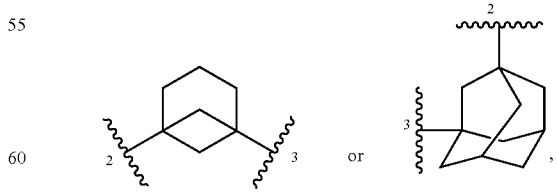

wherein "2" represents a portion of the ring bound to $R^2$, and "3" represents a portion of the ring bound to $R^3$.

In certain embodiments, a compound of Formula (I) has the structure of Formula (Ib):

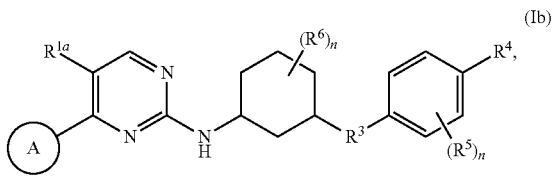

(Ib)

wherein:
ring A is selected from

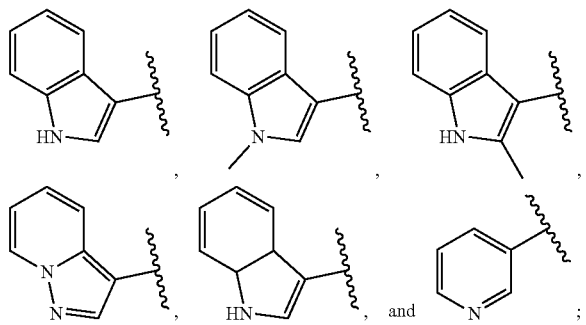

, and $R^{1a}$ is selected from hydrogen, chloro, fluoro, —CN and cyclopropyl;

$R^3$ is selected from †—NH—C(O)—, †—C(O)—NH—, †—NH—S(O)$_2$—, †—NH—CH(CF$_3$)—, and —N(CH$_3$)—CH$_2$—, wherein "†" represents a portion of $R^3$ bound to a cyclohexyl ring;

$R^4$ is selected from —NH$_2$, —NH—C(O)—(CH$_2$)$_3$—N(CH$_3$)$_2$, and —NH—C(O)—C(O)—NH$_2$;

$R^5$ is absent, or each $R^5$ is independently selected from fluoro and morpholin-4-yl;

$R^6$ is absent, or each $R^6$ is independently selected from —OH, halo, and C$_1$-C$_3$ alkyl; or two or three $R^6$ bound to separate carbon atoms are taken together with the carbon atoms to form:

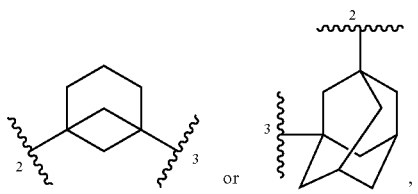 [SMILES: *C12CCCC(*)(C1)C2 ; *C12CC3CC(C1)CC(*)(C3)C2]

wherein "2" represents a portion of the ring bound to $R^2$, and "3" represents a portion of the ring bound to $R^3$.

In some embodiments of Formula Ib, ring A is additionally selected from

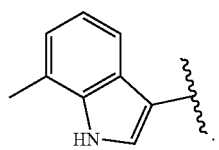 [SMILES: *c1c[nH]c2c(C)cccc12]

In some embodiments of Formula Ib, $R^4$ is additionally selected from —NH—C(O)—CH$_2$—CH(OH)—CH$_2$—N(CH$_3$)$_2$, and —NH—CH$_3$.

In some embodiments of Formula Ib, $R^5$ is additionally selected from chloro.

Although, as indicated above, various embodiments and aspects thereof for a variable in Formula (I), (Ia), or (M) may be selected from a group of chemical moieties, the invention also encompasses as further embodiments and aspects thereof situations where such variable is: a) selected from any subset of chemical moieties in such a group; and b) any single member of such a group.

Although various embodiments and aspects thereof are set forth (or implied, as discussed in the preceding paragraph) individually for each variable in Formula (I), (Ia), or (n) above, the invention encompasses all possible combinations of the different embodiments and aspects for each of the variables in Formula (I), (Ia), or (Ib).

In certain embodiments, the compound of Formula (I) is selected from the group consisting of any one of the compounds in the table of FIGS. 1A-1C and pharmaceutically acceptable salts, solvates, hydrates, tautomers, stereoisomers, and isotopically labeled derivatives thereof.

Pharmaceutical Compositions, Kits, and Administration

The present invention provides pharmaceutical compositions comprising a compound of Formula (I), (Ia), or (Ib), e.g., a compound of Formula (I), (Ia), or (Ib), or a pharmaceutically acceptable salt, solvate, hydrate, tautomer, stereoisomer, or isotopically labeled derivative thereof, as described herein, and optionally a pharmaceutically acceptable excipient. In certain embodiments, the pharmaceutical composition of the invention comprises a compound of Formula (I), (Ia), or (Ib), or a pharmaceutically acceptable salt thereof, and optionally a pharmaceutically acceptable excipient. In certain embodiments, the compound of Formula (I), (Ia), or (Ib), or a pharmaceutically acceptable salt, solvate, hydrate, tautomer, stereoisomer, or isotopically labeled derivative thereof, is provided in an effective amount in the pharmaceutical composition. In certain embodiments, the effective amount is a therapeutically effective amount. In certain embodiments, the effective amount is a prophylactically effective amount.

Pharmaceutical compositions described herein can be prepared by any method known in the art of pharmacology. In general, such preparatory methods include the steps of bringing the compound of Formula (I), (Ia), or (Ib) (the "active ingredient") into association with a carrier and/or one or more other accessory ingredients, and then, if necessary and/or desirable, shaping and/or packaging the product into a desired single- or multi-dose unit.

Pharmaceutical compositions can be prepared, packaged, and/or sold in bulk, as a single unit dose, and/or as a plurality of single unit doses. As used herein, a "unit dose" is a discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

Relative amounts of the active ingredient, the pharmaceutically acceptable excipient, and/or any additional ingredients in a pharmaceutical composition of the invention will vary, depending upon the identity, size, and/or condition of the subject treated and further depending upon the route by which the composition is to be administered. By way of example, the composition may comprise between 0.1% and 100% (w/w) active ingredient.

The term "pharmaceutically acceptable excipient" refers to a non-toxic carrier, adjuvant, diluent, or vehicle that does not destroy the pharmacological activity of the compound with which it is formulated. Pharmaceutically acceptable excipients useful in the manufacture of the pharmaceutical compositions of the invention are any of those that are well known in the art of pharmaceutical formulation and include inert diluents, dispersing and/or granulating agents, surface active agents and/or emulsifiers, disintegrating agents, binding agents, preservatives, buffering agents, lubricating agents, and/or oils. Pharmaceutically acceptable excipients useful in the manufacture of the pharmaceutical compositions of the invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

Compositions of the present invention may be administered orally, parenterally (Including subcutaneous, intramuscular, intravenous and intradermal), by inhalation spray, topically, rectally, nasally, buccally, vaginally or via an implanted reservoir. In some embodiments, provided compounds or compositions are administrable intravenously and/or orally.

The term "parenteral" as used herein includes subcutaneous, intravenous, intramuscular, intraocular, intravitreal, intra-articular, intra-synovial, intrasternal, intrathecal, intrahepatic, intraperitoneal intralesional and intracranial injection or infusion techniques. Preferably, the compositions are administered orally, subcutaneously, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

Pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added. In some embodiments, a provided oral formulation is formulated for immediate release or sustained/delayed release. In some embodiments, the composition is suitable for buccal or sublingual administration, including tablets, lozenges and pastilles. A provided compound can also be in micro-encapsulated form.

Alternatively, pharmaceutically acceptable compositions of this invention may be administered in the form of suppositories for rectal administration. Pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For ophthalmic use, provided pharmaceutically acceptable compositions may be formulated as micronized suspensions or in an ointment such as petrolatum.

Pharmaceutically acceptable compositions of this invention may also be administered by nasal aerosol or inhalation.

In order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation.

Compounds provided herein are typically formulated in dosage unit form, e.g., single unit dosage form, for ease of administration and uniformity of dosage. It will be understood, however, that the total daily usage of the compositions of the present invention will be decided by the attending physician within the scope of sound medical judgment. The specific therapeutically effective dose level for any particular subject or organism will depend upon a variety of factors including the disease being treated and the severity of the disorder; the activity of the specific active ingredient employed; the specific composition employed; the age, body weight, general health, sex and diet of the subject; the time of administration, route of administration, and rate of excretion of the specific active ingredient employed; the duration of the treatment; drugs used in combination or coincidental with the specific active ingredient employed; and like factors well known in the medical arts.

The exact amount of a compound required to achieve an effective amount will vary from subject to subject, depending, for example, on species, age, and general condition of a subject, severity of the side effects or disorder, identity of the particular compound(s), mode of administration, and the like. The desired dosage can be delivered three times a day, two times a day, once a day, every other day, every third day, every week, every two weeks, every three weeks, or every four weeks. In certain embodiments, the desired dosage can be delivered using multiple administrations (e.g., two, three, four, five, six, seven, eight, nine, ten, eleven, twelve, thirteen, fourteen, or more administrations).

In certain embodiments, an effective amount of a compound for administration one or more times a day to a 70 kg adult human may comprise about 0.0001 mg to about 3000 mg, about 0.0001 mg to about 2000 mg, about 0.0001 mg to about 1000 mg, about 0.001 mg to about 1000 mg, about 0.01 mg to about 1000 mg, about 0.1 mg to about 1000 mg, about 1 mg to about 1000 mg, about 1 mg to about 100 mg, about 10 mg to about 1000 mg, or about 100 mg to about 1000 mg, of a compound per unit dosage form.

In certain embodiments, the compounds of Formula (I), (Ia), or (Ib) may be at dosage levels sufficient to deliver from about 0.001 mg/kg to about 100 mg/kg, from about 0.01 mg/kg to about 50 mg/kg, preferably from about 0.1 mg/kg to about 40 mg/kg, preferably from about 0.5 mg/kg to about 30 mg/kg, from about 0.01 mg/kg to about 10 mg/kg, from about 0.1 mg/kg to about 10 mg/kg, and more preferably from about 1 mg/kg to about 25 mg/kg, of subject body weight per day, one or more times a day, to obtain the desired therapeutic effect.

It will be appreciated that dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult.

It will be also appreciated that a compound or composition, as described herein, can be administered in combination with one or more additional pharmaceutical agents. The compounds or compositions can be administered in combination with additional pharmaceutical agents that improve their bioavailability, reduce and/or modify their metabolism, inhibit their excretion, and/or modify their distribution within the body. It will also be appreciated that the therapy employed may achieve a desired effect for the same disorder, and/or it may achieve different effects.

The compound or composition can be administered concurrently with, prior to, or subsequent to, one or more additional pharmaceutical agents, which may be useful as, e.g., combination therapies. Pharmaceutical agents include therapeutically active agents. Pharmaceutical agents also include prophylactically active agents. Each additional pharmaceutical agent may be administered at a dose and/or on a time schedule determined for that pharmaceutical agent. The additional pharmaceutical agents may also be administered together with each other and/or with the compound or composition described herein in a single dose or administered separately in different doses. The particular combination to employ in a regimen will take into account compatibility of the inventive compound with the additional pharmaceutical agents and/or the desired therapeutic and/or prophylactic effect to be achieved. In general, it is expected that the additional pharmaceutical agents utilized in combination be utilized at levels that do not exceed the levels at which they are utilized individually. In some embodiments, the levels utilized in combination will be lower than those utilized individually.

Exemplary additional pharmaceutical agents include, but are not limited to, anti-proliferative agents, anti-cancer agents, anti-diabetic agents, anti-inflammatory agents, immunosuppressant agents, and a pain-relieving agent. Pharmaceutical agents include small organic molecules such as drug compounds (e.g., compounds approved by the U.S. Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins, and cells.

Also encompassed by the invention are kits (e.g., pharmaceutical packs). The inventive kits may be useful for preventing and/or treating a proliferative disease (e.g., cancer (e.g., leukemia, melanoma, multiple myeloma), benign neoplasm, angiogenesis, inflammatory disease, autoinflammatory disease, or autoimmune disease). The kits provided may comprise an inventive pharmaceutical composition or compound and a container (e.g., a vial, ampule, bottle, syringe, and/or dispenser package, or other suitable container). In some embodiments, provided kits may optionally further include a second container comprising a pharmaceutical excipient for dilution or suspension of an inventive pharmaceutical composition or compound. In some embodiments, the inventive pharmaceutical composition or compound provided in the container and the second container are combined to form one unit dosage form.

Thus, in one aspect, provided are kits including a first container comprising a compound described herein, or a pharmaceutically acceptable salt, solvate, hydrate, tautomer, stereoisomer, and isotopically labeled derivative, or a pharmaceutical composition thereof. In certain embodiments, the kit of the invention includes a first container comprising a compound described herein, or a pharmaceutically acceptable salt thereof, or a pharmaceutical composition thereof. In certain embodiments, the kits are useful in preventing and/or treating a proliferative disease in a subject. In certain embodiments, the kits further include instructions for administering the compound, or a pharmaceutically acceptable salt, solvate, hydrate, tautomer, stereoisomer, isotopically and labeled derivative thereof, or a pharmaceutical composition thereof, to a subject to prevent and/or treat a proliferative disease.

Methods of Treatment and Uses

The present invention also provides methods for the treatment or prevention of a proliferative disease (e.g., cancer, benign neoplasm, angiogenesis, inflammatory disease, autoinflammatory disease, or autoimmune disease) or an infectious disease (e.g., a viral disease) in a subject. Such methods comprise the step of administering to the subject in need thereof an effective amount of a compound of Formula (I), (Ia), or (Ib), or a pharmaceutically acceptable salt, solvate, hydrate, tautomer, stereoisomer, or isotopically labeled derivative thereof, or a pharmaceutical composition thereof. In certain embodiments, the methods described herein include administering to a subject an effective amount of a compound of Formula (I), (Ia), or (Ib), or a pharmaceutically acceptable salt thereof, or a pharmaceutical composition thereof.

In certain embodiments, the subject being treated is a mammal. In certain embodiments, the subject is a human. In certain embodiments, the subject is a domesticated animal, such as a dog, cat, cow, pig, horse, sheep, or goat. In certain embodiments, the subject is a companion animal such as a dog or cat. In certain embodiments, the subject is a livestock animal such as a cow, pig, horse, sheep, or goat. In certain embodiments, the subject is a zoo animal. In another embodiment, the subject is a research animal such as a rodent, dog, or non-human primate. In certain embodiments, the subject is a non-human transgenic animal such as a transgenic mouse or transgenic pig.

The proliferative disease to be treated or prevented using the compounds of Formula (I), (Ia), or (Ib) will typically be associated with aberrant activity of CDK7. Aberrant activity of CDK7 may be an elevated and/or an inappropriate (e.g., abnormal) activity of CDK7. In certain embodiments, CDK7 is not overexpressed, and the activity of CDK7 is elevated and/or inappropriate. In certain other embodiments, CDK7 is overexpressed, and the activity of CDK7 is elevated and/or inappropriate. The compounds of Formula (I), (Ia), or (Ib), and pharmaceutically acceptable salts, solvates, hydrates, tautomers, stereoisomers, isotopically labeled derivatives, and compositions thereof, may inhibit the activity of CDK7 and be useful in treating and/or preventing proliferative diseases.

In other embodiments, the proliferative disease to be treated or prevented using the compounds of Formula (I), (Ia), or (Ib) will typically be associated with aberrant activity of other CDK family members. In some embodiments, the other CDK family members are CDK12 and/or CDK13. Aberrant activity of CDK12 and/or CDK13 may be an elevated and/or an inappropriate (e.g., abnormal) activity of CDK12 and/or CDK13. In certain embodiments, CDK12 and/or CDK13 is not overexpressed, and the activity of CDK12 and/or CDK13 is elevated and/or inappropriate. In certain other embodiments, CDK12 and/or CDK13 is overexpressed, and the activity of CDK12 and/or CDK13 is elevated and/or inappropriate. The compounds of Formula (I), (Ia), or (Ib), and pharmaceutically acceptable salts, solvates, hydrates, tautomers, stereoisomers, isotopically labeled derivatives, and compositions thereof, may inhibit the activity of CDK12 and/or CDK13 and be useful in treating and/or preventing proliferative diseases.

A proliferative disease may also be associated with inhibition of apoptosis of a cell in a biological sample or subject. All types of biological samples described herein or known in the art are contemplated as being within the scope of the invention. Inhibition of the activity of CDK7 is expected to cause cytotoxicity via induction of apoptosis. The compounds of Formula (I), (Ia), or (Ib), and pharmaceutically acceptable salts, solvates, hydrates, tautomers, stereoisomers, isotopically labeled derivatives, and compositions thereof, may induce apoptosis, and therefore, be useful in treating and/or preventing proliferative diseases.

In certain embodiments, the proliferative disease to be treated or prevented using the compounds of Formula (I), (Ia), or (Ib) is cancer. All types of cancers disclosed herein or known in the art are contemplated as being within the scope of the invention. In certain embodiments, the proliferative disease is a cancer associated with dependence on BCL-2 anti-apoptotic proteins (e.g., MCL-1 and/or XIAP). In certain embodiments, the proliferative disease is a cancer associated with overexpression of MYC (a gene that codes for a transcription factor). In certain embodiments, the proliferative disease is a hematological malignancy. In certain embodiments, the proliferative disease is a blood cancer. In certain embodiments, the proliferative disease is leukemia. In certain embodiments, the proliferative disease is chronic lymphocytic leukemia (CLL). In certain embodiments, the proliferative disease is acute lymphoblastic leukemia (ALL). In certain embodiments, the proliferative disease is T-cell acute lymphoblastic leukemia (T-ALL). In certain embodiments, the proliferative disease is chronic myelogenous leukemia (CML). In certain embodiments, the proliferative disease is acute myelogenous leukemia (AML). In certain embodiments, the proliferative disease is lymphoma. In certain embodiments, the proliferative disease is melanoma. In certain embodiments, the proliferative disease is multiple myeloma. In certain embodiments, the proliferative disease is a bone cancer. In certain embodiments, the proliferative disease is osteosarcoma. In some embodiments, the proliferative disease is Ewing's sarcoma. In some embodiments, the proliferative disease is triple-negative breast cancer (TNBC). In some embodiments, the proliferative disease is a brain cancer. In some embodiments, the proliferative disease is neuroblastoma. In some embodiments, the proliferative disease is a lung cancer. In some embodiments, the proliferative disease is small cell lung cancer (SCLC). In some embodiments, the proliferative disease is large cell lung cancer. In some embodiments, the proliferative disease is a benign neoplasm. All types of benign neoplasms disclosed herein or known in the art are contemplated as being within the scope of the invention.

In some embodiments, the proliferative disease is associated with angiogenesis. All types of angiogenesis disclosed herein or known in the art are contemplated as being within the scope of the invention.

In certain embodiments, the proliferative disease is an inflammatory disease. All types of inflammatory diseases disclosed herein or known in the art are contemplated as being within the scope of the invention. In certain embodiments, the inflammatory disease is rheumatoid arthritis. In some embodiments, the proliferative disease is an autoinflammatory disease. All types of autoinflammatory diseases disclosed herein or known in the art are contemplated as being within the scope of the invention. In some embodiments, the proliferative disease is an autoimmune disease. All types of autoimmune diseases disclosed herein or known in the art are contemplated as being within the scope of the invention.

The cell described herein may be an abnormal cell. The cell may be in vitro or in vivo. In certain embodiments, the cell is a proliferative cell. In certain embodiments, the cell is a blood cell. In certain embodiments, the cell is a lymphocyte. In certain embodiments, the cell is a cancer cell. In certain embodiments, the cell is a leukemia cell. In certain embodiments, the cell is a CLL cell. In certain embodiments, the cell is a melanoma cell. In certain embodiments, the cell is a multiple myeloma cell. In certain embodiments, the cell is a benign neoplastic cell. In certain embodiments, the cell is an endothelial cell. In certain embodiments, the cell is an immune cell.

In another aspect, the present invention provides methods of down-regulating the expression of a CDK (e.g., CDK7, CDK1, CDK2, CDK5, CDK8, CDK9, CDK12, or CDK13) in a biological sample or subject. In certain embodiments, the present invention provides methods of down-regulating the expression of CDK7 in a biological sample or subject. In another aspect, the present invention provides methods of down-regulating the expression of Jurkat, IRAK1, JNK1, JNK2, or MLK3 in a biological sample or subject.

In certain embodiments, the methods described herein comprise the additional step of administering one or more additional pharmaceutical agents in combination with the compound of Formula (I), (Ia), or (Ib), a pharmaceutically acceptable salt thereof, or compositions comprising such compound or pharmaceutically acceptable salt thereof. Such additional pharmaceutical agents include, but are not limited to, anti-proliferative agents, anti-cancer agents, anti-diabetic agents, anti-inflammatory agents, immunosuppressant agents, and a pain-relieving agent. The additional pharmaceutical agent(s) may synergistically augment inhibition of CDK7, CDK12, or CDK13 induced by the inventive compounds or compositions of this invention in the biological sample or subject. In certain embodiments, the additional pharmaceutical agent is flavopiridol, triptolide, SNS-032 (BMS-387032), PHA-767491, PHA-793887, BS-181, (S)—CR8, (R)—CR8, or NU6140. In certain embodiments, the additional pharmaceutical agent is an inhibitor of a mitogen-activated protein kinase (MAPK). In certain embodiments, the additional pharmaceutical agent is an inhibitor of a glycogen synthase kinase 3 (GSK3). In certain embodiments, the additional pharmaceutical agent is an inhibitor of an AGC kinase. In certain embodiments, the additional pharmaceutical agent is an inhibitor of a CaM kinase. In certain embodiments, the additional pharmaceutical agent is an inhibitor of a casein kinase 1. In certain embodiments, the additional pharmaceutical agent is an inhibitor of a STE kinase. In certain embodiments, the additional pharmaceutical agent is an inhibitor of a tyrosine kinase. Thus, the combination of the inventive compounds or compositions and the additional pharmaceutical agent(s) may be useful in treating proliferative diseases resistant to a treatment using the additional pharmaceutical agent(s) without the inventive compounds or compositions.

In yet another aspect, the present invention provides the compounds of Formula (I), (Ia), or (Ib), and pharmaceutically acceptable salts, solvates, hydrates, tautomers, stereoisomers, isotopically labeled derivatives, and compositions thereof, for use in the treatment of a proliferative disease in a subject. In certain embodiments, provided by the invention are the compounds described herein, and pharmaceutically acceptable salts and compositions thereof, for use in the treatment of a proliferative disease in a subject. In certain embodiments, provided by the invention are the compounds described herein, and pharmaceutically acceptable salts and compositions thereof, for use in inhibiting cell growth. In certain embodiments, provided by the invention are the compounds described herein, and pharmaceutically acceptable salts and compositions thereof, for use in inducing apoptosis in a cell. In certain embodiments, provided by the invention are the compounds described herein, and pharmaceutically acceptable salts and compositions thereof, for use in inhibiting transcription.

EXAMPLES

In order that the invention described herein may be more fully understood, the following examples are set forth. The synthetic and biological examples described in this application are offered to illustrate the compounds, pharmaceutical compositions, and methods provided herein and are not to be construed in any way as limiting their scope.

The compounds provided herein can be prepared from readily available starting materials using modifications to the specific synthesis protocols set forth below that would be well known to those of skill in the art. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvents used, but such conditions can be determined by those skilled in the art by routine optimization procedures.

Additionally, as will be apparent to those skilled in the art, conventional protecting groups may be necessary to prevent certain functional groups from undergoing undesired reactions. The choice of a suitable protecting group for a particular functional group as well as suitable conditions for protection and deprotection are well known in the art. For example, numerous protecting groups, and their introduction and removal, are described in Greene et al., *Protecting Groups in Organic Synthesis*, Second Edition, Wiley, New York, 1991, and references cited therein.

| ABBREVIATIONS | |
|---|---|
| Ac | acetyl |
| ACN | acetonitrile |
| aq. | aqueous |
| atm | atmospheres |
| Boc | tert-butoxy carbonyl |
| Boc$_2$O | Di-t-butyl dicarbonate |
| Bn | Benzyl |
| DCC | N,N'-Dicyclohexylcarbodiimide |
| DCM | Dichloromethane |
| DCE | Dichloroethene |
| DIAD | Diisopropyl azodicarboxylate |
| DIPEA | N,N-Diisopropyl ethylamine |
| DMA | Dimethylacetamide |
| DMF | Dimethylformamide |
| DMSO | Dimethylsulfoxide |
| DPPA | Diphenoxyphosphoryl azide |
| EDTA | Ethylenediamine tetraacetic acid |
| eq(s). | equivalent(s) |
| EtOAc | Ethyl acetate |
| Et | Ethyl |
| EtOH | Ethanol |
| Et$_3$N | Triethylamine |
| g | gram(s) |
| h | hour(s) |
| HATU | (Dimethylamino)-N,N-dimethyl(3H-[1,2,3]triazolo[4,5-b]pyridin-3-yloxy)methaniminium hexafluorophosphate |
| HBTU | O-Benzotriazole-N,N,N',N'-tetramethyl-uronium-hexafluoro-phosphate |
| Hex | Hexanes |
| HOBt | 1-Hydroxybenzotriazole |
| HPLC | High pressure liquid chromatography |
| IPA | Isopropanol |
| LCMS; LC-MS | liquid chromatography mass spectrometry |
| Me-DAST | Dimethylaminosulfurtrifluoride |
| MeOH | methanol |
| mg | milligram(s) |
| min | Minute(s) |
| mL; ml | milliliter(s) |
| MS | mass spectrometry |
| mW | microwave |
| NMe | N-methyl |
| NMP | N-Methyl-2-pyrrolidone |
| NMR | Nuclear magnetic resonance |
| Pd$_2$dba$_3$ | Tris(dibenzylideneacetone)dipalladium(0) |
| Ph | phenyl |
| pyr | Pyridine |
| r.t.; rt; RT | Room temperature |
| S., sat. | saturated |
| TEA | Triethylamine |
| TFA | Trifluoroacetic acid |
| THF | Tetrahydrofuran |
| TLC | Thin layer chromatography |
| X-Phos | 2-Dicyclohexylphosphino-2',4',6'-triisopropylbiphenyl |

Example 1. 4-amino-N-(3-(5-chloro-4-(1H-indol-3-yl)pyrimidin-2-ylamino)tricyclo[3.3.1.1$^{3,7}$]decanyl)benzamide (Compound 100)

Dibenzyl tricyclo[3.3.1.1$^{3,7}$]decane-1,3-diyldicarbamate

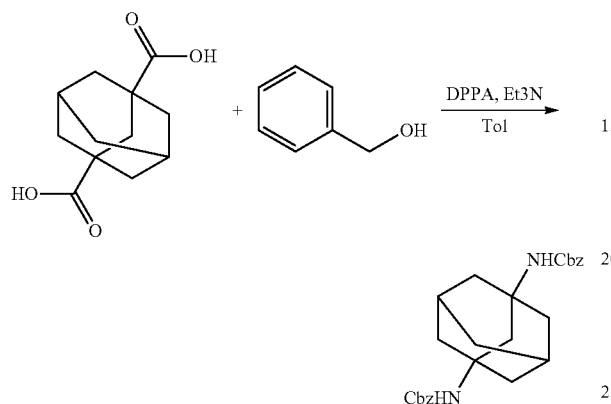

A solution of tricyclo[3.3.1.1$^{3,7}$]decane-1,3-dicarboxylic acid (500 mg, 2.230 mmol) in toluene (9 mL) was treated with Et$_3$N (0.68 mL, 4.91 mmol) and DPPA (0.96 mL, 4.46 mmol) and heated at 110° C. for 1 h. The mixture was cooled down to 80° C. and treated with benzyl alcohol (0.580 mL, 5.574 mmol) and Et$_3$N (0.68 mL, 4.91 mmol). The resulting mixture was heated at 80° C. for 20 h. The cooled mixture was then diluted with EtOAc (50 mL) and H$_2$O (50 mL). The layers were separated and the aqueous layer was extracted with EtOAc (3×50 mL). The combined organics layers were washed with brine (50 mL), filtered and evaporated to dryness. The residue was purified by SiO$_2$ chromatography (Hex/EtOAc 0 to 70% gradient) to afford the title compound (800 mg, 1.97 mmol, 88%) as clear oil.

Tricyclo[3.3.1.1$^{3,7}$]decane-1,3-diamine

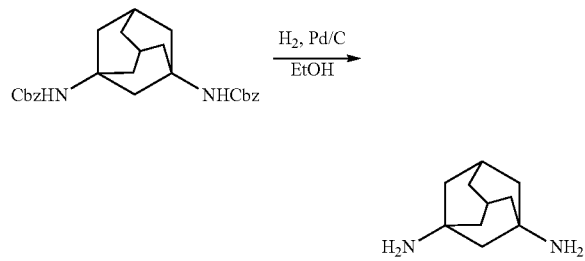

A degassed solution of dibenzyl tricyclo[3.3.1.1$^{3,7}$]decane-1,3-diyldicarbamate (773 mg, 0.223 mmol) in EtOH (45 mL) was treated with 10% w/w Pd/C (356 mg). The mixture was stirred 18 h under hydrogen (1 atm) before filtration over a pad of celite (EtOH). The filtrate was evaporated under reduced pressure to afford the title compound (348 mg, 2.10 mmol, 94%) as a colorless oil which was used in the next step without further purification.

N1-(5-chloro-4-(1-(phenylsulfonyl)-1H-indol-3-yl)pyrimidin-2-yl)tricyclo[3.3.1.1$^{3,7}$]decane-1,3-diamine

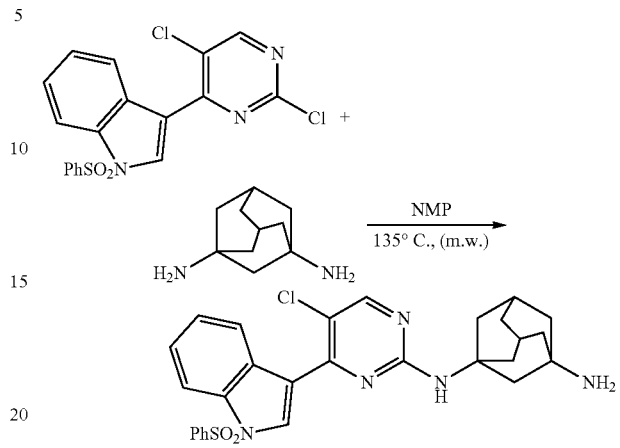

A solution of 3-(2,5-dichloropyrimidin-4-yl)-1-(phenylsulfonyl)-1H-indole (450 mg, 1.11 mmol), tricyclo[3.3.1.1$^{3,7}$]decane-1,3-diamine (278 mg, 1.67 mmol) and DIPEA (0.29 mL, 1.67 mmol) in NMP (11 mL) was heated at 135° C. (microwave) for 75 min. The cooled mixture was diluted with EtOAc (50 mL), washed with H$_2$O (15 mL), brine (15 mL), dried over MgSO$_4$, filtered and evaporated to dryness. The residue was purified by C$_{18}$ chromatography (H$_2$O/ACN+0.1% HCO$_2$H 5 to 100% gradient) to afford the title compound (168 mg, 0.315 mmol, 28%) as a light orange oil.

tert-butyl 4-(3-(5-chloro-4-(1-(phenylsulfonyl)-1H-indol-3-yl)pyrimidin-2-ylamino)tricyclo[3.3.1.1$^{3,7}$]decanylcarbamoyl)phenylcarbamate

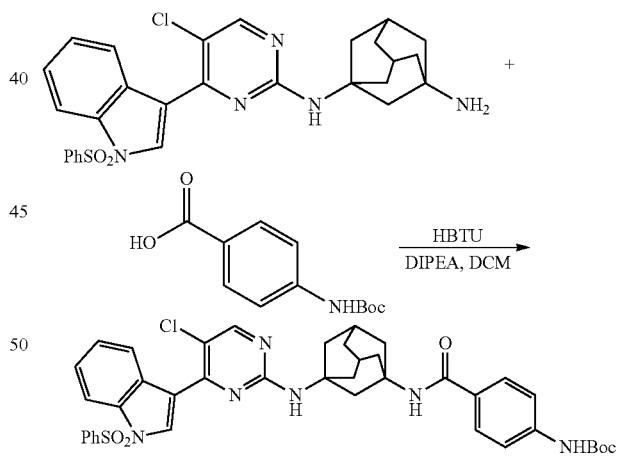

A solution of N1-(5-chloro-4-(1-(phenylsulfonyl)-1H-indol-3-yl)pyrimidin-2-yl)tricyclo[3.3.1.1$^{3,7}$]decane-1,3-diamine (193 mg, 0.360 mmol) and 4-(tert-butoxycarbonylamino)benzoic acid (86 mg, 0.360 mmol) in 4/1 DCM/DMF (5 mL) was treated with HBTU (274 mg, 0.720 mmol) and DIPEA (0.19 mL, 1.08 mmol). The resulting mixture was stirred 18 h at rt and diluted with DCM (20 mL) and saturated NaHCO$_3$ (10 mL). The layers were separated and the organic layer was extracted with DCM (3×10 mL). The combined organic layers were washed with brine (10 mL), dried over MgSO$_4$, filtered, and evaporated to dryness. The residue was purified by SiO$_2$ chromatography (DCM/EtOAc 0 to 50% gradient) to afford the title compound (70 mg, 0.093 mmol, 26%) as a light yellow oil.

4-amino-N-(3-(5-chloro-4-(1-(phenylsulfonyl)-1H-indol-3-yl)pyrimidin-2-ylamino)tricyclo[3.3.1.1³,⁷]decanyl)benzamide.TFA

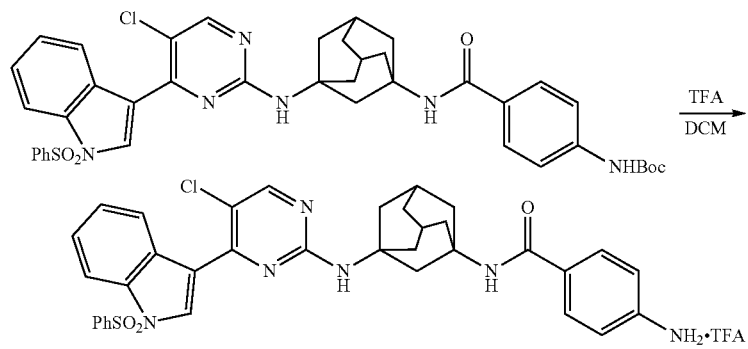

A solution of tert-butyl 4-(3-(5-chloro-4-(1-(phenylsulfonyl)-1H-indol-3-yl)pyrimidin-2-ylamino)tricyclo[3.3.1.1³,⁷]decanylcarbamoyl)phenylcarbamate (70 mg, 0.093 mmol) in DCM (2 mL) was treated with TFA (1.1 mL, 13.94 mmol). The resulting mixture was stirred 1 h at rt before being evaporated to dryness. The residue was dried under high vacuum to afford the title compound (71 mg, 0.093 mmol, 100%) as a light yellow oil which was used in the next step without further purification.

4-amino-N-(3-(5-chloro-4-(1H-indol-3-yl)pyrimidin-2-ylamino)tricyclo[3.3.1.1³,⁷]decanxyl)benzamide

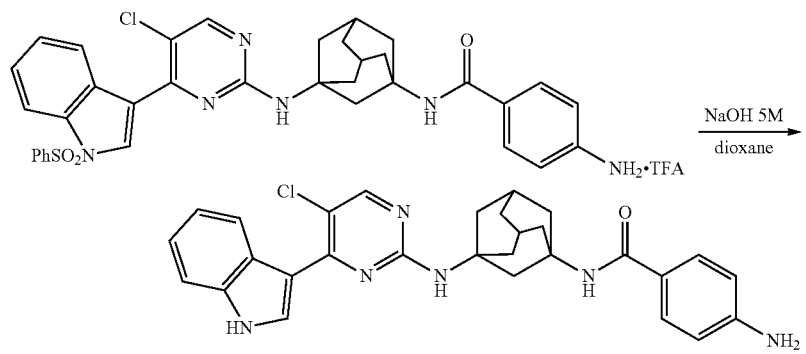

A solution of 4-amino-N-(3-(5-chloro-4-(1-(phenylsulfonyl)-1H-indol-3-yl)pyrimidin-2-ylamino)tricyclo[3.3.1.1³,⁷]decanyl)benzamide.TFA (47 mg, 0.072 mmol) in dioxane (1.5 mL) was treated with a 5M aqueous solution of NaOH (0.29 mL, 1.44 mmol) and heated 70° C. for 4 h. The cooled mixture was treated with a 1M aqueous solution of HCl until pH=7, extracted with EtOAc (3×10 mL), dried over MgSO₄, filtered and evaporated under reduced pressure. The residue was purified by C₁₈ chromatography (H₂O/ACN+0.1% HCO₂H 5 to 100% gradient) to afford the title compound (9.5 mg, 0.019 mmol, 26%) as a white solid.

Example 2. (+/−)-4-amino-N-(3-(5-chloro-4-(1H-indol-3-yl)pyrimidin-2-ylamino)-5-hydroxycyclohexyl)benzamide (Compound 101)

(+/−)-5-(tert-butyldimethylsilyloxy)cyclohexane-1,3-diamine

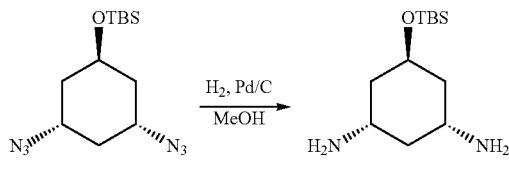 [SMILES: "MeOH" ; CC(C)(C)[Si](C)(C)O[C@H]1C[C@H](N=[N+]=[N-])C[C@H](N=[N+]=[N-])C1 ; CC(C)(C)[Si](C)(C)O[C@H]1C[C@H](N)C[C@H](N)C1]

A degassed solution of tert-butyl((+/−)-3,5-diazidocyclohexyloxy)dimethylsilane (300 mg, 1.01 mmol) (prepared following New J. Chem., 2005, 29, 1152-1158) in MeOH (7 mL) was treated with 10% Pd/C (108 mg, 0.10 mmol) and stirred 2 h under hydrogen (1 atm). The resulting mixture was filtered over a pad of celite and the filtrate was evaporated to dryness leaving the title compound (227 mg, 0.930 mmol, 92%) as a beige solid which was used in the next step without further purification.

(+/−)-5-(tert-butyldimethylsilyloxy)-$N^1$-(5-chloro-4-(1-(phenylsulfonyl)-1H-indol-3-yl)pyrimidin-2-yl)cyclohexane-1,3-diamine

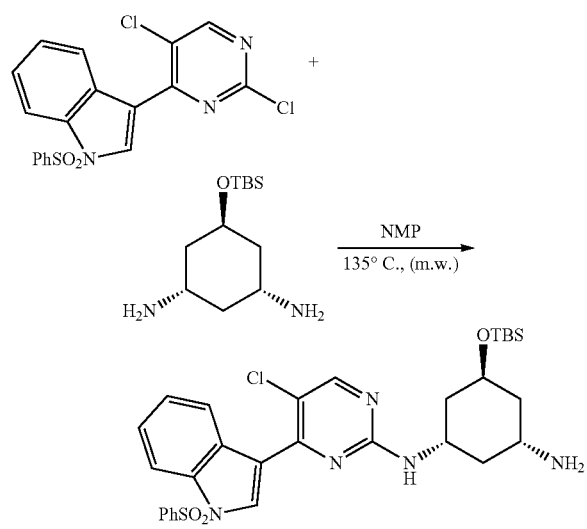

A solution of 3-(2,5-dichloropyrimidin-4-yl)-1-(phenylsulfonyl)-1H-indole (340 mg, 0.84 mmol), (+/−)-5-(tert-butyldimethylsilyloxy)cyclohexane-1,3-diamine (226 mg, 0.93 mmol) and DIPEA (161 μL, 0.93 mmol) in NMP (1.4 mL) was heated at 135° C. (microwave) for 25 min. The cooled mixture was diluted with EtOAc (30 mL), washed with $H_2O$ (10 mL), brine (10 mL), dried over $MgSO_4$, filtered, and evaporated to dryness. The residue was purified by $C_{18}$ chromatography ($H_2O$/ACN+0.1% $HCO_2H$ 5 to 80% gradient) to afford the title compound (97 mg, 0.158 mmol, 19%) as a pale yellow solid.

(+/−)-tert-butyl 4-(-3-(tert-butyldimethylsilyloxy)-5-(5-chloro-4-(1-(phenylsulfonyl)-1H-indol-3-yl)pyrimidin-2-ylamino)cyclohexylcarbamoyl)phenylcarbamate

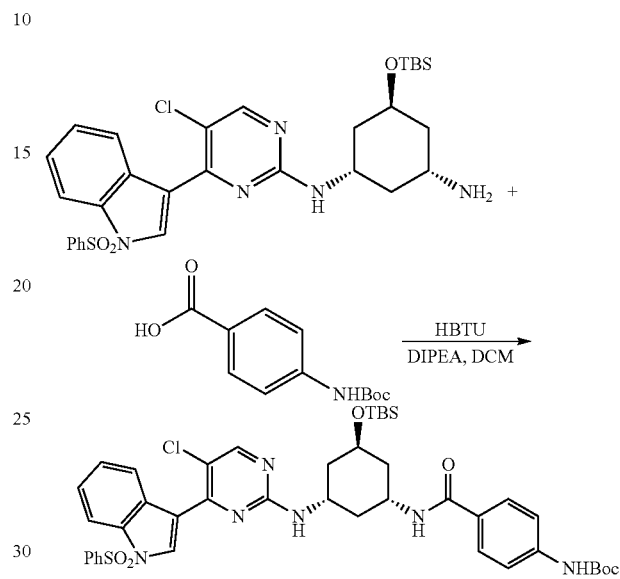

A solution of (+/−)-5-(tert-butyldimethylsilyloxy)-$N^1$-(5-chloro-4-(1-(phenylsulfonyl)-1H-indol-3-yl)pyrimidin-2-yl)cyclohexane-1,3-diamine (97 mg, 0.16 mmol) and 4-(tert-butoxycarbonylamino)benzoic acid (38 mg, 0.16 mmol) in DCM (1.1 mL) was treated with HBTU (120 mg, 0.32 mmol) and DIPEA (83 μL, 0.48 mmol). The resulting mixture was stirred 18 h at rt and evaporated to dryness. The residue was purified by $SiO_2$ chromatography (DCM/EtOAc 0 to 50% gradient) to afford the title compound (93 mg, 0.111 mmol, 71%) as a light yellow oil.

(+/−)-4-amino-N-(3-(5-chloro-4-(1H-indol-3-yl)pyrimidin-2-ylamino)-5-hydroxycyclohexyl)benzamide

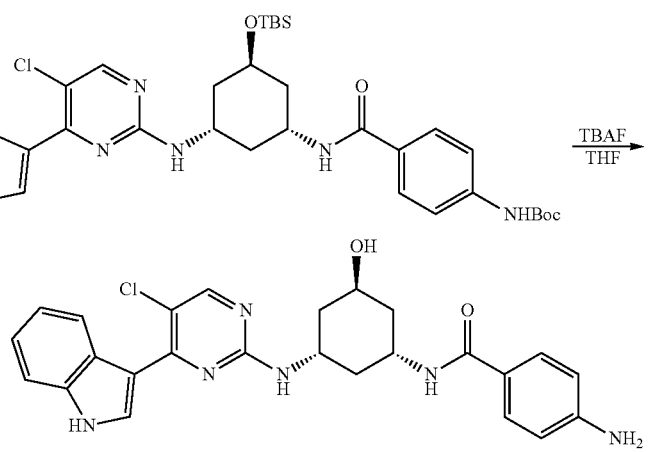

A solution of (+/−)-tert-butyl 4-(-3-(tert-butyldimethylsilyloxy)-5-(5-chloro-4-(1-(phenylsulfonyl)-1H-indol-3-yl)pyrimidin-2-ylamino)cyclohexylcarbamoyl)phenylcarbamate (93.0 mg, 0.112 mmol) in THF (4.5 mL) was treated with a 1M solution of TBAF in THF (168 µL, 0.168 mmol) and stirred 2 days at rt. The resulting mixture was evaporated to dryness and the residue was purified by reverse phase chromatography ($C_{18}$, $H_2O$/ACN+0.1% $HCO_2H$ 10 to 100% gradient) and to afford the title compound (32 mg, 0.067 mmol, 60%) as a yellow solid.

Example 3. 4-amino-N-((1S,3R)-3-(5-chloro-4-(1H-indol-3-yl)pyrimidin-2-ylamino)cyclohexyl)benzamide (Compound 102)

(1S,3R)-3-(Benzyloxycarbonylamino)cyclohexylamino 2,2-dimethylpropionate

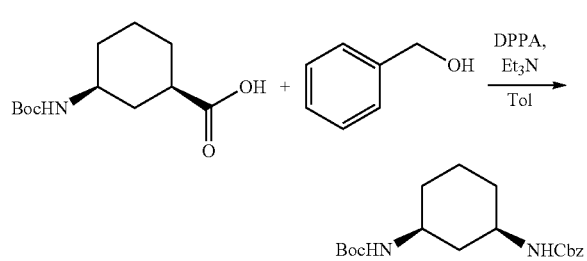

To a solution of (1R,3S)-3-(tert-butoxycarbonylamino)cyclohexanecarboxylic acid (prepared following Tetrahedron: *Asymmetry* 2010 (21), 864-866) (8.77 g, 36.1 mmol) was added $Et_3N$ (5.53 mL, 39.7 mmol) and DPPA (7.7 mL, 36.1 mmol). The resulting solution was stirred 2 h at 110° C. then cooled down to 80° C. Benzyl alcohol (4.66 mL, 45.1 mmol) and triethylamine (5.53 mL, 39.7 mmol) were added and the mixture was stirred 20 h at 80° C. The cooled solution was diluted with EtOAc (100 mL) and $H_2O$ (50 mL). The layers were separated and the aqueous layer was extracted with EtOAc (2×50 mL). The combined organics were dried ($MgSO_4$), filtered and evaporated to dryness. The residue was purified by $SiO_2$ chromatography (Hex/EtOAc 1 to 100% gradient), and afforded the title compound (9.89 g, 28.4 mmol, 79%) as a white solid.

tert-butyl (1S,3R)-3-aminocyclohexylcarbamate

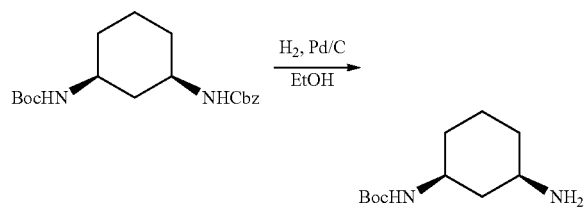

To a degassed solution of (1S,3R)-3-(Benzyloxycarbonylamino)cyclohexylamino 2,2-dimethylpropionate (10 g, 28.4 mmol) in EtOH (473 mL) was added 10% w/w Pd/C (450 mg). The reaction mixture was stirred 5 h under $H_2$ (1 atm). The reaction mixture was filtered through a pad of celite (EtOH) and the filtrate was evaporated to dryness to afford the title compound (6.08 g, 28.4 mmol, 100%) as a white solid.

tert-butyl-(1S,3R)-3-(5-chloro-4-(1-(phenylsulfonyl)-1H-indol-3-yl)pyrimidin-2-ylamino)cyclohexylcarbamate

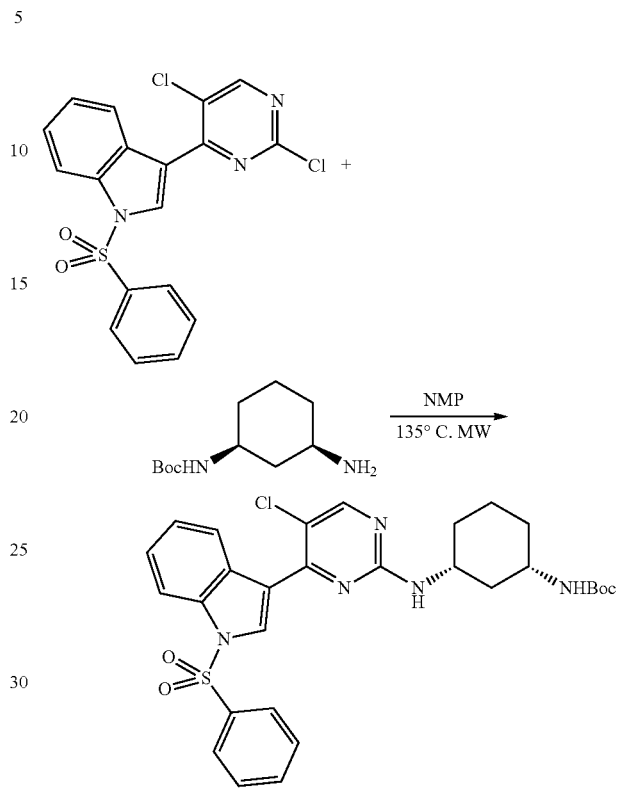

A solution of 3-(2,5-dichloropyrimidin-4-yl)-1-(phenylsulfonyl)-1H-indole (2.91 g, 7.20 mmol), tert-butyl (1S,3R)-3-aminocyclohexylcarbamate (1.24 g, 5.76 mmol) and diisopropylethylamine (1.05 mL, 6.05 mmol) in NMP (14.5 mL) was heated 1.5 h at 135° C. (mW). The mixture was diluted with EtOAc (200 mL), washed with $H_2O$ (50 mL), brine (50 mL), dried ($MgSO_4$), filtered and evaporated to dryness. The residue was purified by $SiO_2$ chromatography (DCM/EtOAc 0 to 30% gradient) and afforded the title compound (1.88 g, 3.23 mmol, 56%) as a light yellow foam.

(1R,3S)—$N^1$-(5-chloro-4-(1-(phenylsulfonyl)-1H-indol-3-yl)pyrimidin-2-yl)cyclohexane-1,3-diamine.HCl

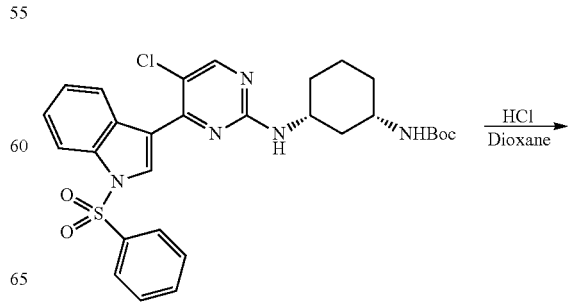

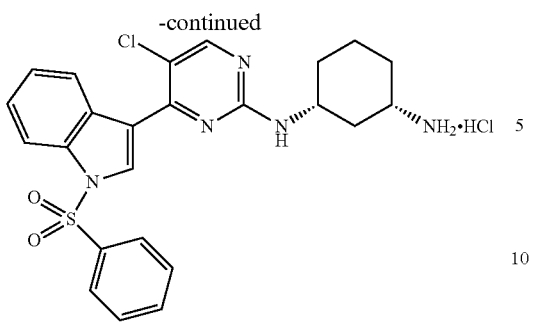

To a solution of tert-butyl (1S,3R)-3-(5-chloro-4-(1-(phenylsulfonyl)-1H-indol-3-yl)pyrimidin-2-ylamino)cyclohexylcarbamate (1.88 g, 3.23 mmol) in DCM (16.1 mL) was added a solution of HCl 4 N in dioxane (12.11 mL, 48.44 mmol). The resulting mixture was stirred 1.5 h at rt before being evaporated to dryness and afforded the title compound (1.72 g, 3.10 mmol, 96%) as a light yellow solid which was used in the next step without further purification.

tert-butyl-4-((1 S,3R)-3-(5-chloro-4-(1-(phenylsulfonyl)-1H-indol-3-yl)pyrimidin-2-ylamino)cyclohexylcarbamoyl)phenylcarbamate

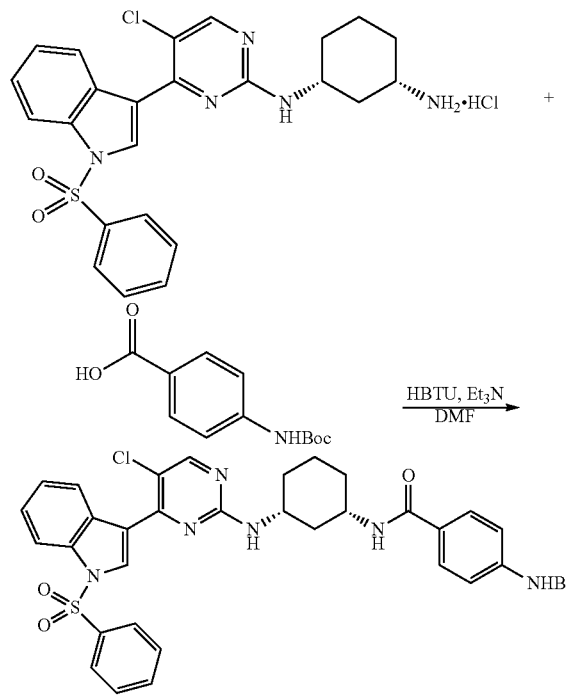

A solution of (1R,3S)—$N^1$-(5-chloro-4-(1-(phenylsulfonyl)-1H-indol-3-yl)pyrimidin-2-yl)cyclohexane-1,3-diamine.HCl (840 mg, 1.62 mmol), 4-(tert-butoxycarbonylamino)benzoic acid (462 mg, 1.95 mmol), HBTU (924 mg, 2.44 mmol), Et₃N (680 μL, 4.87 mmol) in DMF (8.0 mL) was stirred overnight at rt. The mixture was diluted with EtOAc (50 mL), washed with sat NaHCO₃ (10 mL), H₂O (10 mL) and brine (10 mL). The organic layer was dried over MgSO₄, filtered and concentrated under reduced pressure and afforded the title compound which was used in the next step without further purification (1.14 g, 1.62 mmol, 100%)

4-amino-N-((1 S,3R)-3-(5-chloro-4-(1-(phenylsulfonyl)-1H-indol-3-yl)pyrimidin-2-ylamino)cyclohexyl)benzamide.HCl

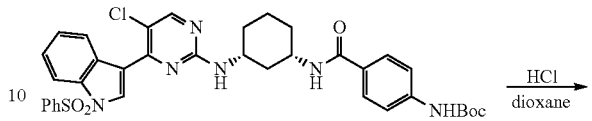

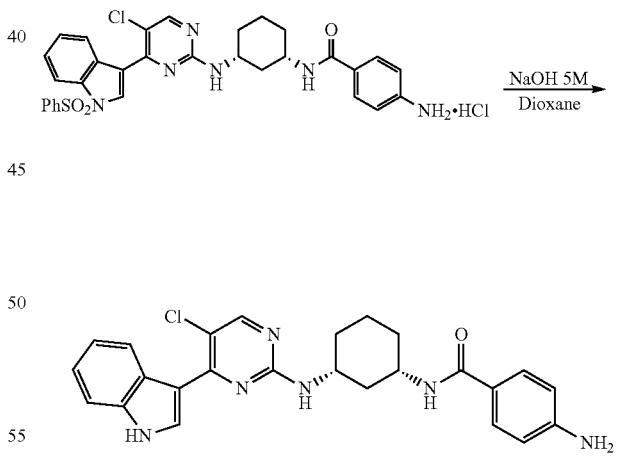

A solution of tert-butyl 44(1S,3R)-3-(5-chloro-4-(1-(phenylsulfonyl)-1H-indol-3-yl)pyrimidin-2-ylamino)cyclohexylcarbamoyl)phenylcarbamate (1.14 g, 1.62 mmol) in DCM (10 mL) was treated with a 4M solution of HCl in dioxane (8.1 mL, 32.4 mmol) ans stirred 3 h at rt. The resulting mixture was evaporated to dryness and afforded the title compound (948 mg, 1.62 mmol, 100%) as a pale yellow solid which was used in the next step without further purification.

4-amino-N-((1 S,3R)-3-(5-chloro-4-(1H-indol-3-yl)pyrimidin-2-ylamino)cyclohexyl)benzamide A solution of 4-amino-N4(1S,3R)-3-(5-chloro-4-(1-(phenylsulfonyl)-1H-indol-3-yl)pyrimidin-2-ylamino)cyclohexyl)benzamide.HCl (1.72 g, 3.10 mmol) and NaOH 5M (9.3 mL, 46.5 mmol) in dioxane (20 mL) was stirred 2.5 h at 75° C. The cooled mixture was concentrated, diluted with DCM (100 mL) and H₂O (20 mL). The layers were separated and the aqueous layer was extracted with DCM (3×20 mL), dried over MgSO₄, filtered, evaporated to dryness and afforded the title compound (1.20 g, 2.60 mmol, 84%) as a white solid.

Example 4. (1S,3R)—N-(4-aminophenyl)-3-(5-chloro-4-(1H-indol-3-yl)pyrimidin-2-ylamino)cyclohexanecarboxamide (Compound 106)

(1S,3R)-methyl 3-(tert-butoxycarbonylamino)cyclohexanecarboxylate

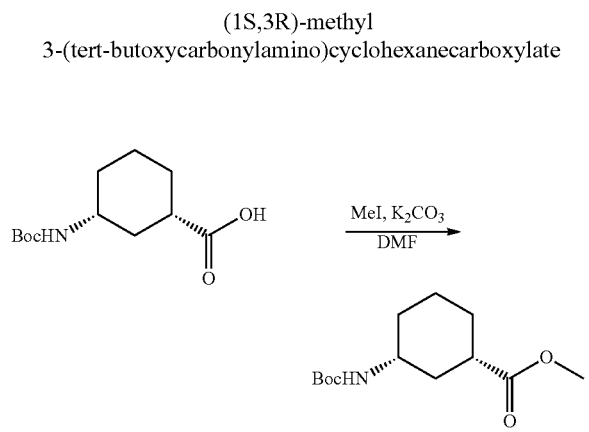

A solution of (1R,3S)-3-(tert-butoxycarbonylamino)cyclohexanecarboxylic acid (prepared following Tetrahedron: Asymmetry 2010 (21), 864-866) (1.0 g, 4.11 mmol), $K_2CO_3$ (474 mg, 3.43 mmol) and MeI (0.21 mL, 3.43 mmol) in DMF (8 mL) was stirred 72 h at rt. The resulting mixture was diluted with $H_2O$ (30 mL) and EtOAc (100 mL). The layers were separated and the aqueous layer was extracted with EtOAc (3×50 mL). The combined organic layers were dried over $MgSO_4$, filtered, and evaporated to dryness leaving the title compound (1.35 g, 4.11 mmol, 100%) as a light orange solid which was used in the next step without further purification.

(1S,3R)-methyl 3-aminocyclohexanecarboxylate.HCl

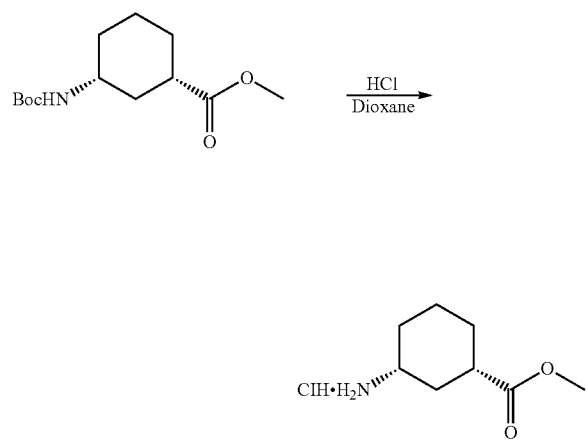

A solution of (1S,3R)-methyl 3-(tert-butoxycarbonylamino)cyclohexanecarboxylate (1.058 g, 4.111 mmol) in DCM (20.6 mL) was treated with a 4M solution of HCl in dioxane (10.3 mL, 10.3 mmol) and stirred for 16 h. The mixture was concentrated to dryness leaving the title compound (739 mg, 3.81 mmol, 93%) as a light yellow solid which was used in the next step without further purification.

(1S,3R)-methyl 3-(5-chloro-4-(1-(phenylsulfonyl)-1H-indol-3-yl)pyrimidin-2-ylamino)cyclohexanecarboxylate

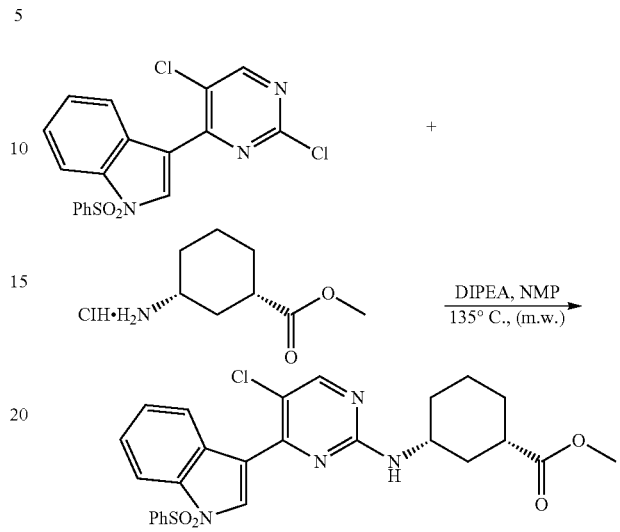

A solution of 3-(2,5-dichloropyrimidin-4-yl)-1-(phenylsulfonyl)-1H-indole (1.401 g, 3.464 mmol), (1S,3R)-methyl 3-aminocyclohexanecarboxylate.HCl (639 mg, 3.299 mmol) and DIPEA (1.7 mL, 9.90 mmol) in NMP (13 mL) was heated at 135° C. (microwave) for 25 min. The cooled mixture was diluted with EtOAc (50 mL), washed with $H_2O$ (15 mL), brine (15 mL), dried over $MgSO_4$, filtered, and evaporated to dryness. The residue was purified by $SiO_2$ chromatography (DCM/EtOAc 0 to 10% gradient) to afford the title compound (900 mg, 1.71 mmol, 52%) as a white foam.

(1S,3R)-3-(5-chloro-4-(1-(phenylsulfonyl)-1H-indol-3-yl)pyrimidin-2-ylamino)cyclohexanecarboxylic acid

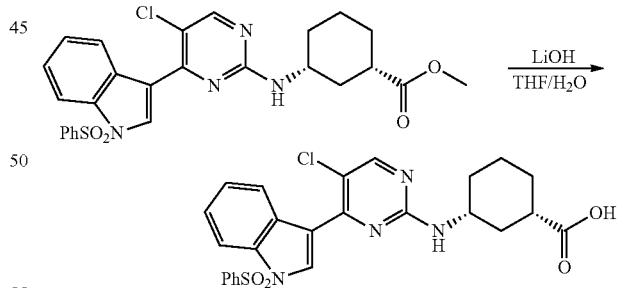

A solution of (1S,3R)-methyl 3-(5-chloro-4-(1-(phenylsulfonyl)-1H-indol-3-yl)pyrimidin-2-ylamino)cyclohexanecarboxylate (200 mg, 0.38 mmol) in THF was treated with a 0.55M solution of $LiOH.H_2O$ in $H_2O$ (0.8 mL, 0.4 mmol) and for three days at rt. The mixture was diluted with EtOAc (20 mL) and acidified with 1M HCl until the pH reached 2-3. The layers were separated and the aqueous layer was extracted with EtOAc (3×10 mL), dried over $MgSO_4$, filtered and evaporated to dryness leaving the title compound (108 mg, 0.211 mmol, 56%) as a white solid which was used in the next step without further purification.

tert-butyl 4-((1S,3R)-3-(5-chloro-4-(1-(phenylsulfonyl)-1H-indol-3-yl)pyrimidin-2-ylamino)cyclohexanecarboxamido)phenylcarbamate

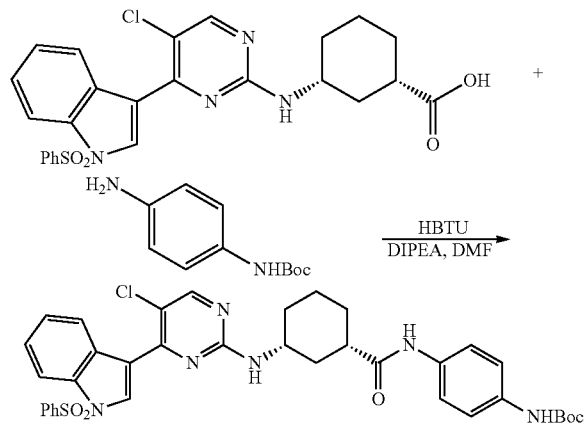

A solution of (1S,3R)-3-(5-chloro-4-(1-(phenylsulfonyl)-1H-indol-3-yl)pyrimidin-2-ylamino)cyclohexanecarboxylic acid (108 mg, 0.21 mmol) and tert-butyl 4-aminophenylcarbamate (44 mg, 0.21 mmol) in DCM (1.4 mL) was treated with HBTU (160 mg, 0.42 mmol) and DIPEA (0.11 mL, 0.63 mmol). The resulting mixture was stirred 18 h at rt and evaporated to dryness. The residue was purified by SiO₂ chromatography (Hex/EtOAc 15 to 100% gradient) to afford the title compound (144 mg, 0.205 mmol, 97%) as a light yellow oil.

(1S,3R)—N-(4-aminophenyl)-3-(5-chloro-4-(1-(phenylsulfonyl)-1H-indol-3-yl)pyrimidin-2-ylamino)cyclohexanecarboxamide.TFA

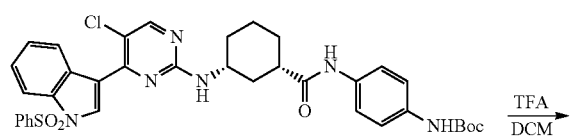

A solution of tert-butyl 44(1S,3R)-3-(5-chloro-4-(1-(phenylsulfonyl)-1H-indol-3-yl)pyrimidin-2-ylamino)cyclohexanecarboxamido)phenylcarbamate (144 mg, 0.21 mmol) in DCM (1 mL) was treated with TFA (0.16 mL, 2.05 mmol) and stirred 1 h at rt. The mixture was evaporated to dryness to afford the title compound (142 mg, 0.811 mmol, 97%) as a yellow solid.

(1S,3R)—N-(4-aminophenyl)-3-(5-chloro-4-(1H-indol-3-yl)pyrimidin-2-ylamino)cyclohexanecarboxamide

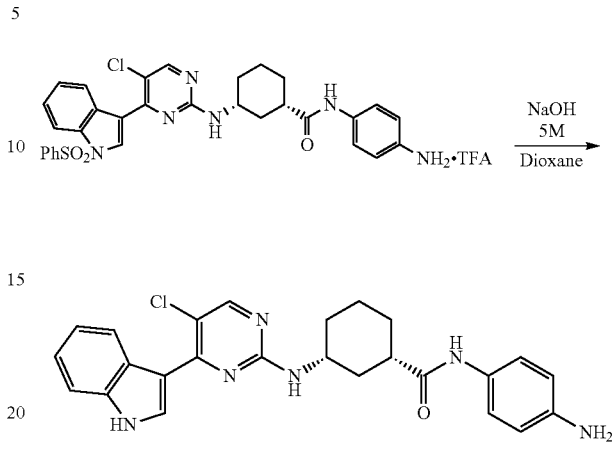

A solution of (1S,3R)—N-(4-aminophenyl)-3-(5-chloro-4-(1-(phenylsulfonyl)-1H-indol-3-yl)pyrimidin-2-ylamino)cyclohexanecarboxamide.TFA (142 mg, 0.20 mmol) in dioxane (1.4 mL) was treated with a 5M solution of NaOH in H₂O (0.81 mL, 4.07 mmol) and stirred at 75° C. for 3 h. The cooled mixture was evaporated to dryness and H₂O (2 mL) was added to the residue. The resulting solid was filtered, washed with H₂O (2×1 mL), and dried under high vacuum leaving the title compound (90 mg, 0.195 mmol, 96%) as a white solid.

Example 5. 4-amino-N-((1S,3R)-3-(5-cyclopropyl-4-(1H-indol-3-yl)pyrimidin-2-ylamino)cyclohexyl)benzamide.HCl (Compound 103)

benzyl (1S,3R)-3-aminocyclohexylcarbamate.HCl

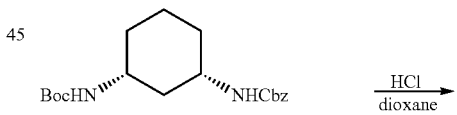

A solution of (1R,3S)-3-(Benzyloxycarbonylamino)cyclohexylamino 2,2-dimethylpropionate prepared similarly to Example 3 (1.50 g, 4.31 mmol) in DCM (43 mL) was treated with a 4M solution of HCl in dioxane (16 mL, 64.6 mmol) and stirred 2 h at rt. The resulting solution was evaporated to dryness to afford the title compound (1.23 g, 4.31 mmol, 100%) as a white solid which was used in the next step without further purification.

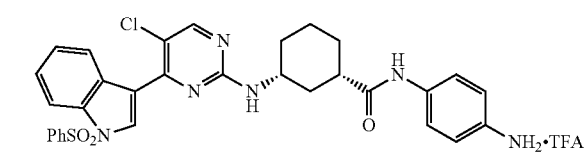

benzyl (1S,3R)-3-(5-chloro-4-(1-(phenylsulfonyl)-1H-indol-3-yl)pyrimidin-2-ylamino)cyclohexylcarbamate

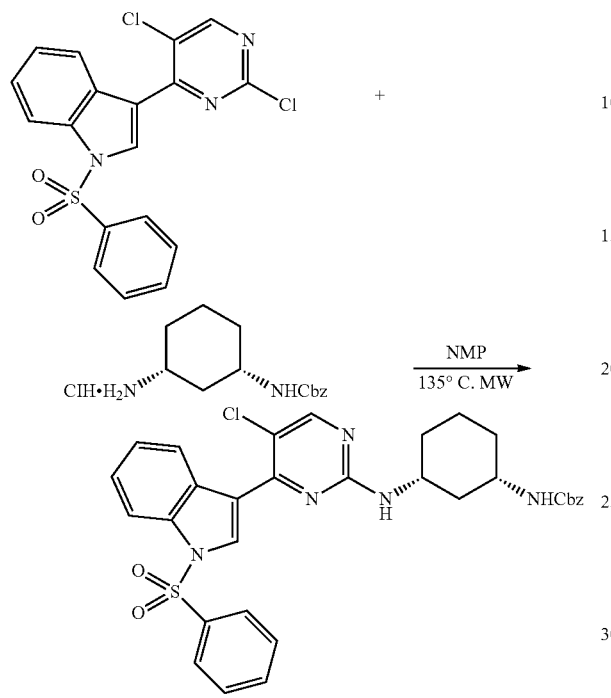

A solution of 3-(2,5-dichloropyrimidin-4-yl)-1-(phenylsulfonyl)-1H-indole (791 mg, 1.96 mmol), benzyl (1S,3R)-3-aminocyclohexylcarbamate (613 mg, 2.15 mmol) and diisopropylethylamine (0.75 mL, 4.31 mmol) in NMP (20.0 mL) was heated 30 min at 135° C. (mW). The mixture was diluted with EtOAc (100 mL), washed with H₂O (50 mL), brine (50 mL), dried (MgSO₄), filtered and evaporated to dryness. The residue was purified by SiO₂ chromatography (Hex/EtOAc 5 to 70% gradient), to afford the title compound (1.04 g, 1.69 mmol, 40%) as a yellow solid.

Benzyl (1S,3R)-3-(5-cyclopropyl-4-(1-(phenylsulfonyl)-1H-indol-3-yl)pyrimidin-2-ylamino)cyclohexylcarbamate

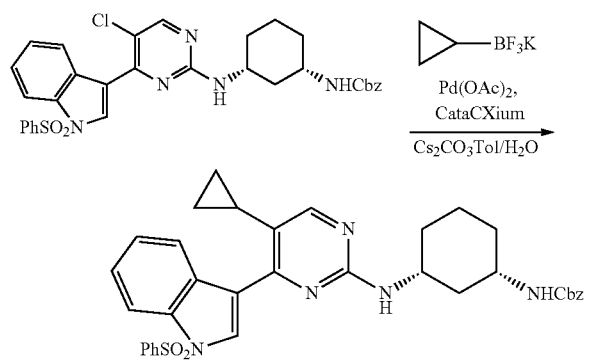

A degassed solution of benzyl (1S,3R)-3-(5-chloro-4-(1-(phenylsulfonyl)-1H-indol-3-yl)pyrimidin-2-ylamino)cyclohexylcarbamate (prepared similarly to Example 3) (500 mg, 0.812 mmol), Cs₂CO₃ (794 mg, 2.435 mmol) and potassium cyclopropyltrifluoroborate (360 mg, 2.435 mmol) in 2/1 toluene/H₂O (15 mL) was treated with a premixed solution of Pd(OAc)₂ (9 mg, 0.04 mmol) and butyldi-1-adamantylphosphine (29 mg, 0.08 mmol) in degassed toluene (2 mL) and heated at 140° C. (microwave) for 2 h. The cooled mixture was diluted with EtOAc (50 mL) and saturated NaHCO₃ (20 mL). The layers were separated and the aqueous layer was extracted with EtOAc (2×20 mL). The combined organic layers were dried over Na₂SO₄, filtered and evaporated to dryness. The residue was purified by SiO₂ chromatography (Hex/EtOAc 0 to 60% gradient) to afford the title compound (324 mg, 0.521 mmol, 64%) as a pale yellow solid.

(1R,3S)—N¹-(5-cyclopropyl-4-(1-(phenylsulfonyl)-1H-indol-3-yl)pyrimidin-2-yl)cyclohexane-1,3-diamine

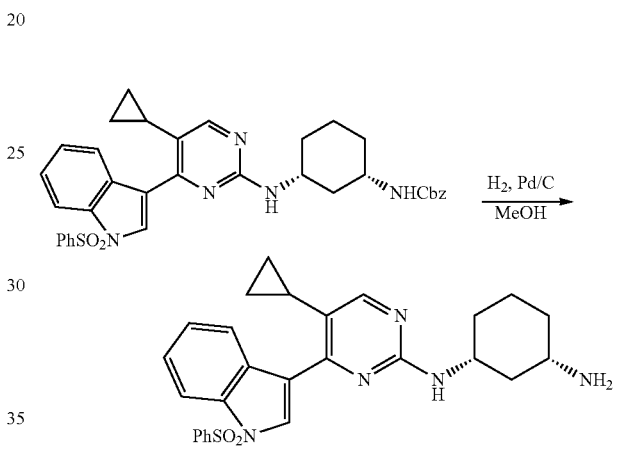

A degassed solution of benzyl (1S,3R)-3-(5-cyclopropyl-4-(1-(phenylsulfonyl)-1H-indol-3-yl)pyrimidin-2-ylamino)cyclohexylcarbamate (778 mg, 1.250 mmol) in MeOH (60 mL) was treated with 10% wet Pd/C (150 mg) and stirred under H₂ (1 atm) for 6 h. The mixture was filtered on celite (MeOH) and the filtrate was evaporated to dryness to afford the title compound (610 mg, 1.25 mmol, 75%) as a white foam which was used in the next step without further purification.

tert-butyl 4-((1S,3R)-3-(5-cyclopropyl-4-(1-(phenylsulfonyl)-1H-indol-3-yl)pyrimidin-2-ylamino)cyclohexylcarbamoyl)phenylcarbamate

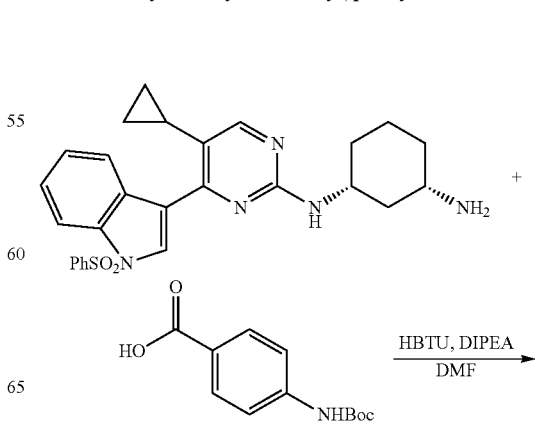

-continued

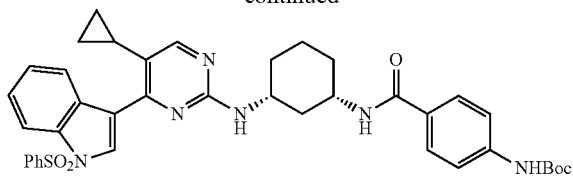

A solution of (1R,3S)—N¹-(5-cyclopropyl-4-(1-(phenylsulfonyl)-1H-indol-3-yl)pyrimidin-2-yl)cyclohexane-1,3-diamine (457 mg, 0.937 mmol) and 4-(tert-butoxycarbonylamino)benzoic acid (245 mg, 1.031 mmol) in DMF (10 mL) was treated with HBTU (533 mg, 1.406 mmol) and DIPEA (245 µL, 1.406 mmol). The resulting mixture was stirred overnight at rt and diluted with EtOAc (50 mL) and saturated NaHCO₃ (20 mL). The layers were separated and the aqueous layer was extracted with EtOAc (2×30 mL). The combined organic layers were dried over Na₂SO₄, filtered, and evaporated to dryness leaving the title compound (662 mg, 0.936 mmol, 100%) as a yellow solid which was used in the next step without further purification.

tert-butyl 4-((1 S,3R)-3-(5-cyclopropyl-4-(1H-indol-3-yl)pyrimidin-2-ylamino)cyclohexylcarbamoyl)phenylcarbamate

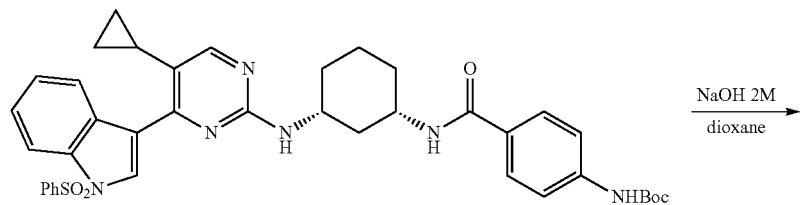

A solution of tert-butyl 44(1S,3R)-3-(5-cyclopropyl-4-(1-(phenylsulfonyl)-1H-indol-3-yl)pyrimidin-2-ylamino)cyclohexylcarbamoyl)phenylcarbamate (663 mg, 0.938 mmol) in dioxane (10 mL) was treated with a 2M solution of NaOH (7 mL, 14 mmol) and heated at 70° C. for 1 h. The cooled mixture was diluted with MeTHF (20 mL) and the layers were separated. The aqueous layer was extracted with MeTHF (3×20 mL) and the combined organic layers were dried over Na₂SO₄, filtered, and evaporated to dryness affording the title compound (531 mg, 0.937 mmol, 99.9%) as a pale yellow solid which was used in the next step without further purification.

4-amino-N-((1 S,3R)-3-(5-cyclopropyl-4-(1H-indol-3-yl)pyrimidin-2-ylamino)cyclohexyl)benzamide.HCl

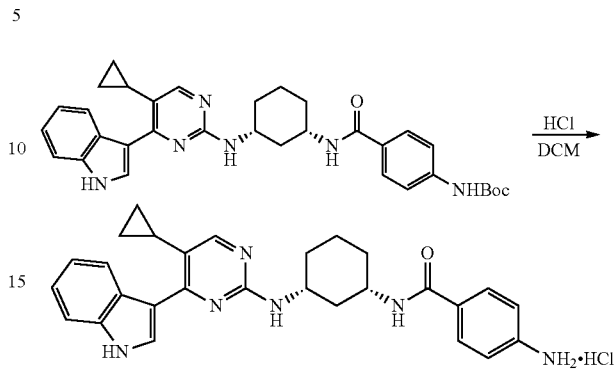

A solution of tert-butyl 44(1S,3R)-3-(5-cyclopropyl-4-(1H-indol-3-yl)pyrimidin-2-ylamino)cyclohexylcarbamoyl)phenylcarbamate (531 mg, 0.938 mmol) in DCM (10 mL) was treated with a 4M solution of HCl in dioxane (3.50 mL, 14.0 mmol) and stirred 2 h at rt. The resulting mixture was evaporated to dryness to afford the title compound (471 mg, 0.938 mmol, 100%) as a white solid.

Example 6. 4-amino-N-((1S,3R)-3-(5-chloro-4-(pyridin-3-yl)pyrimidin-2-ylamino)cyclohexyl)benzamide (Compound 108)

tert-butyl (1 S, 3R)-3-(5-chloro-4-(pyridin-3-yl)pyrimidin-2-ylamino)cyclohexylcarbamate

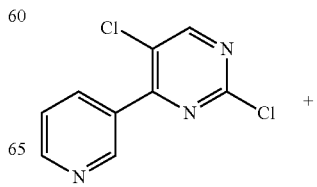 +

-continued

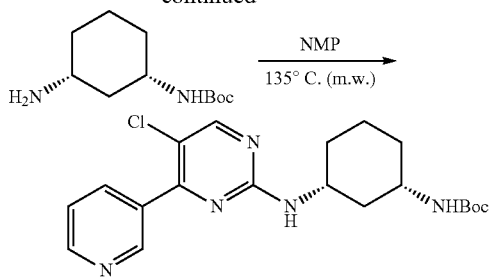

A solution of 2,5-dichloro-4-(pyridin-3-yl)pyrimidine (173 mg, 0.0.764 mmol), tert-butyl (1S,3R)-3-aminocyclohexylcarbamate (182 mg, 0.849 mmol), and DIPEA (0.16 mL, 0.892 mmol) in NMP (7.1 mL) was heated at 135° C. (mW) for 60 min. The cooled mixture was diluted with EtOAc (30 mL), washed with H$_2$O (10 mL), brine (10 mL), dried over MgSO$_4$, filtered, and evaporated to dryness. The residue was purified by SiO$_2$ chromatography (DCM/EtOAc 0 to 70% gradient) to afford the title compound (185 mg, 0.458 mmol, 54%) as a light yellow foam.

(1R,3S)—N$^1$-(5-chloro-4-(pyridin-3-yl)pyrimidin-2-yl)cyclohexane-1,3-diamine.HCl

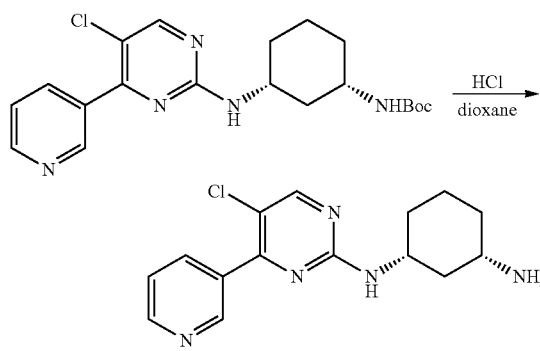

A solution of tert-butyl (1S,3R)-3-(5-chloro-4-(pyridin-3-yl)pyrimidin-2-ylamino)cyclohexylcarbamate (210 mg, 0.520 mmol) in DCM (2.6 mL) was treated with a 4M solution of HCl in dioxane (1.3 mL, 5.130 mmol) and stirred 2 h at rt. The resulting mixture was evaporated to dryness to afford the title compound (177 mg, 0.520 mmol, 100%) as a light yellow solid which was used in the next step without further purification.

tert-butyl 4-((1S,3R)-3-(5-chloro-4-(pyridin-3-yl)pyrimidin-2-ylamino)cyclohexylcarbamoyl)phenylcarbamate

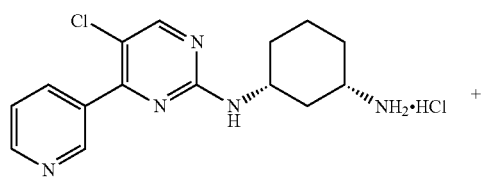 +

-continued

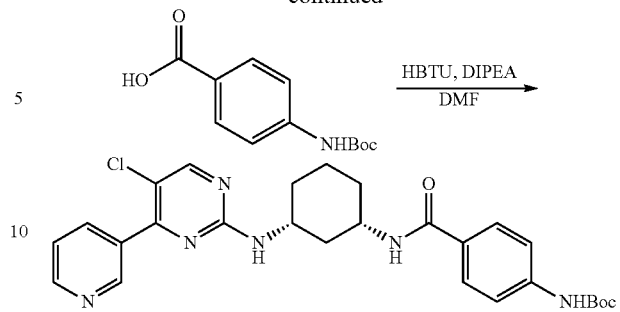

A solution of (1R,3S)—N$^1$-(5-chloro-4-(pyridin-3-yl)pyrimidin-2-yl)cyclohexane-1,3-diamine.HCl (297 mg, 0.783 mmol) and 4-(tert-butoxycarbonylamino)benzoic acid (149 mg, 0.626 mmol) in DMF (5.2 mL) was treated with HBTU (297 mg, 0.783 mmol) and DIPEA (364 µL, 2.087 mmol). The resulting mixture was stirred overnight at rt and diluted with EtOAc (30 mL) and saturated NaHCO$_3$ (15 mL). The layers were separated and the aqueous layer was extracted with EtOAc (2×30 mL). The combined organic layers were dried over MgSO$_4$, filtered, and evaporated to dryness. The residue was purified by SiO$_2$ chromatography (DCM/EtOAc, 0 to 100% gradient) to afford the title compound (227 mg, 0.434 mmol, 83%) as a light yellow solid.

4-amino-N-((1S,3R)-3-(5-chloro-4-(pyridin-3-yl)pyrimidin-2-ylamino)cyclohexyl) benzamide

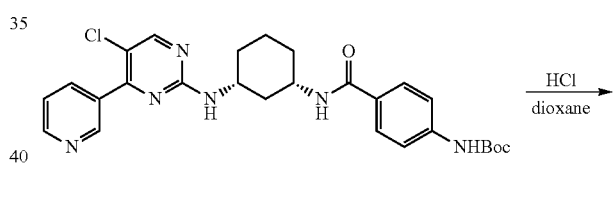

A solution of tert-butyl 4-((1S,3R)-3-(5-chloro-4-(pyridin-3-yl)pyrimidin-2-ylamino)cyclohexylcarbamoyl)phenylcarbamate (166 mg, 0.317 mmol) in DCM (3.2 mL) was treated with a 4M solution of HCl in dioxane (0.79 mL, 3.17 mmol) and stirred 16 h at rt. The resulting mixture was evaporated to dryness and diluted with EtOAc (20 mL) and saturated NaHCO$_3$ (10 mL). The layers were separated and the aqueous layer was extracted with EtOAc (3×15 mL). The combined organic layers were dried over MgSO$_4$, filtered, and evaporated to dryness to afford the title compound (134 mg, 0.317 mmol, 100%) as a white solid.

Example 7. 4-amino-N-((1S,3R)-3-(5-cyano-4-(1H-indol-3-yl)pyrimidin-2-ylamino)cyclohexyl)benzamide (Compound 107)

4-amino-N-((1S,3R)-3-(5-cyano-4-(1-(phenylsulfonyl)-1H-indol-3-yl)pyrimidin-2-ylamino)cyclohexyl)benzamide

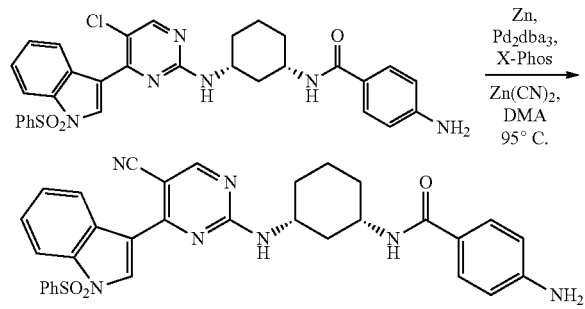

A degassed solution of 4-amino-N-((1S,3R)-3-(5-chloro-4-(1-(phenylsulfonyl)-1H-indol-3-yl)pyrimidin-2-ylamino)cyclohexyl)benzamide (prepared as in example 3) (222 mg, 0.369 mmol) in DMA (4 mL) was treated with a premixed and degassed solution of Zn (2.4 mg, 0.04 mmol), Pd$_2$dba$_3$ (33.8 mg, 0.04 mmol), X-Phos (35.2 mg, 0.07 mmol) and Zn(CN)$_2$ (26.0 mg, 0.22 mmol) in DMA (3 mL) and heated at 95° C. for 18 h. The cooled mixture was diluted with EtOAc (40 mL), washed with H$_2$O (10 mL), brine (10 mL), dried over MgSO$_4$, filtered, and evaporated to dryness. The residue was purified by SiO$_2$ chromatography (DCM/EtOAc 0 to 70% gradient) to afford the title compound (113 mg, 0.191 mmol, 52%) as a light yellow solid.

4-amino-N-((1S,3R)-3-(5-cyano-4-(1H-indol-3-yl)pyrimidin-2-ylamino)cyclohexyl)benzamide

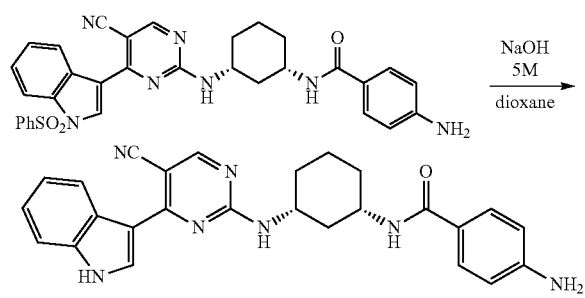

A solution of 4-amino-N4(1S,3R)-3-(5-cyano-4-(1-(phenylsulfonyl)-1H-indol-3-yl)pyrimidin-2-ylamino)cyclohexyl)benzamide (33 mg, 0.0549 mmol) in dioxane (3.8 mL) was treated with a 5M solution of NaOH (50 µL, 0.275 mmol) and heated at 50° C. for 43 h. The cooled mixture was treated with a 1M solution of HCl until a pH of 3 was reached, and then the mixture was evaporated to dryness. The residue was purified by reverse phase chromatography (C$_{18}$, H$_2$O/ACN+0.1% HCO$_2$H 80 to 100% gradient) to afford the title compound (48 mg, 0.106 mmol, 55%) as a white solid after lyophilisation.

Example 8. (+/−)-4-amino-N-(3-(5-chloro-4-(1H-indol-3-yl)pyrimidin-2-ylamino)-5-fluorocyclohexyl)benzamide (Compound 110)

(+/−)-1,3-diazido-5-fluorocyclohexane

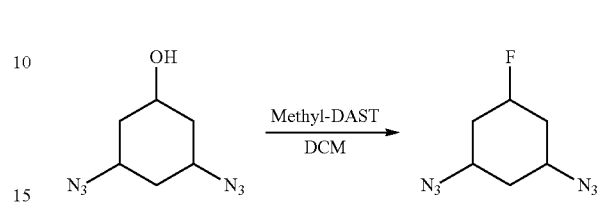

A cooled (−78° C.) solution of (+/−)-3,5-diazidocyclohexanol (prepared following New J. Chem., 2005, 29, 1152-1158) in DCM (30 mL) was treated dropwise with Me-DAST (268 µL, 2.74 mmol) and stirred 18 h at this temperature. A saturated solution of NaHCO$_3$ (10 mL) was added, the layers were separated and the aqueous layer was extracted with EtOAc (3×10 mL). The combined organic layers were dried over MgSO$_4$, filtered and evaporated to dryness. The residue was purified by SiO$_2$ chromatography (Hex/Et$_2$O 0 to 5% gradient) and afforded the title compound (141 mg, 0.349 mmol, 35%) as a colorless oil.

(+/−)-5-fluorocyclohexane-1,3-diamine

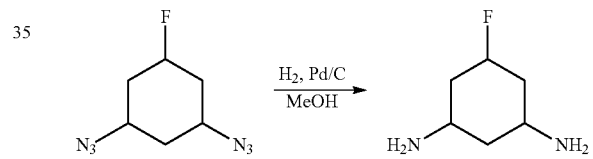

A degassed solution of (+/−)-1,3-diazido-5-fluorocyclohexane (141 mg, 0.77 mmol) in MeOH (5 mL) was treated with 10% Pd/C (81 mg, 0.08 mmol) and stirred under H$_2$ (1 atm) for 5 h. The resulting mixture was filtered over celite (MeOH) and the filtrate was evaporated to dryness affording the title compound (77 mg, 0.583 mmol, 76%) as a beige solid which was used in the next step without further purification.

(+/−)-tert-butyl 4-(-3-(5-chloro-4-(1-(phenylsulfonyl)-1H-indol-3-yl)pyrimidin-2-ylamino)-5-fluorocyclohexylcarbamoyl)phenylcarbamate

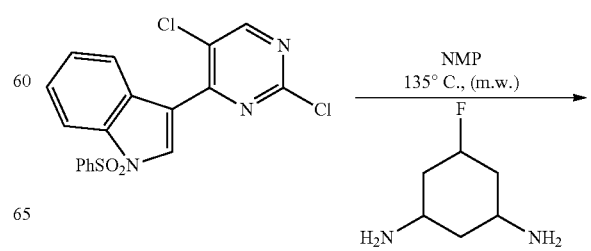

-continued

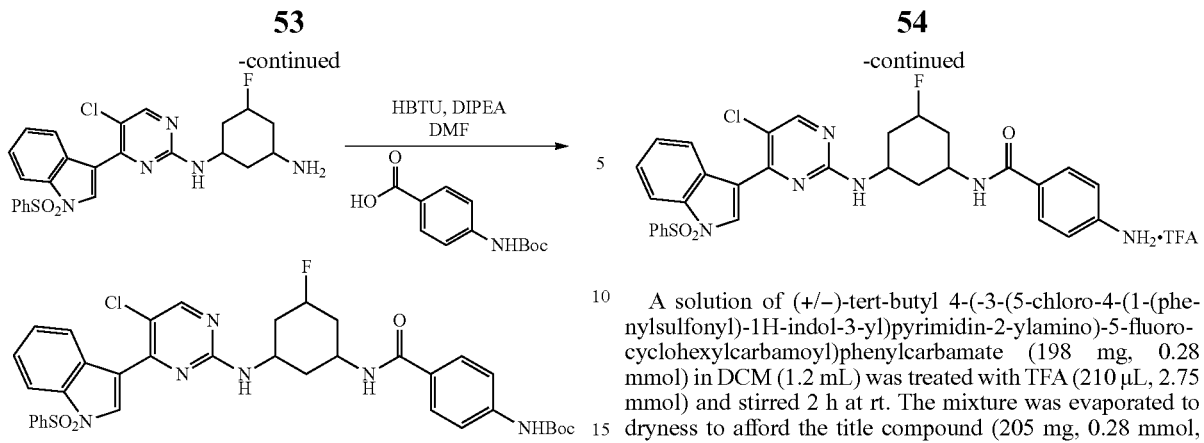

A solution of 3-(2,5-dichloropyrimidin-4-yl)-1-(phenylsulfonyl)-1H-indole (180 mg, 0.45 mmol), (+/−)-5-fluorocyclohexane-1,3-diamine (77 mg, 0.58 mmol) and DIPEA (101 μL, 3.54 mmol) in NMP (3 mL) was heated at 135° C. (mW) for 25 min. The cooled mixture was then treated with 4-(tert-butoxycarbonylamino)benzoic acid (93 mg, 0.45 mmol), HBTU (338 mg, 0.89 mmol), and DIPEA (0.23 mL, 1.34 mmol). The resulting mixture was stirred overnight at rt and then diluted with EtOAc (30 mL) and saturated NaHCO₃ (10 mL). The layers were separated and the aqueous layer was extracted with EtOAc (3×10 mL). The combined organic layers were washed with brine (10 mL), dried over MgSO₄, filtered, and evaporated to dryness. The residue was purified by SiO₂ chromatography (Hex/EtOAc 0 to 100% gradient) to afford the title compound (198 mg, 0.275 mmol, 62%) as a brownish solid.

(+/−)-4-amino-N-(3-(5-chloro-4-(1-(phenylsulfonyl)-1H-indol-3-yl)pyrimidin-2-ylamino)-5-fluorocyclohexyl)benzamide.TFA -continued A solution of (+/−)-tert-butyl 4-(-3-(5-chloro-4-(1-(phenylsulfonyl)-1H-indol-3-yl)pyrimidin-2-ylamino)-5-fluorocyclohexylcarbamoyl)phenylcarbamate (198 mg, 0.28 mmol) in DCM (1.2 mL) was treated with TFA (210 μL, 2.75 mmol) and stirred 2 h at rt. The mixture was evaporated to dryness to afford the title compound (205 mg, 0.28 mmol, 100%) as a pale yellow solid which was used in the next step without further purification.

(+/−)-4-amino-N-(3-(5-chloro-4-(1H-indol-3-yl)pyrimidin-2-ylamino)-5-fluorocyclohexyl)benzamide

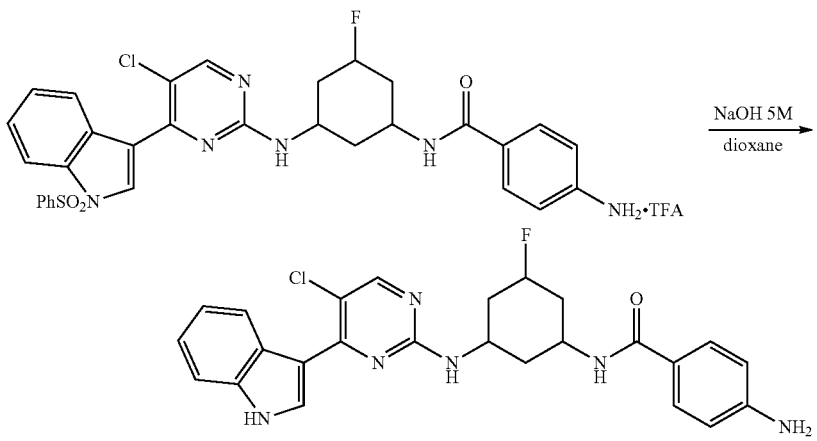

A solution of (+/−)-4-amino-N-(3-(5-chloro-4-(1-(phenylsulfonyl)-1H-indol-3-yl)pyrimidin-2-ylamino)-5-fluorocyclohexyl)benzamide.TFA (256 mg, 0.36 mmol) in dioxane (2.4 mL) was treated with a 5M solution of NaOH in H₂O (1.43 mL, 7.15 mmol) and heated at 75° C. overnight. The cooled mixture was evaporated to dryness and the resulting solid was suspended in H₂O (2 mL) and filtered. The solid was washed with H₂O (2×2 ml) and dried under high vacuum to afford the title compound (96 mg, 0.208 mmol, 58%) as a white solid which was used in the next step without further purification.

4-amino-N-((1R,3 S,5S)-3-(5-chloro-4-(1H-indol-3-yl)pyrimidin-2-ylamino)-5-fluorocyclohexyl)benzamide

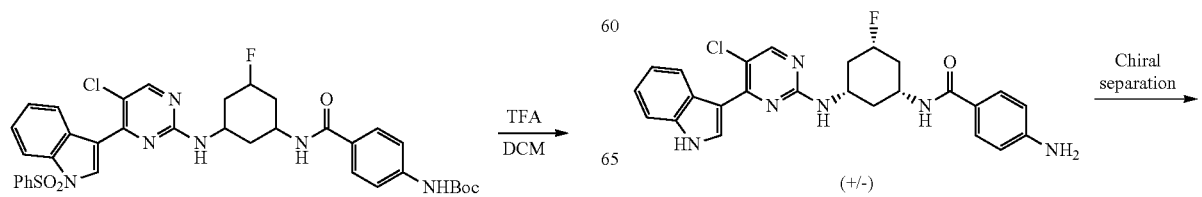

-continued

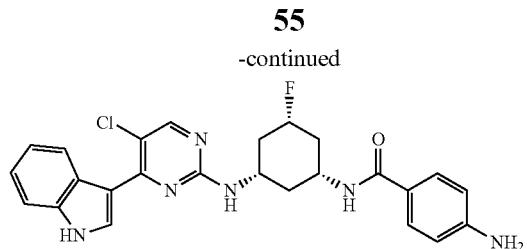

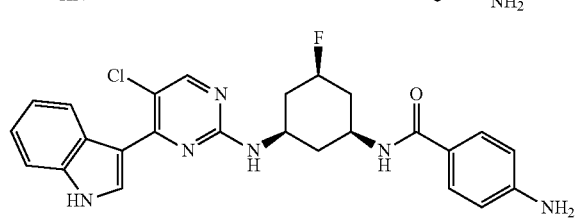

Both enantiomers of (+/−)-4-amino-N-(3-(5-chloro-4-(1H-indol-3-yl)pyrimidin-2-ylamino)-5-fluorocyclohexyl) benzamide (76 mg, 0.165 mmol) were separated using preparative chiral HPLC (ChiralPak IB, 5 μm, 20×250 mm; Hex/MeOH/DCM 70/15/15) and afforded the title compound (21.9 mg, 0.047, 29%) as a white solid.

Example 9. 4-amino-N-(5-(5-chloro-4-(1H-indol-3-yl)pyrimidin-2-ylamino)bicyclo[3.1.1]heptan-1-yl) benzamide (Compound 104)

$N^1$-(5-chloro-4-(1-(phenylsulfonyl)-1H-indol-3-yl) pyrimidin-2-yl)bicyclo[3.1.1]heptane-1,5-diamine

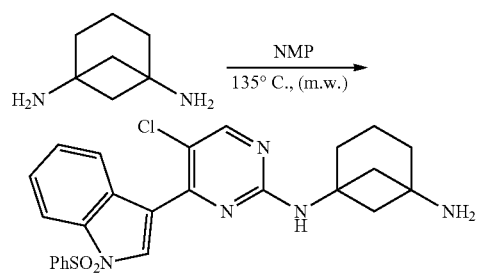

A solution of 3-(2,5-dichloropyrimidin-4-yl)-1-(phenylsulfonyl)-1H-indole (300 mg, 0.742 mmol), bicyclo[3.1.1]heptane-1,5-diamine (prepared as in WO2006012395) (120 mg, 0.951 mmol) and DIPEA (142 μL, 0.816 mmol) in NMP (5 mL) was heated at 135° C. (mW) for 2 h. The cooled mixture was diluted with EtOAc (30 mL), washed with H₂O (10 mL), brine (10 mL), dried over MgSO₄, filtered, and evaporated to dryness. The residue was purified by SiO₂ chromatography (DCM/MeOH 0 to 20% gradient) to afford the title compound (202 mg, 0.409 mmol, 55%) as a yellow foam.

tert-butyl 4-(5-(5-chloro-4-(1-(phenylsulfonyl)-1H-indol-3-yl)pyrimidin-2-ylamino)bicyclo[3.1.1]heptan-1-ylcarbamoyl)phenylcarbamate

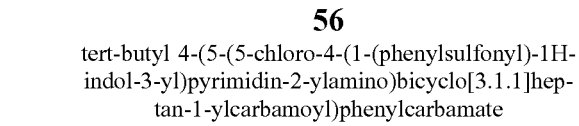

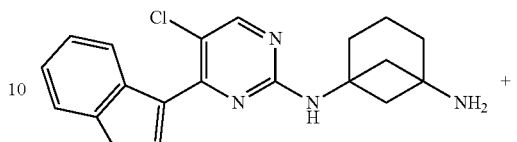

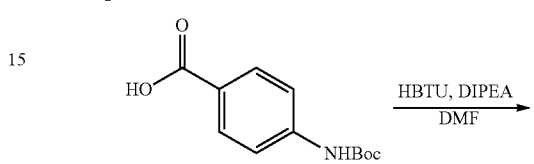

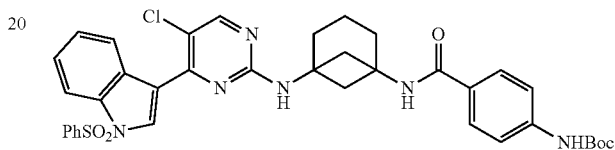

A solution of $N^1$-(5-chloro-4-(1-(phenylsulfonyl)-1H-indol-3-yl)pyrimidin-2-yl)bicyclo[3.1.1]heptane-1,5-diamine (202 mg, 0.409 mmol) and 4-(tert-butoxycarbonylamino) benzoic acid (116 mg, 0.491 mmol) in DMF (5.0 mL) was treated with HBTU (233 mg, 0.613 mmol) and DIPEA (105 μL, 0.818 mmol). The resulting mixture was stirred overnight at rt and diluted with EtOAc (30 mL) and saturated NaHCO₃ (15 mL). The layers were separated and the aqueous layer was extracted with EtOAc (2×30 mL). The combined organic layers were dried over MgSO₄, filtered, and evaporated to dryness to afford the title compound (291 mg, 0.408 mmol, 100%) as a brown oil which was used in the next step without further purification.

4-amino-N-(5-(5-chloro-4-(1-(phenylsulfonyl)-1H-indol-3-yl)pyrimidin-2-ylamino)bicyclo[3.1.1]heptan-1-yl)benzamide.TFA

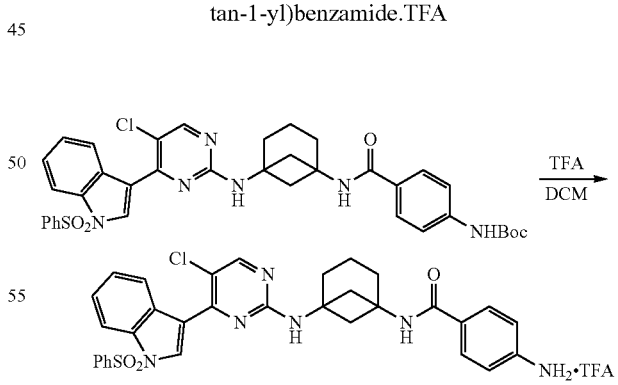

A solution of tert-butyl 4-(5-(5-chloro-4-(1-(phenylsulfonyl)-1H-indol-3-yl)pyrimidin-2-ylamino)bicyclo[3.1.1]heptan-1-ylcarbamoyl)phenylcarbamate (291 mg, 0.408 mmol) in DCM (4 mL) was treated with TFA (1.56 mL, 20.4 mmol) and stirred 1 h at rt. The mixture was evaporated to dryness to afford the title compound (250 mg, 0.408 mmol, 100%) as a yellowish oil.

4-amino-N-(5-(5-chloro-4-(1H-indol-3-yl)pyrimidin-2-ylamino)bicyclo[3.1.1]heptan-1-yl)benzamide

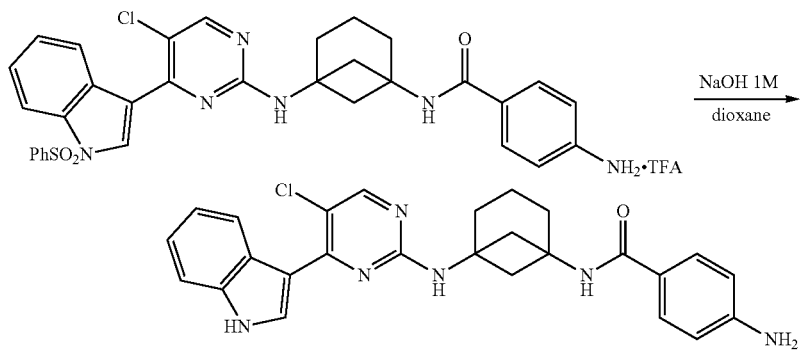

A solution of 4-amino-N-(5-(5-chloro-4-(1-(phenylsulfonyl)-1H-indol-3-yl)pyrimidin-2-ylamino)bicyclo[3.1.1]heptan-1-yl)benzamide.TFA (250 mg, 0.408 mmol) in dioxane (10 mL) was treated with a 1M solution of NaOH (6.0 mL, 6.0 mmol) and heated at 75° C. for 1 h. The cooled mixture was diluted with Me-THF (30 mL) and the organic layer was washed with H₂O (10 mL), dried over MgSO₄, filtered, and evaporated to dryness to afford the title compound (193 mg, 0.408 mmol, 100%) as a creamy solid.

Example 10. 4-amino-N-41R,5S)-5-(5-chloro-4-(1H-indol-3-yl)pyrimidin-2-ylamino)-3,3-difluorocyclohexyl)benzamide (Compound 115)

(+/−)-dibenzyl-5,5-difluorocyclohexane-1,3-diyldicarbamate

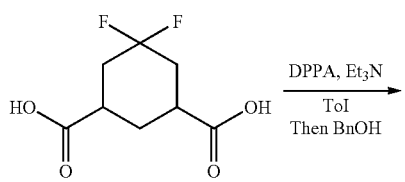

A solution of (+/−)-5,5-difluorocyclohexane-1,3-dicarboxylic acid (prepared as in WO2011005608) (454 mg, 2.18 mmol) in toluene (10 mL) was treated with Et₃N (670 µL, 4.80 mmol) and DPPA (940 µL, 4.36 mmol) and heated at 110° C. for 1 h. The solution was cooled to 80° C. and treated with Et₃N (670 µL, 4.80 mmol) and BnOH (500 µL, 4.80 mmol) and stirred overnight at this temperature. The cooled mixture was diluted with EtOAc (50 mL) and H₂O (20 mL). The layers were separated and the aqueous layer was extracted with EtOAc (3×20 mL). The combined organic layers were dried over MgSO₄, filtered, and evaporated to dryness. The residue was triturated with Hex (10 mL) followed by Et₂O (5 mL) and the solid was filtered and washed with Hex to afford the title compound (694 mg, 1.66 mmol, 76%) as a creamy solid which was used in the next step without further purification.

(+/−)-5,5-difluorocyclohexane-1,3-diamine

A degassed solution of (+/−)-dibenzyl-5,5-difluorocyclohexane-1,3-diyldicarbamate (694 mg, 1.66 mmol) in MeOH (100 mL) was treated with 10% Pd/C (100 mg) and stirred 5 h under H₂ (1 atm). The resulting mixture was filtered over celite (MeOH) and the filtrate was evaporated to dryness to afford the title compound (249 mg, 1.66 mmol, 100%) as a colorless oil which was used in the next step without further purification.

(+/−)-N¹-(5-chloro-4-(1-(phenylsulfonyl)-1H-indol-3-yl)pyrimidin-2-yl)-5,5-difluorocyclohexane-1,3-diamine A solution of 3-(2,5-dichloropyrimidin-4-yl)-1-(phenylsulfonyl)-1H-indole (560 mg, 1.380 mmol), (+/−)-5,5- difluorocyclohexane-1,3-diamine (249 mg, 1.658 mmol), and DIPEA (264 μL, 1.518 mmol) in NMP (15 mL) was heated at 135 (mW) for 40 min. The cooled mixture was diluted with EtOAc (50 mL), washed with H$_2$O (10 mL), brine (10 mL), dried over MgSO$_4$, filtered, and evaporated to dryness. The residue was purified by SiO$_2$ chromatography (DCM/MeOH 0 to 20% gradient) to afford the title compound (192 mg, 0.371 mmol, 27%) as a yellow foam.

(+/−)-tert-butyl 4-(5-(5-chloro-4-(1-(phenylsulfonyl)-1H-indol-3-yl)pyrimidin-2-ylamino)-3,3-difluorocyclohexylcarbamoyl)phenylcarbamate

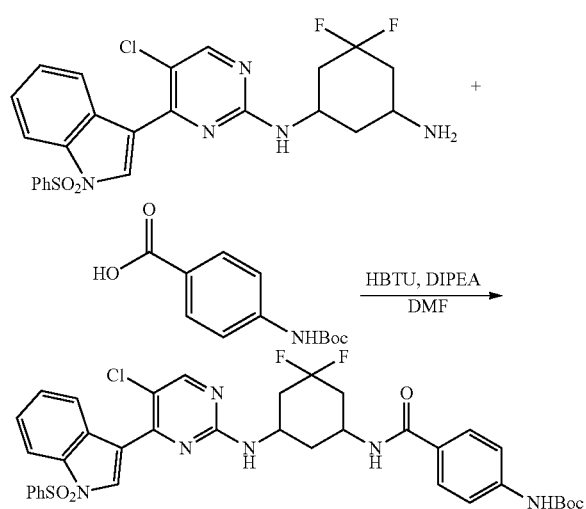

A solution of (+/−)-N$^1$-(5-chloro-4-(1-(phenylsulfonyl)-1H-indol-3-yl)pyrimidin-2-yl)-5,5-difluorocyclohexane-1,3-diamine (192 mg, 0.370 mmol) and 4-(tert-butoxycarbonylamino)benzoic acid (105 mg, 0.444 mmol) in DMF (6.0 mL) was treated with HBTU (211 mg, 0.555 mmol) and DIPEA (129 μL, 0.740 mmol). The resulting mixture was stirred overnight at rt and diluted with EtOAc (30 mL) and saturated NaHCO$_3$ (15 mL). The layers were separated and the aqueous layer was extracted with EtOAc (2×30 mL). The combined organic layers were dried over MgSO$_4$, filtered and evaporated to dryness to afford the title compound (272 mg, 0.370 mmol, 100%) as a brown oil which was used in the next step without further purification.

(+/−)-4-amino-N-(5-(5-chloro-4-(1-(phenylsulfonyl)-1H-indol-3-yl)pyrimidin-2-ylamino)-3,3-difluorocyclohexyl)benzamide.TFA

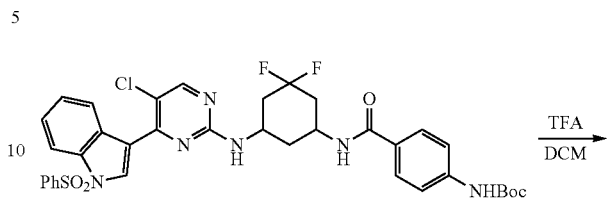

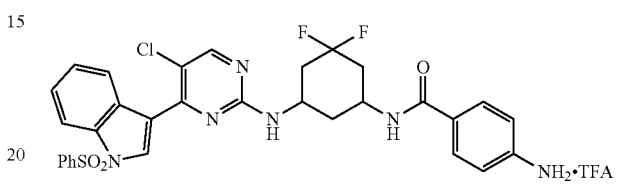

A solution of (+/−)-tert-butyl 4-(5-(5-chloro-4-(1-(phenylsulfonyl)-1H-indol-3-yl)pyrimidin-2-ylamino)-3,3-difluorocyclohexylcarbamoyl)phenylcarbamate (272 mg, 0.370 mmol) in DCM (4 mL) was treated with TFA (1.45 mL, 19.0 mmol) and stirred 2 h at rt. The resulting mixture was evaporated to dryness to afford the title compound (235 mg, 0.370 mmol, 100%) as a brownish oil which was used in the next step without further purification.

(+/−)-4-amino-N-(5-(5-chloro-4-(1H-indol-3-yl)pyrimidin-2-ylamino)-3,3-difluorocyclohexyl)benzamide

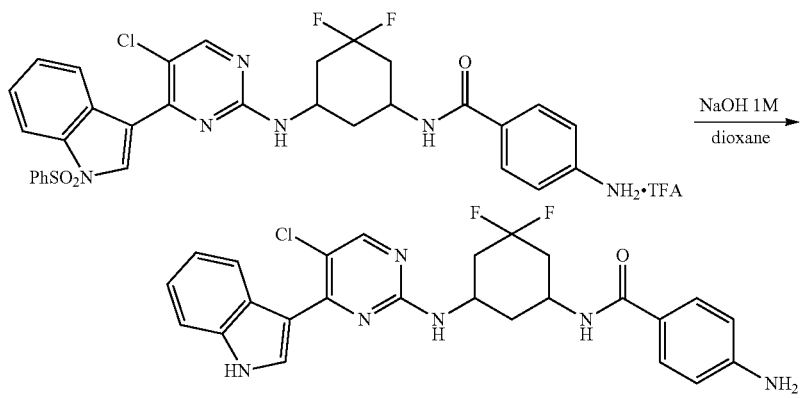

A solution of (+/−)-4-amino-N-(5-(5-chloro-4-(1-(phenylsulfonyl)-1H-indol-3-yl)pyrimidin-2-ylamino)-3,3-difluorocyclohexyl)benzamide.TFA (235 mg, 0.370 mmol) in dioxane (10 mL) was treated with a 1M solution of NaOH in H$_2$O (6.0 mL, 6.0 mmol) and heated at 75° C. for 2. The volatiles were removed by evaporation and the aqueous layer was extracted with MeTHF (30 mL). The organic layer was washed with H$_2$O (10 mL), dried over Na$_2$SO$_4$, filtered, and evaporated to dryness to afford the title compound (157 mg, 0.316 mmol, 85%) as a yellow solid which was used in the next step without further purification.

4-amino-N-((1R,5S)-5-(5-chloro-4-(1H-indol-3-yl)pyrimidin-2-ylamino)-3,3-difluorocyclohexyl)benzamide

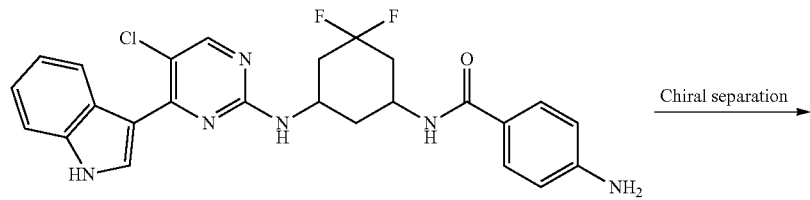

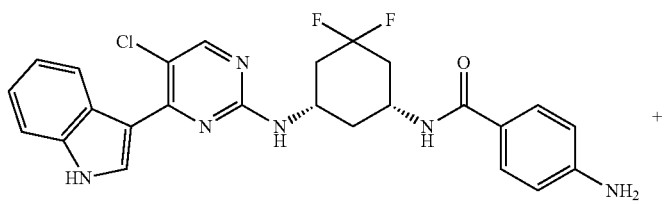

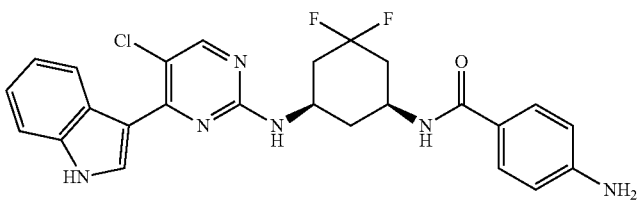

Both enantiomers of (+/−)-4-amino-N-(5-(5-chloro-4-(1H-indol-3-yl)pyrimidin-2-ylamino)-3,3-difluorocyclohexyl)benzamide (62 mg, 0.125 mmol) were separated using preparative chiral HPLC (ChiralPak IB, 5 μm, 20×250 mm; Hex/MeOH/DCM 64/18/18) and afforded the title compound (19.1 mg, 0.038, 31%) as a white solid.

Example 11. 4-amino-N-((1S,3R)-3-(5-chloro-4-(1H-indol-3-yl)pyrimidin-2-ylamino)cyclohexyl)benzenesulfonamide (Compound 109)

N-((1S,3R)-3-(5-chloro-4-(1-(phenylsulfonyl)-1H-indol-3-yl)pyrimidin-2-ylamino)cyclohexyl)-4-nitrobenzenesulfonamide

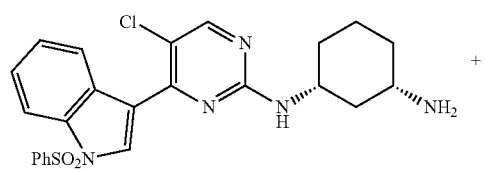

+

-continued

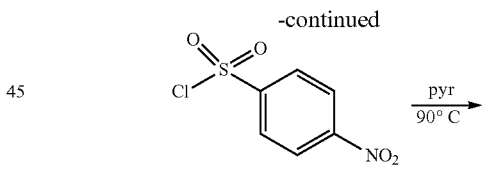

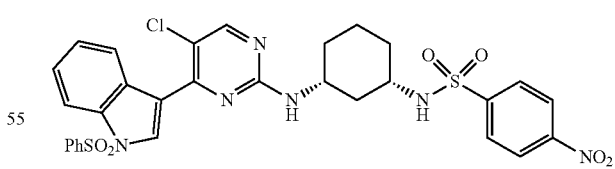

A solution of (1R,3S)—N1-(5-chloro-4-(1-(phenylsulfonyl)-1H-indol-3-yl)pyrimidin-2-yl)cyclohexane-1,3-diamine prepared as in example 3 (150 mg, 0.289 mmol) in pyr (2.2 mL) was treated with 4-nitrobenzene-1-sulfonyl chloride (64 mg, 0.289 mmol) and heated at 90° C. for 16 h. The cooled mixture was evaporated to dryness and the residue was purified by SiO₂ chromatography (DCM/EtOAc 0 to 100% gradient) to afford the title compound (147 mg, 0.220 mmol, 76%) as a yellow foam.

4-amino-N-((1S,3R)-3-(5-chloro-4-(1-(phenylsulfo-
nyl)-1H-indol-3-yl)pyrimidin-2-ylamino)cyclohexyl)
benzenesulfonamide

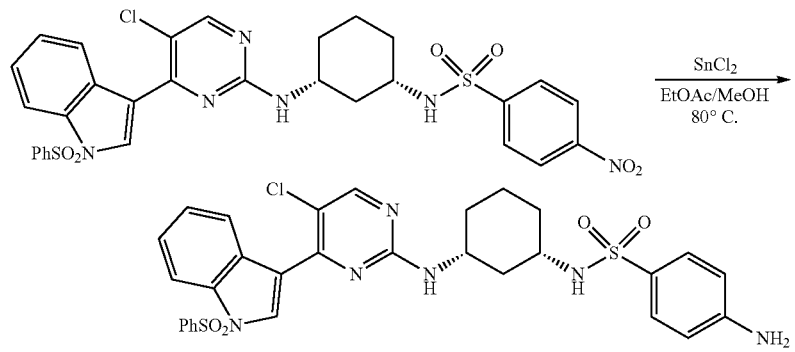

A solution of N-((1S,3R)-3-(5-chloro-4-(1-(phenylsulfo-nyl)-1H-indol-3-yl)pyrimidin-2-ylamino)cyclohexyl)-4-nitrobenzenesulfonamide (147 mg, 0.223 mmol) in 5/1 EtOAc/MeOH (4 mL) was treated with SnCl$_2$.10H$_2$O (126 mg, 0.557 mmol) and heated at 90° C. in a sealed tube for 4 h. The cooled mixture was diluted with saturated NaHCO$_3$ (10 mL), and then the mixture was stirred 20 min at rt followed by extraction of the aqueous layer with 4/1 CHCl$_3$/IPA (3×30 mL). The combined organic layers were washed with H$_2$O (10 mL), brine (10 mL), dried over MgSO$_4$, filtered through a pad of celite (4/1 CHCl$_3$/IPA), and evaporated to dryness. The residue was purified by SiO$_2$ chromatography (DCM/EtOAc 0 to 80% gradient) to afford the title compound (109 mg, 0.171 mmol, 77%) as a colorless oil.

4-amino-N-((1 S,3R)-3-(5-chloro-4-(1H-indol-3-yl)
pyrimidin-2-ylamino)cyclohexyl)benzenesulfona-
mide

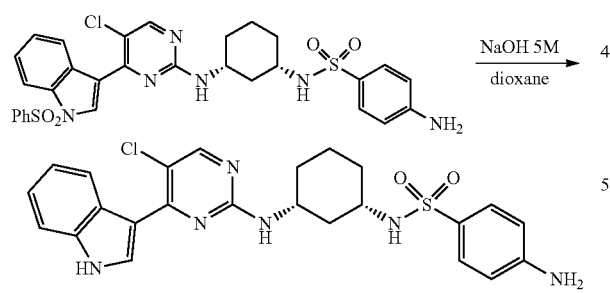

A solution of 4-amino-N-((1S,3R)-3-(5-chloro-4-(1-(phe-nylsulfonyl)-1H-indol-3-yl)pyrimidin-2-ylamino)cyclo-hexyl)benzenesulfonamide (109 mg, 0.171 mmol) in dioxane (3.4 mL) was treated with a 5M solution of NaOH in H$_2$O (0.17 μL, 0.855 mmol) and heated at 50° C. overnight. The cooled mixture was treated with a 1M solution of HCl in H$_2$O until a pH of 7 was reached, then the mixture was evaporated to dryness. The residue was purified by SiO$_2$ chromatography (DCM/MeOH 0 to 20% gradient) to afford the title compound (50 mg, 0.101 mmol, 59%) as a light yellow solid.

Example 12. 4-amino-N-((1S,3R)-3-(5-chloro-4-
(1H-indol-3-yl)pyrimidin-2-ylamino)cyclohexyl)-2-
fluorobenzamide (Compound 112)

N-((1S,3R)-3-(5-chloro-4-(1-(phenylsulfonyl)-1H-
indol-3-yl)pyrimidin-2-ylamino)cyclohexyl)-2-
fluoro-4-nitrobenzamide

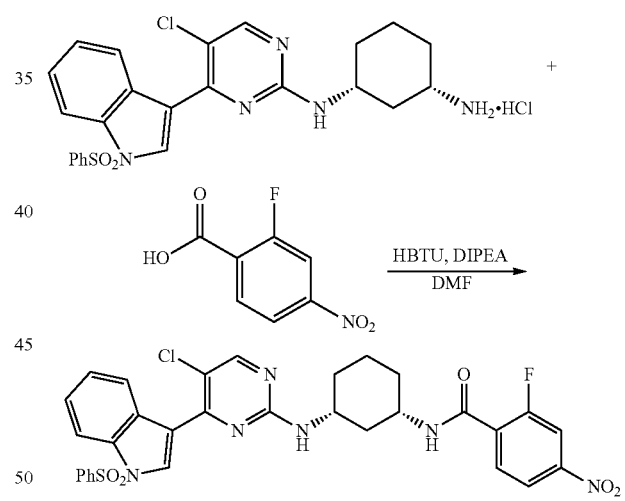

A solution of (1R,3S)—N1-(5-chloro-4-(1-(phenylsulfo-nyl)-1H-indol-3-yl)pyrimidin-2-yl)cyclohexane-1,3-di-amine.HCl prepared as in example 3 (150 mg, 0.29 mmol) and 2-fluoro-4-nitrobenzoic acid (54 mg, 0.29 mmol) in DCM (1.9 mL) was treated with HBTU (219 mg, 0.58 mmol) and DIPEA (150 μL, 0.870 mmol). The resulting mixture was stirred overnight at rt and diluted with EtOAc (30 mL) and saturated NaHCO$_3$ (15 mL). The layers were separated and the aqueous layer was extracted with EtOAc (2×30 mL). The combined organic layers were dried over MgSO$_4$, filtered, and evaporated to dryness. The residue was purified by SiO$_2$ chromatography (DCM/EtOAc 0 to 50% gradient) to afford the title compound (174 mg, 0.268 mmol, 93%) as a beige solid.

4-amino-N-((1S,3R)-3-(5-chloro-4-(1-(phenylsulfonyl)-1H-indol-3-yl)pyrimidin-2-ylamino)cyclohexyl)-2-fluorobenzamide

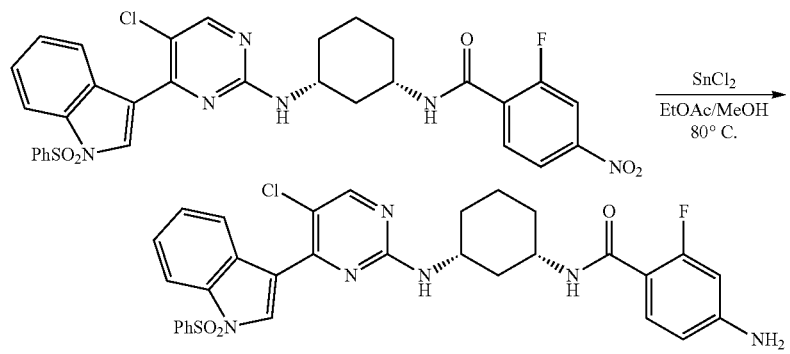

A solution of N-((1S,3R)-3-(5-chloro-4-(1-(phenylsulfonyl)-1H-indol-3-yl)pyrimidin-2-ylamino)cyclohexyl)-2-fluoro-4-nitrobenzamide (174 mg, 0.27 mmol) in 5/1 EtOAc/MeOH (5 mL) was treated with SnCl$_2$·10H$_2$O (151 mg, 0.67 mmol) and heated at 80° C. in a sealed tube for 5 h. The cooled mixture was diluted with saturated NaHCO$_3$ (10 mL), and the mixture was stirred 20 min at rt followed by extraction of the aqueous layer with EtOAc (3×30 mL). The combined organic layers were washed with H$_2$O (10 mL), brine (10 mL), dried over MgSO$_4$, filtered, and evaporated to dryness to afford the title compound (147 mg, 0.237 mmol, 88%) as a pale yellow solid which was used in the next step without further modification.

4-amino-N-((1S,3R)-3-(5-chloro-4-(1H-indol-3-yl)pyrimidin-2-ylamino)cyclohexyl)-2-fluorobenzamide

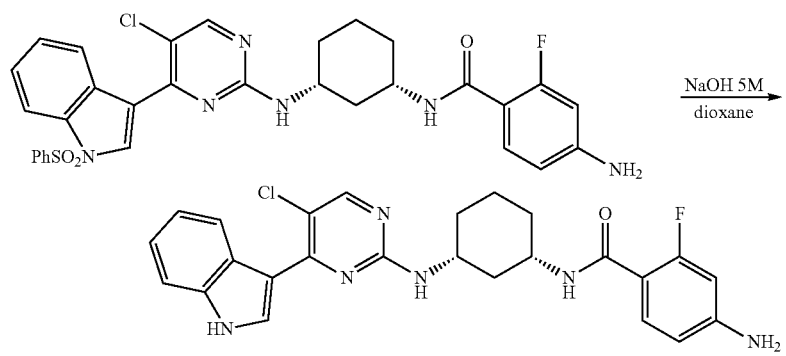

A solution of 4-amino-N-((1S,3R)-3-(5-chloro-4-(1-(phenylsulfonyl)-1H-indol-3-yl)pyrimidin-2-ylamino)cyclohexyl)-2-fluorobenzamide (146 mg, 0.24 mmol) in dioxane (1.6 mL) was treated with a 5M solution of NaOH in H$_2$O (940 µL, 4.72 mmol) and heated at 75° C. overnight. The cooled mixture was diluted with MeTHF (20 mL) and H$_2$O (10 mL). The layers were separated and the aqueous layer was extracted with MeTHF (3×15 mL). The combined organic layers were dried over MgSO$_4$, filtered, and evaporated to dryness. The residue was purified by SiO$_2$ chromatography (DCM/THF 0 to 60% gradient) to afford the title compound (98 mg, 0.205 mmol, 67%) as a white solid.

Example 13. 4-amino-N-((1S,3R)-3-(5-chloro-4-(1H-indol-3-yl)pyrimidin-2-ylamino)cyclohexyl)-3-fluorobenzamide (Compound 111)

4-amino-N-((1S,3R)-3-(5-chloro-4-(1-(phenylsulfonyl)-1H-indol-3-yl)pyrimidin-2-ylamino)cyclohexyl)-3-fluorobenzamide

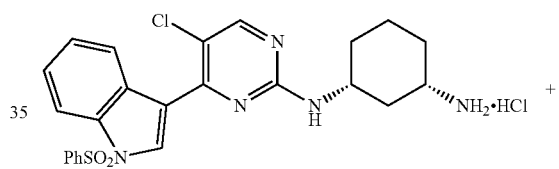

-continued

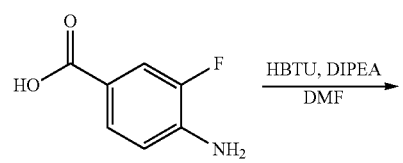

-continued

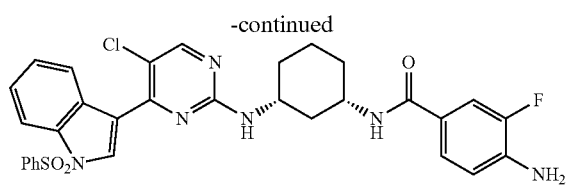

A solution of (1R,3S)—N1-(5-chloro-4-(1-(phenylsulfonyl)-1H-indol-3-yl)pyrimidin-2-yl)cyclohexane-1,3-diamine.HCl prepared as in example 3 (150 mg, 0.29 mmol) and 4-amino-3-fluorobenzoic acid (45 mg, 0.29 mmol) in DMF (1.9 mL) was treated with HBTU (219 mg, 0.58 mmol) and DIPEA (150 μL, 0.870 mmol). The resulting mixture was stirred overnight at rt and diluted with MeTHF (30 mL) and saturated NaHCO₃ (15 mL). The layers were separated and the aqueous layer was extracted with MeTHF (2×30 mL). The combined organic layers were dried over MgSO₄, filtered, and evaporated to dryness. The residue was purified by SiO₂ chromatography (DCM/EtOAc 0 to 100% gradient) to afford the title compound (178 mg, 0.287 mmol, 99%) as a pale yellow solid.

4-amino-N-((1 S,3R)-3-(5-chloro-4-(1H-indol-3-yl)pyrimidin-2-ylamino)cyclohexyl)-3-fluorobenzamide

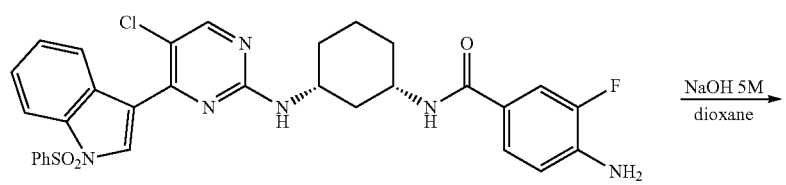

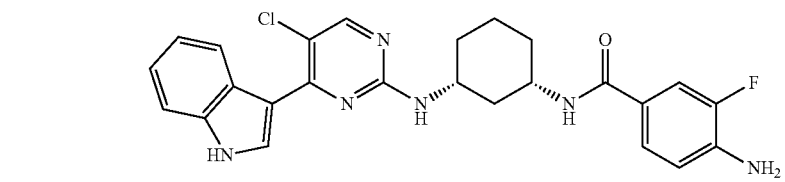

A solution of 4-amino-N4(1S,3R)-3-(5-chloro-4-(1-(phenylsulfonyl)-1H-indol-3-yl)pyrimidin-2-ylamino)cyclohexyl)-3-fluorobenzamide (179 mg, 0.29 mmol) in dioxane (1.9 mL) was treated with a 5M solution of NaOH in H₂O (1.16 mL, 5.78 mmol) and heated at 75° C. overnight. The cooled mixture was diluted with MeTHF (20 mL) and H₂O (10 mL). The layers were separated and the aqueous layer was extracted with MeTHF (3×15 mL). The combined organic layers were dried over MgSO₄, filtered, and evaporated to dryness. The residue was purified by SiO₂ chromatography (DCM/THF 0 to 60% gradient) to afford the title compound (89 mg, 0.185 mmol, 64%) as a white solid.

Example 14. (+/−)-4-amino-N-(3-(5-chloro-4-(1H-indol-3-yl)pyrimidin-2-ylamino)-1-methylcyclohexyl)benzamide (Compound 116)

tert-butyl (1R,3 S)-3-(Benzyloxycarbonylamino)-3-methylcyclohexylcarbamate

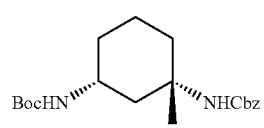

A solution of (1S,3R)-3-(tert-butoxycarbonylamino)-1-methylcyclohexane-carboxylic acid (prepared as in WO2010/148197, 100 mg, 0.389 mmol) in toluene (1.5 mL) was treated with Et₃N (60 μL, 0.43 mmol) and DPPA (84 μL, 0.39 mmol) and heated at 110° C. for 1 h. The mixture was cooled down to 80° C., treated with benzyl alcohol (42 μL, 0.41 mmol) and Et₃N (60 μL, 0.43 mmol). The resulting mixture was heated at 80° C. for 20 h. The cooled mixture was then diluted with EtOAc (20 mL) and H₂O (10 mL). The layers were separated and the aqueous layer was extracted with EtOAc (3×10 mL). The combined organics layers were washed with brine (10 mL), filtered, and evaporated to dryness. The residue was purified by SiO₂ chromatography (Hex/EtOAc 0 to 50% gradient) to afford the title compound (59 mg, 0.180 mmol, 46%) as a colorless oil.

(+/−)-benzyl-3-amino-1-methylcyclohexylcarbamate.HCl

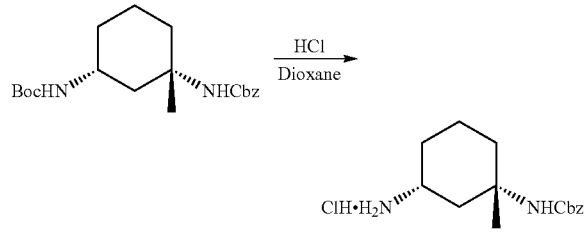

A solution of tert-butyl (1R,3S)-3-(benzyloxycarbonylamino)-3-methylcyclohexylcarbamate (45 mg, 0.124 mmol) in DCM (0.6 mL) was treated with a 4M solution of HCl in dioxane (620 μL, 2.48 mmol) and stirred 1 h at rt. The mixture was evaporated to dryness to afford the title compound (37 mg, 0.124 mmol, 100%) as a white solid which was used in the next step without further purification.

(+/−)-benzyl-3-(5-chloro-4-(1-(phenylsulfonyl)-1H-indol-3-yl)pyrimidin-2-ylamino)-1-methylcyclohexylcarbamate

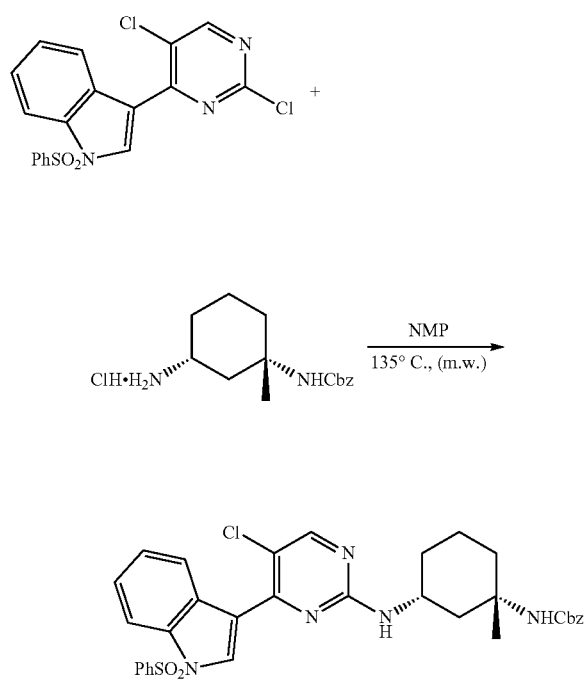

A solution of 3-(2,5-dichloropyrimidin-4-yl)-1-(phenylsulfonyl)-1H-indole (63 mg, 0.155 mmol), (+/−)-benzyl-3-amino-1-methylcyclohexylcarbamate.HCl (37 mg, 0.124 mmol) and DIPEA (44 μL, 0.254 mmol) in NMP (0.5 mL) was heated at 135° C. (mW) for 25 min. The cooled mixture was diluted with EtOAc (20 mL), washed with H₂O (5 mL), brine (5 mL), dried over MgSO₄, filtered, and evaporated to dryness. The residue was purified by SiO₂ chromatography (DCM/EtOAc 0 to 30% gradient) to afford the title compound (52 mg, 0.083 mmol, 66%) as a yellow foam.

(+/−)-N1-(5-chloro-4-(1-(phenylsulfonyl)-1H-indol-3-yl)pyrimidin-2-yl)-3-methylcyclohexane-1,3-diamine

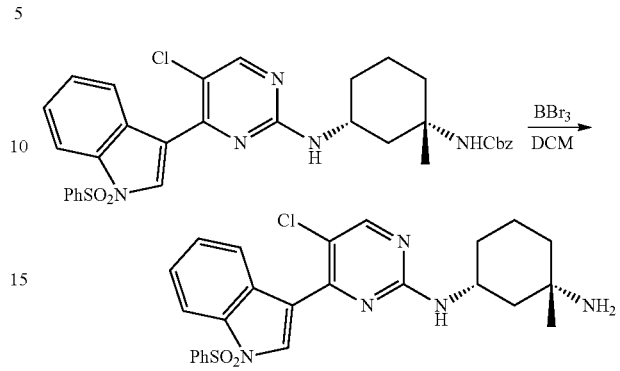

A cooled (−78° C.) solution of (+/−)-benzyl-3-(5-chloro-4-(1-(phenylsulfonyl)-1H-indol-3-yl)pyrimidin-2-ylamino)-1-methylcyclohexylcarbamate (51 mg, 0.081 mmol) in DCM (0.32 mL) was treated with a 1M solution of BBr₃ in DCM (97 μL, 0.097 mmol) and was slowly warmed to rt. MeOH (1 ML) was added to the mixture was the resulting solution was stirred 1 h at rt. The resulting mixture was evaporated to dryness to afford the title compound (40 mg, 0.081 mmol, 100%) as a yellow solid which was used in the next step without further purification.

(+/−)-tert-butyl 4-(3-(5-chloro-4-(1-(phenylsulfonyl)-1H-indol-3-yl)pyrimidin-2-ylamino)-1-methylcyclohexylcarbamoyl)phenylcarbamate

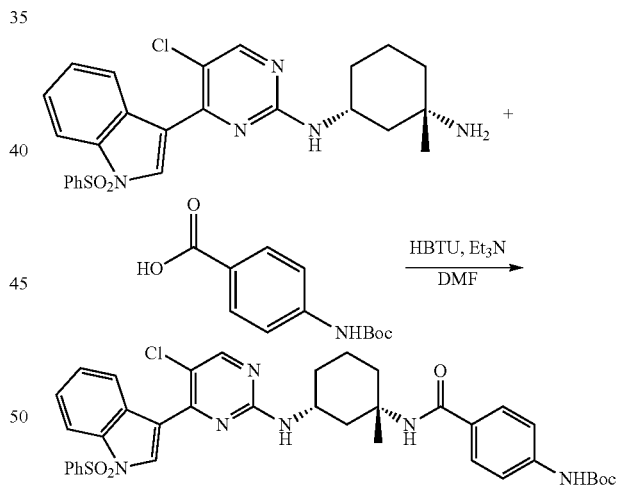

A solution of (+/−)-benzyl-3-(5-chloro-4-(1-(phenylsulfonyl)-1H-indol-3-ylamino)-1-methylcyclohexylcarbamate (40 mg, 0.81 mmol) and 4-(tert-butoxycarbonylamino)benzoic acid (23 mg, 0.97 mmol) in DMF (0.4 mL) was treated with HBTU (46 mg, 0.121 mmol) and Et₃N (34 μL, 0.242 mmol). The resulting mixture was stirred overnight at rt and diluted with EtOAc (10 mL) and saturated NaHCO₃ (10 mL). The layers were separated and the aqueous layer was extracted with EtOAc (2×10 mL). The combined organic layers were dried over MgSO₄, filtered, and evaporated to dryness. The residue was purified by SiO₂ chromatography (DCM/EtOAc 0 to 100% gradient) to afford the title compound (48 mg, 0.067 mmol, 83%) as a beige solid.

(+/−)-tert-butyl 4-(3-(5-chloro-4-(1H-indol-3-yl)
pyrimidin-2-ylamino)-1-methylcyclohexylcarbam-
oyl)phenylcarbamate

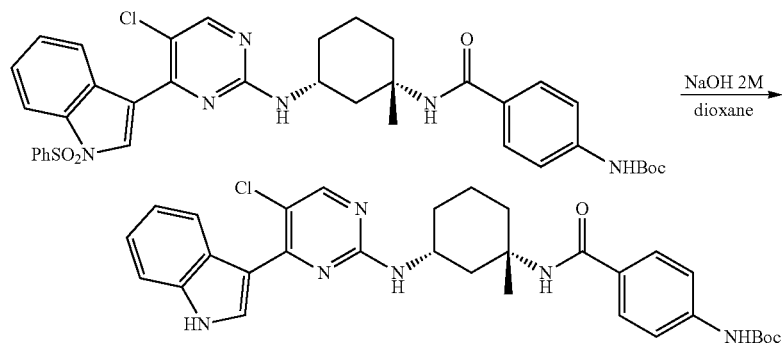

A solution of (+/−)-tert-butyl 4-(3-(5-chloro-4-(1-(phe-nylsulfonyl)-1H-indol-3-yl)pyrimidin-2-ylamino)-1-methylcyclohexylcarbamoyl)phenylcarbamate (45 mg, 0.063 mmol) in dioxane (0.6 mL) was treated with a 2M solution of NaOH in $H_2O$ (472 µL, 0.944 mmol) and heated at 60° C. for 1 h. The cooled mixture was diluted with MeTHF (20 mL) and $H_2O$ (10 mL). The layers were separated and the aqueous layer was extracted with MeTHF (3×10 mL). The combined organic layers were dried over $MgSO_4$, filtered, and evaporated to dryness to afford the title compound (36 mg, 0.063 mmol, 100%) as a yellow solid which was used in the next step without further purification.

(+/−)-4-amino-N-(3-(5-chloro-4-(1H-indol-3-yl)
pyrimidin-2-ylamino)-1-methylcyclohexyl)benz-
amide

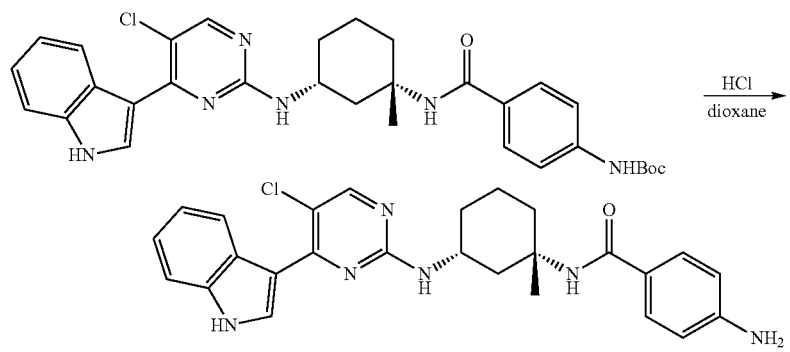

A solution of (+/−)-tert-butyl 4-(3-(5-chloro-4-(1H-indol-3-yl)pyrimidin-2-ylamino)-1-methylcyclohexylcarbamoyl)phenylcarbamate (36 mg, 0.063 mmol) in DCM was treated with a 4M solution of HCl in dioxane (235 µL, 0.939 mmol) and stirred overnight at rt. The resulting mixture was diluted with MeTHF (10 mL) and saturated $NaHCO_3$ (5 mL). The layers were separated and the aqueous layer was extracted with MeTHF (3×10 mL). The combine organic layers were dried over $MgSO_4$, filtered, and evaporated to dryness to afford the title compound (30 mg, 0.063 mmol, 100%) as a pale yellow solid.

Example 15. N-((1S,3R)-3-(4-(1H-indol-3-yl)pyrimidin-2-ylamino)cyclohexyl)-4-aminobenzamide (Compound 114)

tert-butyl 4-((1S,3R)-3-(4-(1H-indol-3-yl)pyrimidin-2-ylamino)cyclohexylcarbamoyl)phenylcarbamate

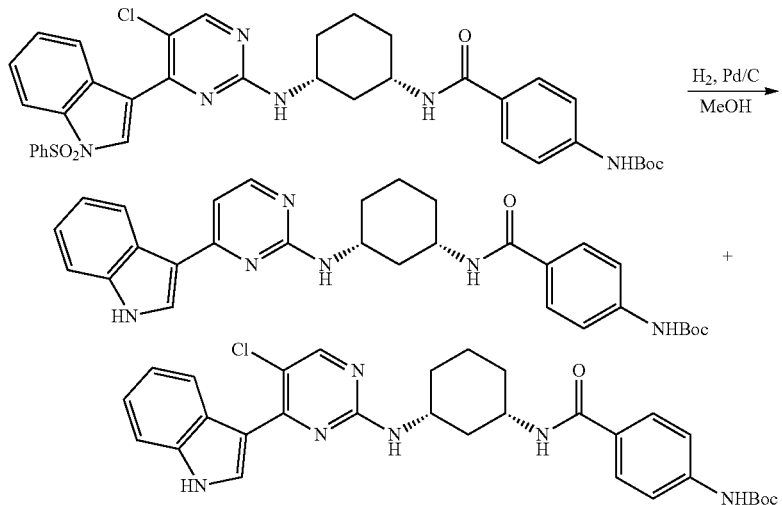

A degassed solution of tert-butyl 4-((1S,3R)-3-(5-chloro-4-(1-(phenylsulfonyl)-1H-indol-3-yl)pyrimidin-2-ylamino)cyclohexylcarbamoyl)phenylcarbamate prepared as in example 3 (148 mg, 0.211 mmol) in MeOH (10 mL) was treated with 10% Pd/C (25 mg) and stirred overnight under H$_2$ (50 psi). The resulting mixture was filtered over celite (MeOH) and the filtrate was evaporated to dryness affording an inseparable mixture of the title compound and chlorinated pyrimidine which was used in the next step without purification.

N-((1S,3R)-3-(4-(1H-indol-3-yl)pyrimidin-2-ylamino)cyclohexyl)-4-aminobenzamide

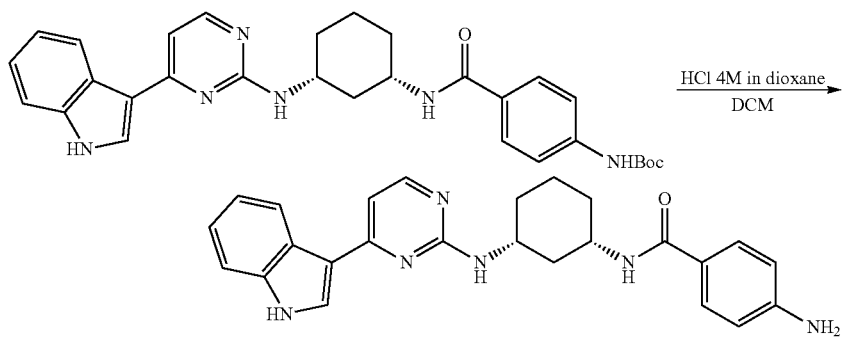

A solution of tert-butyl 4-((1S,3R)-3-(4-(1H-indol-3-yl)pyrimidin-2-ylamino)cyclohexylcarbamoyl)phenylcarbamate (100 mg, as a mixture with chlorinated pyrimidine from previous step) in DCM (2.0 mL) was treated with a 4M solution of HCl in dioxane (750 mL, 3.0 mmol) and stirred 4 h at rt. The mixture was evaporated to dryness and the residue was purified by reverse phase chromatography (C$_{18}$, H$_2$O/ACN+0.1% HCO$_2$H 5 to 60% gradient) to afford the title compound (12.5 mg, 0.0081 mmol, 25%) as a white solid.

Example 16. 4-amino-N-((1S,3R)-3-(5-chloro-4-(1H-indol-3-yl)pyrimidin-2-ylamino)cyclohexyl)-2-morpholinobenzamide (Compound 117)

2-morpholino-4-nitrobenzoic acid

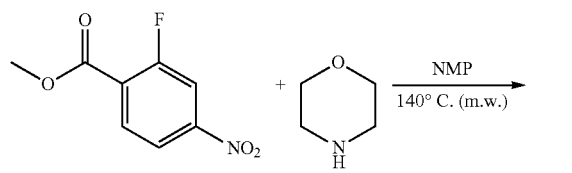

A solution of methyl 2-fluoro-4-nitrobenzoate (200 mg, 1.00 mmol) and morpholine (703 µL, 8.04 mmol) in NMP (2.1 mL) was heated at 140° C. (mW) for 35 min. The cooled mixture was diluted with EtOAc (20 mL) and washed with H₂O (10 mL) and brine (10 ml). The combined aqueous layers were acidified to pH=2 with a 1M solution of HCl in H₂O and extracted with DCM (3×20 mL). The combined organic layers were dried by passing through a phase cartridge separator and evaporated to dryness to afford the title compound as a mixture with morpholine which was used in the next step without further purification.

N-((1S,3R)-3-(5-chloro-4-(1-(phenylsulfonyl)-1H-indol-3-yl)pyrimidin-2-ylamino)cyclohexyl)-2-morpholino-4-nitrobenzamide

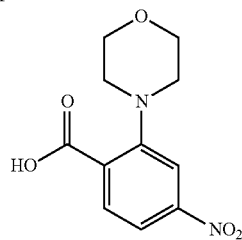

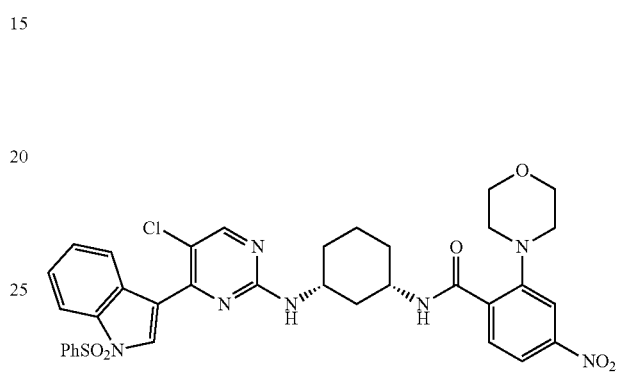

A solution of (1R,3S)—N1-(5-chloro-4-(1-(phenylsulfonyl)-1H-indol-3-yl)pyrimidin-2-yl)cyclohexane-1,3-diamine prepared as in example 3 (50 mg, 0.104 mmol) and 2-morpholino-4-nitrobenzoic acid (29 mg, 0.114 mmol) in DMF (5.0 mL) was treated with Et₃N (43 µL, 0.311 mmol) and HBTU (59 mg, 0.156 mmol). The resulting mixture was stirred overnight at rt, diluted with EtOAc (20 mL) and saturated NaHCO₃ (10 mL). The layers were separated and the organic layer was washed with brine (10 mL), dried over MgSO₄, filtered, and evaporated to dryness. The residue was purified by SiO₂ chromatography (DCM/EtOAc 0 to 70% gradient) to afford the title compound (48 mg, 0.067 mmol, 65%) as a pale yellow solid.

4-amino-N-((1S,3R)-3-(5-chloro-4-(1-(phenylsulfonyl)-1H-indol-3-yl)pyrimidin-2-ylamino)cyclohexyl)-2-morpholinobenzamide -continued

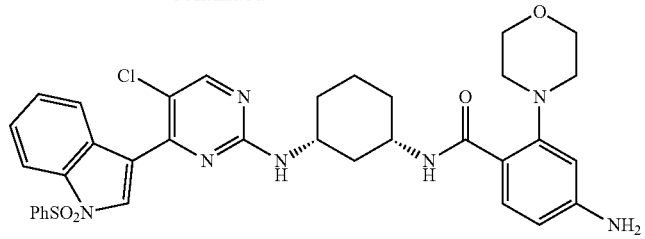

A cooled (0° C.) solution of N-((1S,3R)-3-(5-chloro-4-(1-(phenylsulfonyl)-1H-indol-3-yl)pyrimidin-2-ylamino)cyclohexyl)-2-morpholino-4-nitrobenzamide (76 mg, 0.106 mmol) in 2/1 MeOH/THF (1 mL) was sequentially treated with NiCl$_2$.6H$_2$O (12.6 mg, 0.053 mmol) and NaBH$_4$ (16.1 mg, 0.425 mmol). The black resulting mixture was stirred 15 min at rt before dilution with EtOAc (20 mL) and H$_2$O (10 mL). The layers were separated and the aqueous layer was extracted with EtOAc (3×10 mL). The combined organic layers were washed with brine (10 mL), dried over MgSO$_4$, filtered, and evaporated to dryness. The residue was purified by SiO$_2$ chromatography (DCM/EtOAc 0 to 70% gradient) to afford the title compound (26 mg, 0.038 mmol, 36%) as a pale yellow solid.

4-amino-N-((1S,3R)-3-(5-chloro-4-(1H-indol-3-yl)pyrimidin-2-ylamino)cyclohexyl)-2-morpholinobenzamide

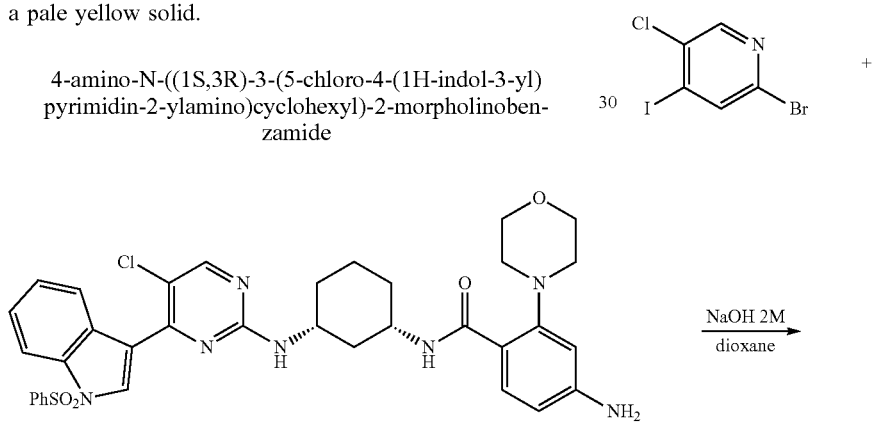

A solution of 4-amino-N-((1S,3R)-3-(5-chloro-4-(1-(phenylsulfonyl)-1H-indol-3-yl)pyrimidin-2-ylamino)cyclohexyl)-2-morpholinobenzamide (24 mg, 0.035 mmol) in dioxane (0.35 mL) was treated with a 2M solution of NaOH in H$_2$O (262 µL, 0.525 mmol) and stirred overnight at rt and 2 h at 60° C. The cooled mixture was concentrated to remove volatiles and the resulting residue was diluted with MeTHF (15 mL) and H$_2$O (10 mL). The layers were separated and the aqueous layer was extracted with MeTHF (3×10 mL). The combined organic layers were dried over Na$_2$SO$_4$, filtered, and evaporated to dryness to afford the title compound (19 mg, 0.0248 mmol, 71%) as a pale yellow solid.

Example 17. 4-amino-N-((1S,3R)-3-(5-chloro-4-(1H-indol-3-yl)pyridin-2-ylamino)cyclohexyl)benzamide (Compound 118)

3-(2-bromo-5-chloropyridin-4-yl)-1-(phenylsulfonyl)-1H-indole

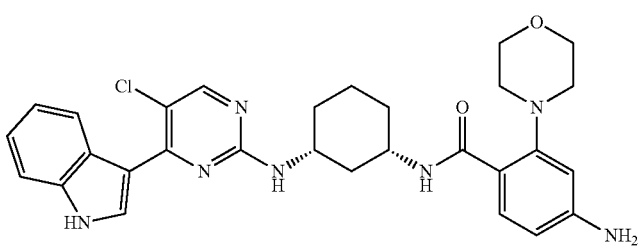

-continued

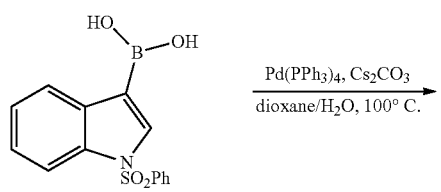

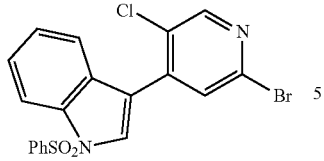

A degassed solution of 2-bromo-5-chloro-4-iodopyridine (500 mg, 1.57 mmol), 1-(phenylsulfonyl)-1H-indol-3-ylboronic acid (497 mg g, 1.65 mmol), Cs₂CO₃ (1.023 g, 3.14 mmol) and Pd(PPh₃)₄ (181 mg, 0.16 mmol) in 2/1 dioxane/H₂O (52 ml) was heated at 100° C. for 3 h. The cooled mixture was diluted with EtOAc (50 mL) and saturated NaHCO₃ (20 ml). The layers were separated and the aqueous layer was extracted with EtOAc (3×20 mL). The combined organic layers were washed with brine (20 mL), dried over MgSO₄ and evaporated to dryness. The residue was purified by SiO₂ chromatography (Hex/EtOAc 5 to 70% gradient) and afforded the title compound (373 mg, 0.836 mmol, 53%) as a pale yellow solid.

Benzyl (1S,3R)-3-(5-chloro-4-(1-(phenylsulfonyl)-1H-indol-3-yl)pyridin-2-ylamino)cyclohexylcarbamate

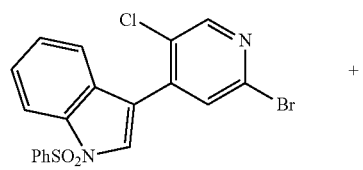

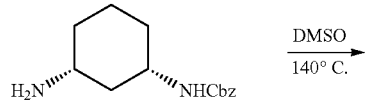

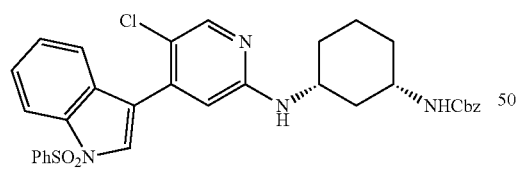

A solution of 3-(2-bromo-5-chloropyridin-4-yl)-1-(phenylsulfonyl)-1H-indole (151 mg, 0.34 mmol) and benzyl (1S,3R)-3-aminocyclohexylcarbamate prepared as in example 8 (167 mg, 0.67 mmol) in DMSO (2.0 mL) was heated at 140° C. for 24 h. The cooled mixture was diluted with DCM (50 ml) and H₂O (50 ml). The layers were separated and the aqueous layer was extracted with DCM (3×20 mL). The combined organic layers were washed with H₂O (20 mL), brine (20 mL), dried over MgSO₄, filtered, and evaporated to dryness. The residue was purified by SiO₂ chromatography (DCM/MeOH 0 to 10% gradient) to afford the title compound (43 mg, 0.070 mmol, 21%) as a white solid.

(1R,3S)—N1-(5-chloro-4-(1-(phenylsulfonyl)-1H-indol-3-yl)pyridin-2-yl)cyclohexane-1,3-diamine

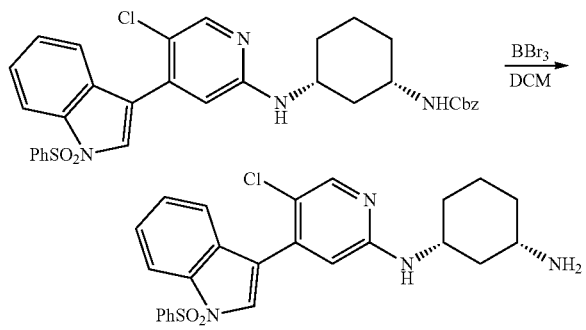

A cooled (−78° C.) solution of benzyl (1S,3R)-3-(5-chloro-4-(1-(phenylsulfonyl)-1H-indol-3-yl)pyridin-2-ylamino)cyclohexylcarbamate (42 mg, 0.068 mmol) in DCM (1.0 mL) was treated with a 1M solution of BBr₃ in DCM (82 µL, 0.082 mmol) and stirred for 1 h, then warmed up to rt, and stirred for an additional 3 h. The resulting mixture was treated with MeOH (2 mL) and the solution was evaporated to dryness. The residue was purified by reverse phase chromatography (C₁₈, H₂O/ACN+0.1% HCO₂H 0 to 100% gradient) to afford the title compound (10 mg, 0.021 mmol, 31%) as a pale yellow solid.

tert-butyl 4-((1S,3R)-3-(5-chloro-4-(1-(phenylsulfonyl)-1H-indol-3-ylamino)cyclohexylcarbamoyl)phenylcarbamate

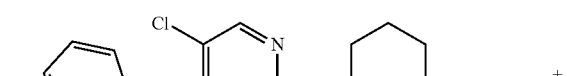

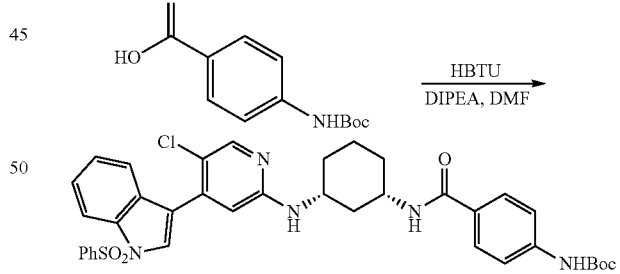

A solution of (1R,3S)—N1-(5-chloro-4-(1-(phenylsulfonyl)-1H-indol-3-yl)pyridin-2-yl)cyclohexane-1,3-diamine (10 mg, 0.021 mmol) and 4-(tert-butoxycarbonylamino)benzoic acid (5.9 mg, 0.025 mmol) in DMF (2.0 mL) was treated with DIPEA (5.4 µL, 0.031 mmol) and HBTU (5.4 mg, 0.031 mmol). The resulting mixture was stirred overnight at rt, diluted with EtOAc (5 mL) and saturated NaHCO₃ (5 mL). The layers were separated and the organic layer was washed with brine (5 mL), dried over MgSO₄, filtered, and evaporated to dryness to afford the title compound (14.6 mg, 0.021 mmol, 100%) as a pale yellow solid which was used in the next step without further purification.

4-amino-N-((1S,3R)-3-(5-chloro-4-(1H-indol-3-yl)pyridin-2-ylamino)cyclohexyl)benzamide

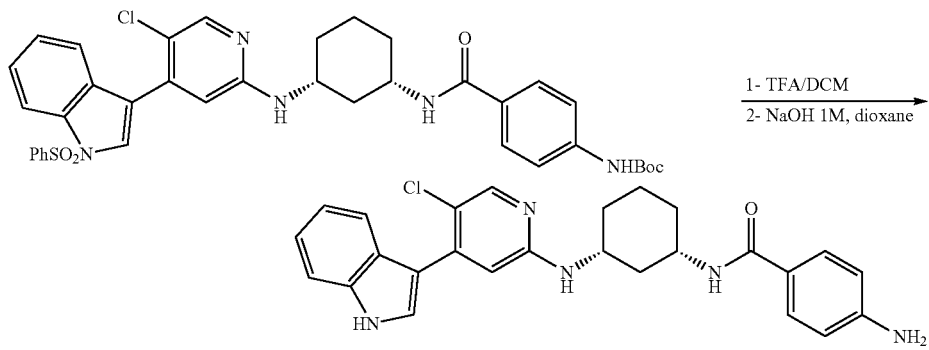

A solution of tert-butyl 44(1S,3R)-3-(5-chloro-4-(1-(phenylsulfonyl)-1H-indol-3-yl)pyridin-2-ylamino)cyclohexylcarbamoyl)phenylcarbamate (14.6 mg, 0.021 mmol) in DCM (2 mL) was treated with TFA (82 µL, 1.07 mmol) and stirred 3 h at rt. The resulting solution was evaporated to dryness, dissolved in dioxane (1 mL), treated with a 1M solution of NaOH in H$_2$O (315 µL, 0.315 mmol), and heated at 70° C. for 3 h. The cooled mixture was evaporated to dryness and the residue was diluted with MeTHF (10 mL) and H$_2$O (5 mL). The layers were separated and the aqueous layer was extracted with MeTHF (4×5 mL). The combined organic layers were dried over Na$_2$SO$_4$, filtered, and evaporated to dryness, affording the title compound (9.6 mg, 0.20 mmol, 94%) as a white gum.

Example 18. 3-amino-N-(trans-4-(5-chloro-4-(1H-indol-3-yl)pyrimidin-2-ylamino)cyclohexyl)benzamide.HCl (Compound 119)

(trans)-N1-(5-chloro-4-(1-(phenylsulfonyl)-1H-indol-3-yl)pyrimidin-2-yl)cyclohexane-1,4-diamine

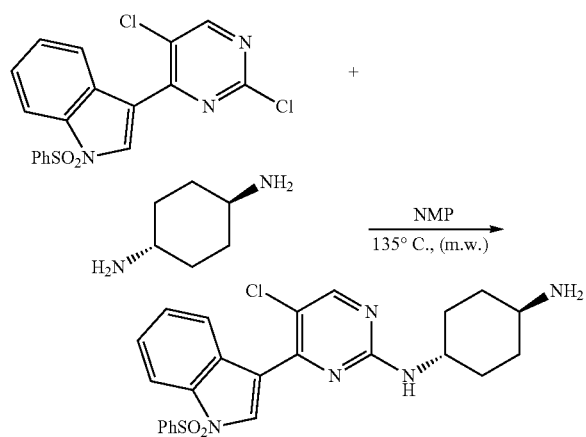

A solution of 3-(2,5-dichloropyrimidin-4-yl)-1-(phenylsulfonyl)-1H-indole (500 mg, 1.24 mmol), trans-1,4-diaminocyclohexane (170 mg, 1.49 mmol), and DIPEA (260 µL, 1.49 mmol) in NMP (15 mL) was heated at 135° C. (mW) for 40 min. The cooled mixture was diluted with EtOAc (30 mL), washed with H$_2$O (60 mL), brine (60 mL), dried over Na$_2$SO$_4$, filtered, and evaporated to dryness. The residue was purified by SiO$_2$ chromatography (DCM/MeOH 5 to 30% gradient) to afford the title compound (298 mg, 0.618 mmol, 50%) as a white solid.

tert-butyl 3-(trans-4-(5-chloro-4-(1-(phenylsulfonyl)-1H-indol-3-yl)pyrimidin-2-ylamino)cyclohexylcarbamoyl)phenylcarbamate

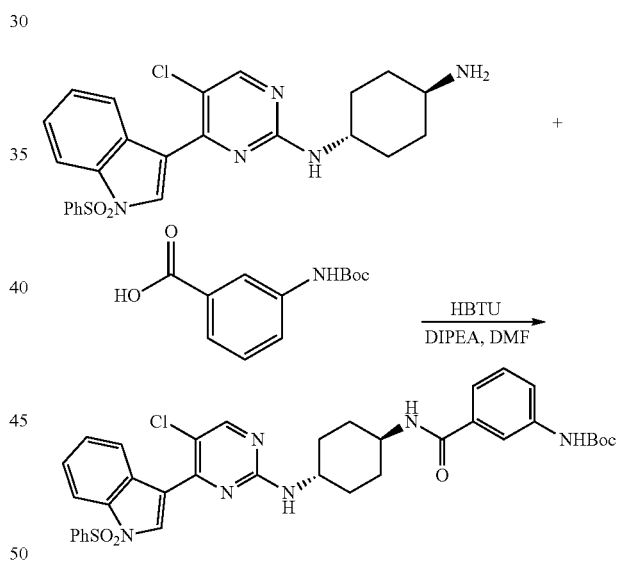

A solution of (trans)-N1-(5-chloro-4-(1-(phenylsulfonyl)-1H-indol-3-yl)pyrimidin-2-yl)cyclohexane-1,4-diamine (125 mg, 0.260 mmol) and 3-(tert-butoxycarbonylamino)benzoic acid (69 mg, 0.290 mmol) in DMF (2.5 mL) was treated with DIPEA (68 µL, 0.390 mmol) and HBTU (148 mg, 0.390 mmol). The resulting mixture was stirred overnight at rt then diluted with EtOAc (20 mL) and saturated NaHCO$_3$ (10 mL). The layers were separated and the aqueous layer was extracted with EtOAc (2×20 mL). The combined organic layers were washed with brine (10 mL), dried over Na$_2$SO$_4$, filtered, and evaporated to dryness to afford the title compound (182 mg, 0.290 mmol, 100%) as a yellow solid which was used in the next step without further purification.

tert-butyl 3-(trans-4-(5-chloro-4-(1H-indol-3-yl)pyrimidin-2-ylamino)cyclohexylcarbamoyl)phenylcarbamate

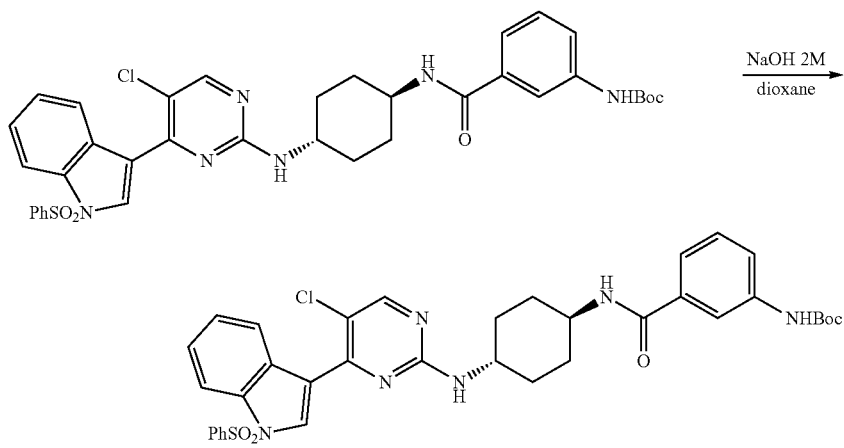

A solution of tert-butyl 3-(trans-4-(5-chloro-4-(1-(phenylsulfonyl)-1H-indol-3-yl)pyrimidin-2-ylamino)cyclohexylcarbamoyl)phenylcarbamate (182 mg, 0.290 mmol) in dioxane (3.0 mL) was treated with a 2M solution of NaOH in H₂O (2.5 mL, 5.00 mmol) and stirred at 70° C. for 1 h. The cooled mixture was evaporated to dryness and the residue was dissolved in MeTHF (20 mL) and H₂O (10 mL). The layers were separated and the aqueous layer was extracted with MeTHF (3×10 mL). The combined organic layers were dried over Na₂SO₄, filtered, and evaporated to dryness to afford the title compound (163 mg, 0.290 mmol, 100%) as a yellow solid which was used in the next step without further purification.

3-amino-N-(trans-4-(5-chloro-4-(1H-indol-3-yl)pyrimidin-2-ylamino)cyclohexyl)benzamide.HCl

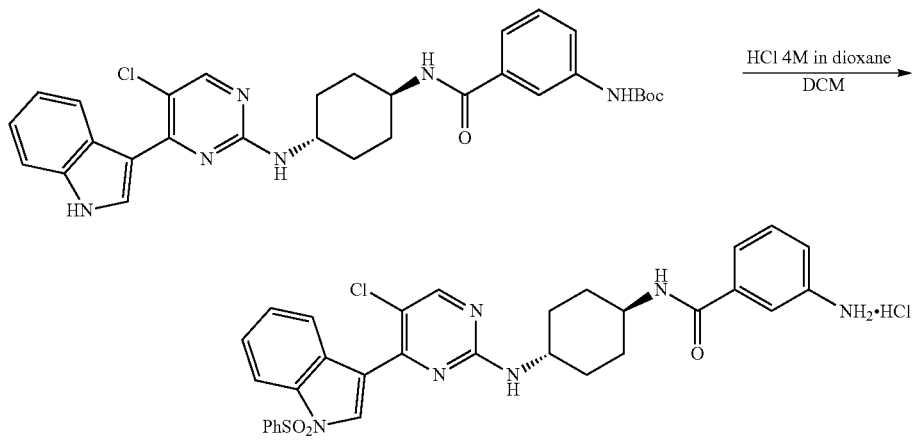

A solution of tert-butyl 3-(trans-4-(5-chloro-4-(1H-indol-3-yl)pyrimidin-2-ylamino)cyclohexylcarbamoyl)phenylcarbamate (163 mg, 0.290 mmol) in DCM (3.0 mL) was treated with a 4M solution of HCl in dioxane (1.10 mL, 4.54 mmol) and stirred 30 min at rt. The resulting mixture was evaporated to dryness to afford the title compound (144 mg, 0.290 mmol, 100%) as a yellow solid.

Example 19. (1S,3R)—N1-((R)-1-(4-aminophenyl)-2,2,2-trifluoroethyl)-N3-(5-chloro-4-(1H-indol-3-yl)pyrimidin-2-yl)cyclohexane-1,3-diamine (Compound 120)

tert-butyl (1R,3S)-3-(hydroxymethyl)cyclohexylcarbamate

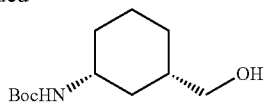

-continued

A cooled (0° C.) solution of (1S,3R)-3-(tert-butoxycarbonylamino)-cyclohexanecarboxylic acid (prepared following Tetrahedron: *Asymmetry* 2010 (21), 864-866) (1.24 g, 5.09 mmol) in THF (34 mL) was treated with a 2M solution of BH₃·Me₂S in THF (3.7 mL, 7.38 mmol) and stirred overnight at rt. The resulting solution was treated with a 1M solution of HCl in H₂O (20 mL) and extracted with EtOAc (3×20 mL). The combined organic layers were dried over MgSO₄, filtered, and evaporated to dryness affording the title compound (1.17 g, 5.09 mmol, 100%) as a colorless oil which was used in the next step without further purification.

(R)-tert-butyl 3-methylenecyclohexylcarbamate

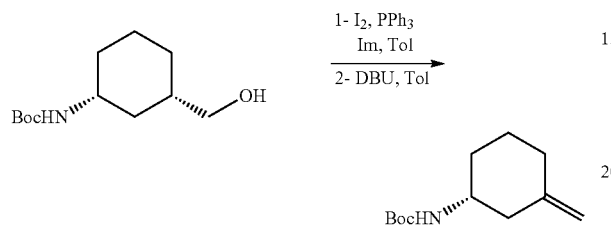

A cooled (0° C.) solution of tert-butyl (1R,3S)-3-(hydroxymethyl)cyclohexylcarbamate (200 mg, 0.87 mmol) in toluene (6 mL) was sequentially treated with imidazole (148 mg, 2.18 mmol), PPh₃ (572 mg, 2.18 mmol) and I₂ (288 mg, 1.13 mmol). The resulting mixture was stirred overnight at rt before being diluted with a saturated solution of NaHCO₃ (10 mL), a 5% solution of Na₂S₂O₃ (10 mL), and DCM (30 mL). The layers were separated and the aqueous layer was extracted with DCM (2×30 mL). The combined organic layers were dried over MgSO₄, filtered, and evaporated to dryness. The residue was taken back up in toluene (10 mL), treated with DBU (261 µL, 1.74 mmol), and heated overnight at 80° C. The cooled mixture was diluted with a saturated solution of NH₄Cl (10 mL) and EtOAc (20 mL). The layers were separated and the aqueous layer was extracted with EtOAc (3×20 mL). The combined organic layers were dried over MgSO₄, filtered, and evaporated to dryness. The residue was purified by SiO₂ chromatography (Hex/EtOAc 5 to 30% gradient) to afford the title compound (72 mg, 0.341 mmol, 39%) as a white solid.

(R)-tert-butyl 3-oxocyclohexylcarbamate

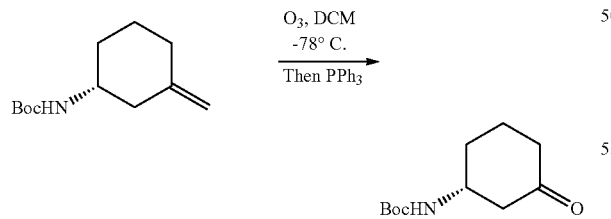

O₃ was bubbled into a cooled (−78° C.) solution of (R)-tert-butyl 3-methylenecyclohexylcarbamate (424 mg, 2.01 mmol) in DCM (40 mL) for 30 min, at which point PPh₃ (917 mg, 6.02 mmol) was added. The resulting mixture was warmed up to rt and evaporated to dryness. The residue was purified by SiO₂ chromatography (Hex/EtOAc 0 to 60% gradient) and afforded the title compound (415 mg, 1.95 mmol, 97%) as a white solid.

tert-butyl (1R,3S)-3-((R)-1-(4-bromophenyl)-2,2,2-trifluoroethylamino)cyclohexylcarbamate

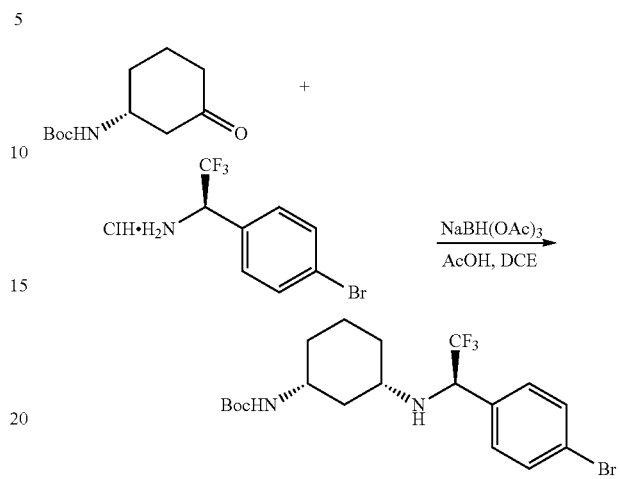

A solution of (R)-1-(4-bromophenyl)-2,2,2-trifluoroethanamine.HCl (prepared following *Org. Lett.* 2005, 7, 2, 355-358) (501 mg, 1.72 mmol) in DCE (16.4 mL) was sequentially treated with DIPEA (314 µL, 1.81 mmol), AcOH (47 µL, 0.82 mmol), (R)-tert-butyl 3-oxocyclohexylcarbamate (350 mg, 1.64 mmol), and NaBH(OAc)₃ (522 mg, 2.46 mmol). The resulting mixture was stirred 16 at rt and then diluted with DCM (20 mL) and a saturated solution of NaHCO₃ (10 mL). The layers were separated and the organic layer was washed with brine (10 mL), dried over MgSO₄, filtered, and evaporated to dryness. The residue was purified by SiO₂ chromatography (Hex/EtOAc 5 to 50% gradient) to afford the title compound (356 mg, 0.789 mmol, 48%) as a white solid. (1S,3R)—N1-((R)-1-(4-bromophenyl)-2,2,2-trifluoroethyl)cyclohexane-1,3-diamine.HCl

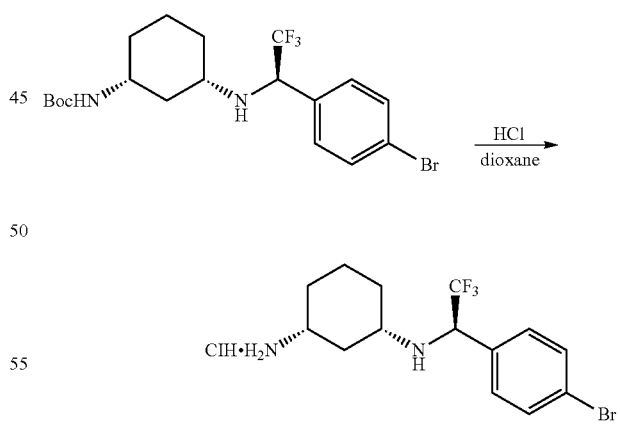

A solution of tert-butyl (1R,3S)-3-((R)-1-(4-bromophenyl)-2,2,2-trifluoroethylamino)cyclohexylcarbamate (144 mg, 0.32 mmol) in DCM (0.65 mL) was treated with a 4M solution of HCl in dioxane (1.60 mL, 6.38 mmol) and stirred 1 h at rt. The resulting mixture was evaporated to dryness to afford the title compound (121 mg, 0.312 mmol, 98%) as a beige solid which was used in the next step without further purification.

(1S,3R)—N1-((R)-1-(4-bromophenyl)-2,2,2-trifluoroethyl)-N3-(5-chloro-4-(1-(phenylsulfonyl)-1H-indol-3-yl)pyrimidin-2-yl)cyclohexane-1,3-diamine

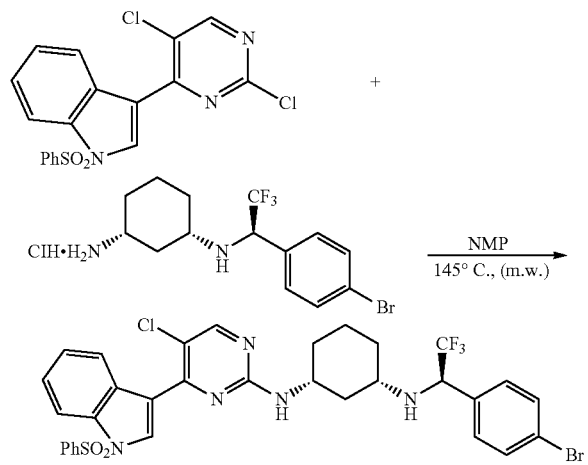

A solution of 3-(2,5-dichloropyrimidin-4-yl)-1-(phenylsulfonyl)-1H-indole (155 mg, 0.380 mmol), (1S,3R)—N1-((R)-1-(4-bromophenyl)-2,2,2-trifluoroethyl)cyclohexane-1,3-diamine.HCl (126 mg, 0.325 mmol) and DIPEA (200 µL, 1.15 mmol) in NMP (2.6 mL) was heated at 145° C. (mW) for 90 min. The cooled mixture was diluted with MeTHF (20 mL), washed with H₂O (10 mL), brine (10 mL), dried over MgSO₄, filtered, and evaporated to dryness. The residue was purified by SiO₂ chromatography (Hex/EtOAc 0 to 100% gradient) to afford the title compound (141 mg, 0.196 mmol, 60%) as a pale yellow foam.

tert-butyl 4-((R)-1-((1 S,3R)-3-(5-chloro-4-(1-(phenylsulfonyl)-1H-indol-3-yl)pyrimidin-2-ylamino) cyclohexylamino)-2,2,2-trifluoroethyl)phenylcarbamate

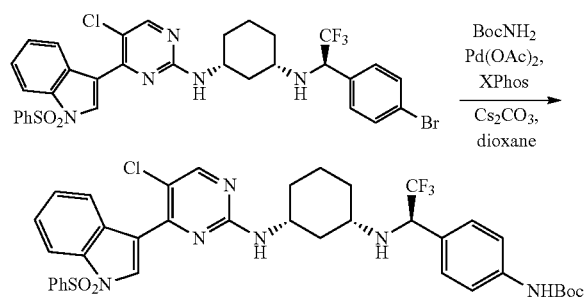

A degassed solution of (1S,3R)—N1-((R)-1-(4-bromophenyl)-2,2,2-trifluoroethyl)-N3-(5-chloro-4-(1-(phenylsulfonyl)-1H-indol-3-yl)pyrimidin-2-yl)cyclohexane-1,3-diamine (141 mg, 0.196 mmol), t-butylcarbamate (28 mg, 0.24 mmol), Pd(OAc)₂ (1.3 mg, 0.01 mmol), Xphos (8.4 mg, 0.02 mmol) and Cs₂CO₃ (90 mg, 0.27 mmol) in dioxane (2.0 mL) was heated at 90° C. for 12 h. The cooled mixture was filtered over celite (EtOAc) and the filtrate was evaporated to dryness. The residue was purified by SiO₂ chromatography (Hex/EtOAc 0 to 100% gradient) to afford the title compound (191 mg as a mixture with unknown impurity) as a pale yellow foam.

(1 S,3R)—N1-((R)-1-(4-aminophenyl)-2,2,2-trifluoroethyl)-N3-(5-chloro-4-(1H-indol-3-yl)pyrimidin-2-yl)cyclohexane-1,3-diamine

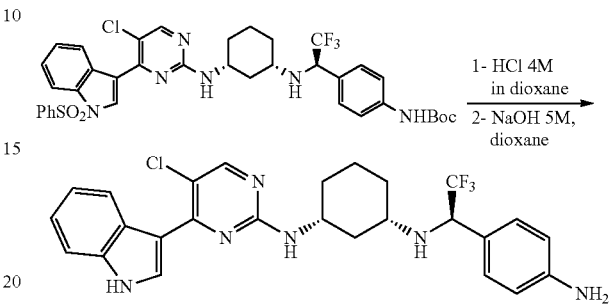

A solution of tert-butyl 4-((R)-14(1S,3R)-3-(5-chloro-4-(1-(phenylsulfonyl)-1H-indol-3-yl)pyrimidin-2-ylamino) cyclohexylamino)-2,2,2-trifluoroethyl)phenylcarbamate (191 mg as a mixture with unknown impurity) in DCM (0.4 mL) was treated with a 4M solution of HCl in dioxane (730 µL, 2.94 mmol) and stirred 30 min at rt. The resulting mixture was evaporated to dryness, suspended in dioxane (1.3 mL) and treated with a 5M solution of NaOH in H₂O (590 µl, 2.94 mmol). The resulting mixture was stirred 5 h at rt and diluted with MeTHF (20 mL) and H₂O (10 mL). The layers were separated and the aqueous layer was extracted with MeTHF (2×10 mL). The combined organic layers were dried over MgSO₄, filtered, and evaporated to dryness. The residue was purified by SiO₂ chromatography (DCM/THF 0 to 50% gradient) to afford the title compound (59 mg, 0.115 mmol, 58% over 2 steps) as a pale yellow solid.

Example 20. 4-amino-N-((1S,3R)-3-(5-fluoro-4-(1H-indol-3-yl)pyrimidin-2-ylamino)cyclohexyl) benzamide.HCl (Compound 121)

3-(2-chloro-5-fluoropyrimidin-4-yl)-1-(phenylsulfonyl)-1H-indole

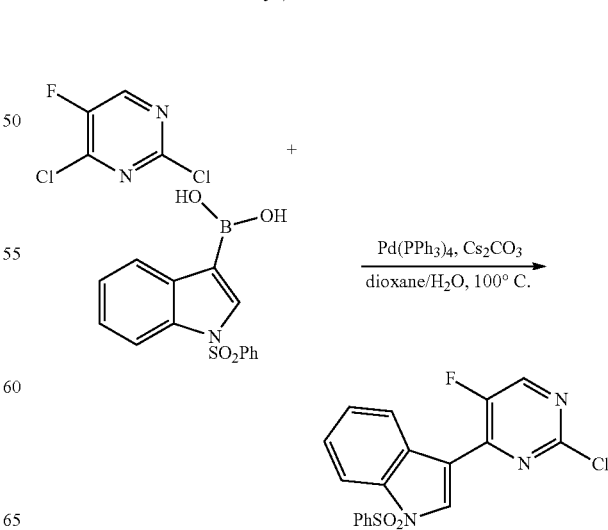

A degassed solution of 2,4-dichloro-5-fluoropyrimidine (500 mg, 2.99 mmol), 1-(phenylsulfonyl)-1H-indol-3-ylboronic acid (947 mg g, 3.14 mmol), Cs₂CO₃ (1.95 g, 5.99 mmol), and Pd(PPh₃)₄ (346 mg, 0.30 mmol) in 2/1 dioxane/H₂O (30 ml) was heated overnight at 100° C. The cooled mixture was diluted with EtOAc (50 mL) and saturated NaHCO₃ (20 ml). The layers were separated and the aqueous layer was extracted with EtOAc (3×20 mL). The combined organic layers were washed with brine (20 mL), dried over MgSO₄ and evaporated to dryness. The residue was purified by SiO₂ chromatography (DCM) to afford the title compound (599 mg, 1.55 mmol, 52%) as a pale orange oil.

tert-butyl-(1S,3R)-3-(5-fluoro-4-(1-(phenylsulfonyl)-1H-indol-3-yl)pyrimidin-2-ylamino)cyclohexylcarbamate

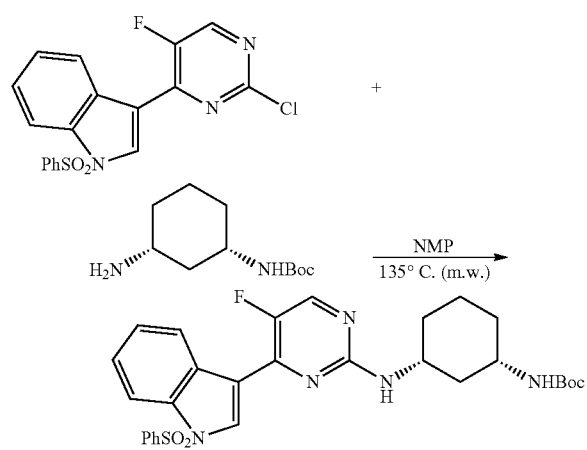

A solution of 3-(2-chloro-5-fluoropyrimidin-4-yl)-1-(phenylsulfonyl)-1H-indole (250 mg, 0.64 mmol), tert-butyl (1S,3R)-3-aminocyclohexylcarbamate prepared as in example 3 (138 mg, 0.64 mmol) and DIPEA (237 µL, 1.93 mmol) in NMP (4.3 mL) was heated at 140° C. (microwave) for 60 min. The cooled mixture was diluted with MeTHF (30 mL), washed with H₂O (10 mL), brine (10 mL), dried over MgSO₄, filtered, and evaporated to dryness. The residue was purified by SiO₂ chromatography (DCM/EtOAc 0 to 30% gradient) to afford the title compound (76 mg, 0.134 mmol, 21%) as a pale yellow solid.

(1R,3S)—N1-(5-fluoro-4-(1-(phenylsulfonyl)-1H-indol-3-yl)pyrimidin-2-yl)cyclohexane-1,3-diamine.HCl

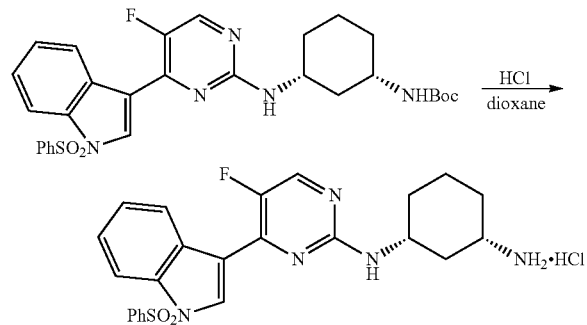

A solution of tert-butyl (1S,3R)-3-(5-fluoro-4-(1-(phenylsulfonyl)-1H-indol-3-yl)pyrimidin-2-ylamino)cyclohexylcarbamate (76 mg, 0.134 mmol) in dioxane (0.3 mL) was treated with a 4M solution of HCl in dioxane (340 µL, 1.34 mmol) and stirred 1 h at rt. The resulting mixture was evaporated to dryness to afford the title compound (64 mg, 0.127 mmol, 95%) as a white solid which was used in the next step without further purification.

tert-butyl 4-((1 S,3R)-3-(5-fluoro-4-(1-(phenylsulfonyl)-1H-indol-3-yl)pyrimidin-2-ylamino)cyclohexylcarbamoyl)phenylcarbamate

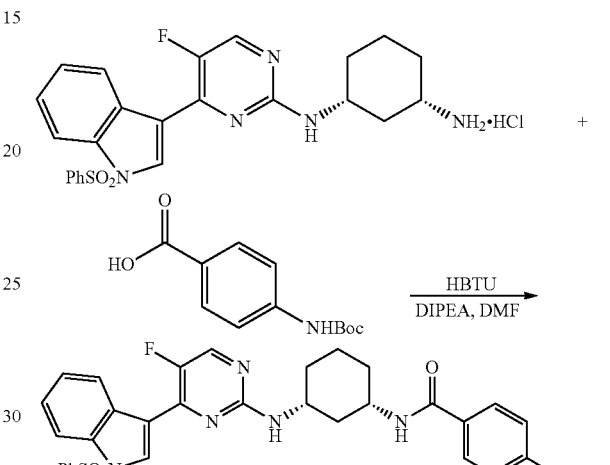

A solution of (1R,3S)—N1-(5-fluoro-4-(1-(phenylsulfonyl)-1H-indol-3-yl)pyrimidin-2-yl)cyclohexane-1,3-diamine.HCl (64 mg, 0.127 mmol) and 4-(tert-butoxycarbonylamino)benzoic acid (27 mg, 0.130 mmol) in DMF (0.85 mL) was treated with DIPEA (66 µL, 0.51 mmol) and HBTU (97 mg, 0.256 mmol). The resulting mixture was stirred overnight at rt, diluted with EtOAc (20 mL) and saturated NaHCO₃ (10 mL). The layers were separated and the aqueous layer was extracted with EtOAc (2×20 mL). The combined organic layers were washed with brine (10 mL), dried over Na₂SO₄, filtered and evaporated to dryness. The residue was purified by SiO₂ chromatography (DCM/EtOAc 0 to 100% gradient) to afford the title compound (87 mg, 0.127 mmol, 100%) as a pale yellow solid.

tert-butyl 44(1 S,3R)-3-(5-fluoro-4-(1H-indol-3-yl)pyrimidin-2-ylamino)cyclohexylcarbamoyl)phenylcarbamate

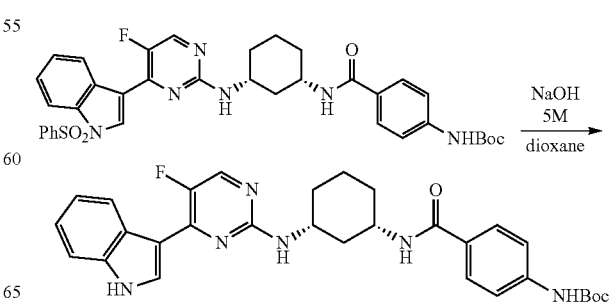

A solution of tert-butyl 44(1S,3R)-3-(5-fluoro-4-(1-(phenylsulfonyl)-1H-indol-3-yl)pyrimidin-2-ylamino)cyclohexylcarbamoyl)phenylcarbamate (87 mg, 0.127 mmol) in dioxane (0.85 ml) was treated with a 5M solution of NaOH in H$_2$O (380 μL, 1.91 mmol) and heated at 65° C. for 5 h. The cooled mixture was evaporated to dryness and the residue was purified by SiO$_2$ chromatography (DCM/THF 0 to 50% gradient) to afford the title compound (59 mg, 0.108 mmol, 85%) as a pale yellow solid.

4-amino-N-((1 S,3R)-3-(5-fluoro-4-(1H-indol-3-yl)pyrimidin-2-ylamino)cyclohexyl)benzamide.HCl

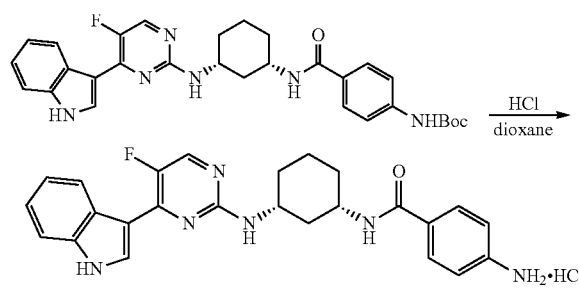

A solution of tert-butyl 4-((1S,3R)-3-(5-fluoro-4-(1H-indol-3-yl)pyrimidin-2-ylamino)cyclohexylcarbamoyl)phenylcarbamate (59 mg, 0.108 mmol) in dioxane (720 μL) was treated with a 4M solution of HCl in dioxane (410 μL, 1.62 mmol) and stirred overnight at rt. The resulting mixture was evaporated to dryness to afford the title compound (52 mg, 0.108 mmol, 100%) as a white solid.

Example 21. (1S,3R)—N1-(4-aminobenzyl)-N3-(5-chloro-4-(1H-indol-3-yl)pyrimidin-2-yl)-N1-methyl-cyclohexane-1,3-diamine.HCl (Compound 122)

tert-butyl 4-(((1 S, 3R)-3-(5-chloro-4-(1-(phenylsulfonyl)-1H-indol-3-yl)pyrimidin-2-ylamino)cyclohexylamino)methyl)phenylcarbamate

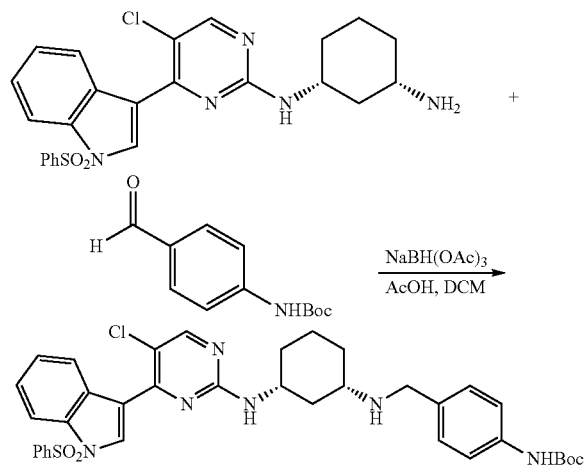

A solution of (1R,3S)—N1-(5-chloro-4-(1-(phenylsulfonyl)-1H-indol-3-yl)pyrimidin-2-yl)cyclohexane-1,3-diamine prepared as in example 3 (180 mg, 0.373 mmol), tert-butyl 4-formylphenylcarbamate (124 mg, 0.822 mmol) and AcOH (21 μL, 0.221 mmol) in DCM (3.7 mL) was treated with NaBH(OAc)$_3$ (198 mg, 0.934 mmol) and stirred overnight at rt. The resulting mixture was diluted with DCM (20 mL) and saturated NaHCO$_3$ (10 mL). The layers were separated and the aqueous layer was extracted with DCM (2×10 mL). The combined organic layers were dried over MgSO$_4$, filtered, and evaporated to dryness. The residue was purified by SiO$_2$ chromatography (DCM/MeOH 0 to 12% gradient) to afford the title compound (178 mg, 0.259 mmol, 69%) as a white foam.

tert-butyl 4-((((1 S,3R)-3-(5-chloro-4-(1-(phenylsulfonyl)-1H-indol-3-yl)pyrimidin-2-ylamino)cyclohexyl)(methyl)amino)methyl)phenylcarbamate

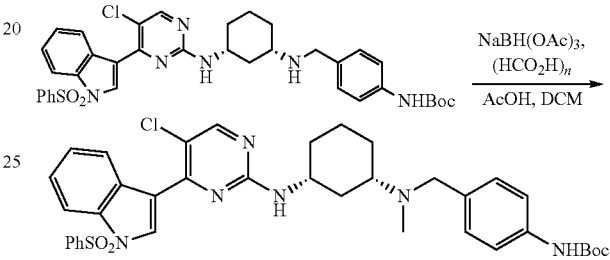

A solution of tert-butyl 4-(((1S,3R)-3-(5-chloro-4-(1-(phenylsulfonyl)-1H-indol-3-yl)pyrimidin-2-ylamino)cyclohexylamino)methyl)phenylcarbamate (178 mg, 0.259 mmol), paraformaldehyde (14 mg, 0.466 mmol) and AcOH (15 μL, 0.259 mmol) in DCM (4.3 mL) was treated with NaBH(OAc)$_3$ (132 mg, 0.622 mmol) and stirred 40 h at rt. The resulting mixture was diluted with DCM (20 mL) and saturated NaHCO$_3$ (10 mL). The layers were separated and the aqueous layer was extracted with DCM (2×10 mL). The combined organic layers were dried over MgSO$_4$, filtered, and evaporated to dryness. The residue was purified by SiO$_2$ chromatography (DCM/MeOH 0 to 12% gradient) to afford the title compound (96 mg, 0.137 mmol, 53%) as a white foam.

tert-butyl 4-((((1 S, 3R)-3-(5-chloro-4-(1H-indol-3-yl)pyrimidin-2-ylamino)cyclohexyl)(methyl)amino)methyl)phenylcarbamate

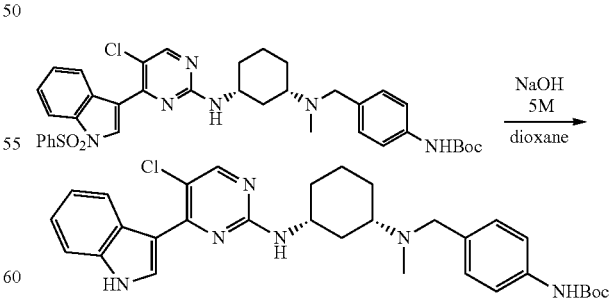

A solution of tert-butyl 4-((((1S,3R)-3-(5-chloro-4-(1-(phenylsulfonyl)-1H-indol-3-yl)pyrimidin-2-ylamino)cyclohexyl)(methyl)amino)methyl)phenylcarbamate (96 mg, 0.137 mmol) in dioxane (2.7 mL) was treated with a 5M solution of NaOH in H$_2$O (0.55 mL, 2.74 mmol) and heated at 65° C. for 2 h. The cooled mixture was diluted with H₂O (5 mL) and MeTHF (10 mL). The layers were separated and the aqueous layer was extracted with MeTHF (3×10 mL). The combined organic layers were dried over MgSO4, filtered, and evaporated to dryness. The residue was purified by SiO₂ chromatography (DCM/MeOH 0 to 12% gradient) to afford the title compound (57 mg, 0.102 mmol, 74%) as a pale yellow foam.

(1S,3R)—N1-(4-aminobenzyl)-N3-(5-chloro-4-(1H-indol-3-yl)pyrimidin-2-yl)-N1-methylcyclohexane-1,3-diamine.HCl

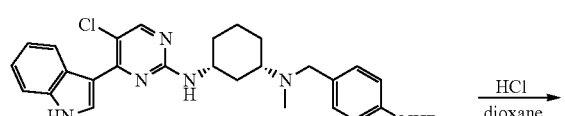

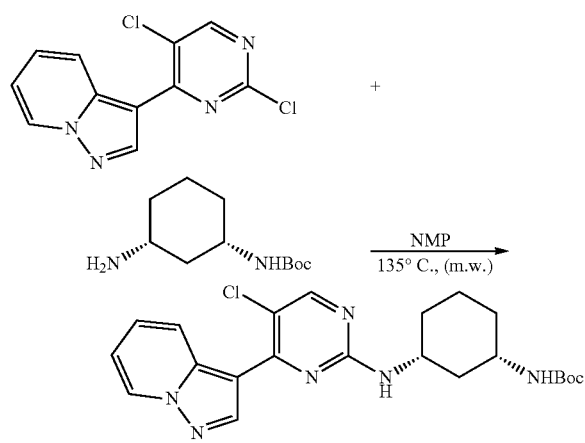

A solution of tert-butyl 4-(((((1S,3R)-3-(5-chloro-4-(1H-indol-3-yl)pyrimidin-2-ylamino)cyclohexyl)(methyl) amino)methyl)phenylcarbamate (57 mg, 0.101 mmol) in DCM (2.0 mL) was treated with a 4M solution of HCl in dioxane (1.0 mL, 4.06 mmol) and stirred 18 h at rt. The resulting mixture was evaporated to dryness to afford the title compound (50 mg, 0.101 mmol, 100%) as a bright yellow solid.

Example 22. 4-amino-N-((1S,3R)-3-(5-chloro-4-(pyrazolo[1,5-a]pyridin-3-yl)pyrimidin-2-ylamino) cyclohexyl)benzamide.HCl (Compound 123)

tert-butyl (1S,3R)-3-(5-chloro-4-(pyrazolo[1,5-a]pyridin-3-yl)pyrimidin-2-ylamino)cyclohexylcarbamate (200 mg, 0.933 mmol) and DIPEA (171 μL, 0.980 mmol) in NMP (7.8 mL) was heated at 135° C. (mW) for 30 min. The cooled mixture was diluted with EtOAc (30 mL), washed with H₂O (10 mL), brine (10 mL), dried over MgSO₄, filtered, and evaporated to dryness. The residue was purified by SiO₂ chromatography (DCM/MeOH 0 to 12% gradient) to afford the title compound (280 mg, 0.632 mmol, 68%) as an orange foam.

(1R,3S)—N1-(5-chloro-4-(pyrazolo[1,5-a]pyridin-3-yl)pyrimidin-2-yl)cyclohexane-1,3-diamine.HCl

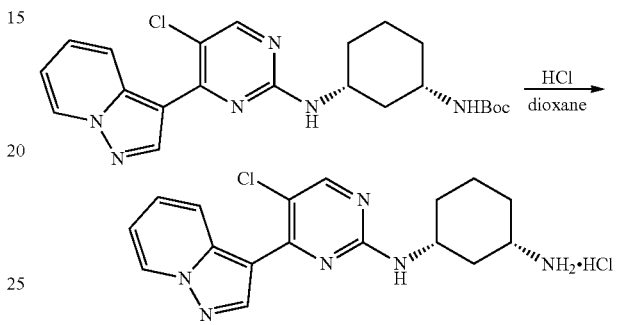

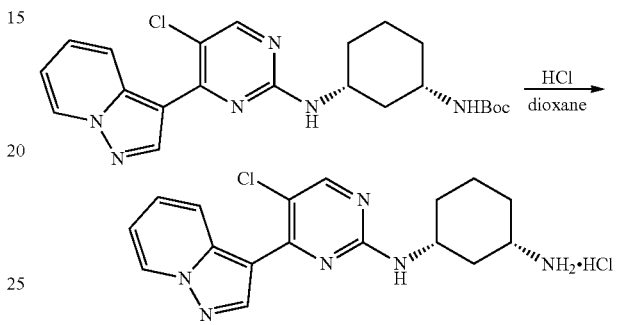

A solution of tert-butyl (1S,3R)-3-(5-chloro-4-(pyrazolo [1,5-a]pyridin-3-yl)pyrimidin-2-ylamino)cyclohexylcarbamate (280 mg, 0.632 mmol) in DCM (4.1 mL) was treated with a 4M solution of HCl in dioxane (2.04 mL, 8.165 mmol) and stirred 5 h at rt. The mixture was diluted with EtOAc (5 mL) and H₂O (5 mL) and the resulting precipitate was filtered and washed with EtOAc, affording the title compound (142 mg, 0.415 mmol, 66%) as a white solid which was used in the next step without further purification.

tert-butyl 4-((1S,3R)-3-(5-chloro-4-(pyrazolo[1,5-a] pyridin-3-yl)pyrimidin-2-ylamino)cyclohexylcarbamoyl)phenylcarbamate

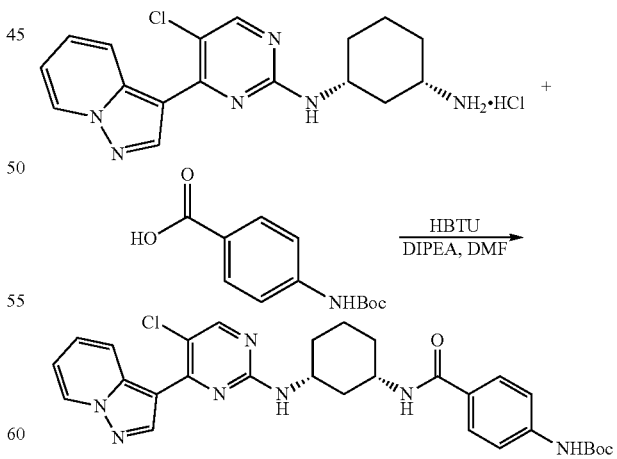

A solution of 3-(2,5-dichloropyrimidin-4-yl)pyrazolo[1,5-a]pyridine (prepared following *J. Med. Chem*, 2013, 56(17), 7025-7048) (223 mg, 0.84 mmol), tert-butyl (1S,3R)-3-aminocyclohexylcarbamate prepared as in example 3

A solution of (1R,3S)—N1-(5-chloro-4-(pyrazolo[1,5-a] pyridin-3-yl)pyrimidin-2-yl)cyclohexane-1,3-diamine.HCl (140 mg, 0.408 mmol) and 4-(tert-butoxycarbonylamino) benzoic acid (116 mg, 0.49 mmol) in DMF (4.1 mL) was treated with DIPEA (285 μL, 1.63 mmol) and HBTU (232 mg, 0.613 mmol). The resulting mixture was stirred overnight at rt, diluted with EtOAc (30 mL) and saturated NaHCO₃ (10 mL). The layers were separated and the organic layer was washed with brine (10 mL), dried over MgSO₄, filtered, and evaporated to dryness. The residue was purified by SiO₂ chromatography (Hex/EtOAc 0 to 100% gradient) to afford the title compound (229 mg, 0.408 mmol, 100%) as an orange oil.

4-amino-N-((1S,3R)-3-(5-chloro-4-(pyrazolo[1,5-a]pyridin-3-yl)pyrimidin-2-ylamino)cyclohexyl)benzamide.HCl

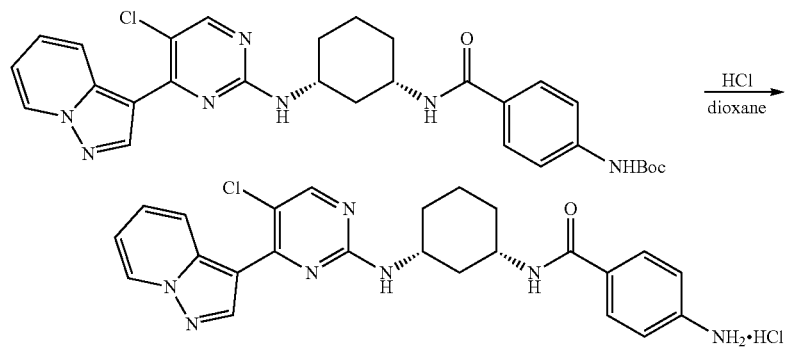

A solution of tert-butyl 4-((1S,3R)-3-(5-chloro-4-(pyrazolo[1,5-a]pyridin-3-yl)pyrimidin-2-ylamino)cyclohexylcarbamoyl)phenylcarbamate (229 mg, 0.408 mmol) in DCM (1.0 mL) was treated with a 4M solution of HCl in dioxane (2.0 mL, 8.0 mmol) and stirred 1 h at rt. The resulting mixture was evaporated to dryness and the residue was triturated in EtOAc. The solid was filtered and washed with EtOAc to afford the title compound (28 mg, 0.061 mmol, 15%) as a beige solid.

Example 23. Synthesis of 5-amino-N-((1S,3R)-3-(5-chloro-4-(1-methyl-1H-indol-3-yl)pyrimidin-2-ylamino)cyclohexyl)picolinamide (Compound 125)

3-(2,5-dichloropyrimidin-4-yl)-1H-indole

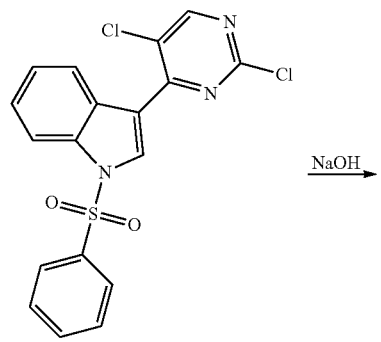

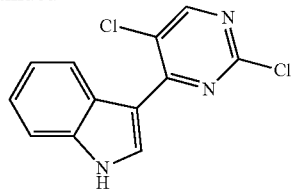

To a suspension of 3-(2,5-dichloropyrimidin-4-yl)-1-(phenylsulfonyl)-1H-indole (1.50 g, 3.71 mmol) in water/1,4-dioxane (62 mL/19 mL) was added an aqueous solution of NaOH (11 mL, 5M, 55 mmol). The suspension is stirred at 75° C. for 3 h. The reaction was then cooled to room temperature, concentrated under reduced pressure and extracted into DCM (100 mL). The DCM layer was dried over MgSO₄, filtered, and concentrated to afford the title compound as a light yellow oil (0.734 g, 2.78 mmol, 75%) which was used without any further purification.

3-(2,5-dichloropyrimidin-4-yl)-1-methyl-1H-indole

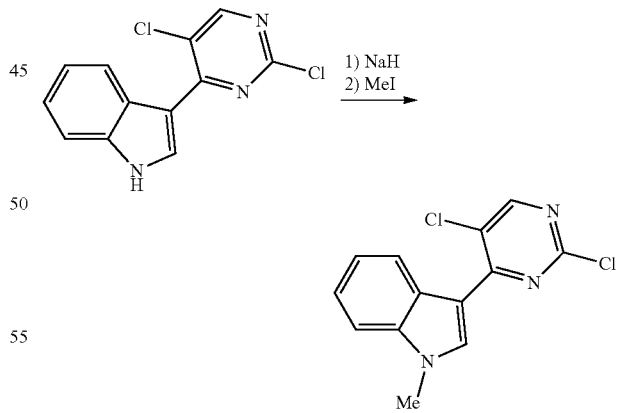

To a suspension of 3-(2,5-dichloropyrimidin-4-yl)-1H-indole (970 mg, 3.67 mmol) in DMF (18.4 mL) at 0° C., sodium hydride in mineral oil (0.220 g, 5.51 mmol, 60% w/w) was added. The reaction was warmed to room temperature and stirred for 0.5 h. The reaction was cooled to 0° C. and methyl iodide (0.834 g, 5.88 mmol) was added. The reaction was warmed to room temperature and stirred for 12 h. The reaction was poured into ice-water (200 mL) and was extracted with EtOAc (2×50 mL). The organic layer was washed with brine and directly concentrated to dryness. The crude product was then stirred in MTBE (100 mL) for 1 h, and a white solid is filtered off to afford the title compound as a white-yellow powder (0.500 g, 1.798 mmol, 49%).

(1S,3R)-3-(Benzyloxycarbonylamino)cyclohexylamino 2,2-dimethylpropionate

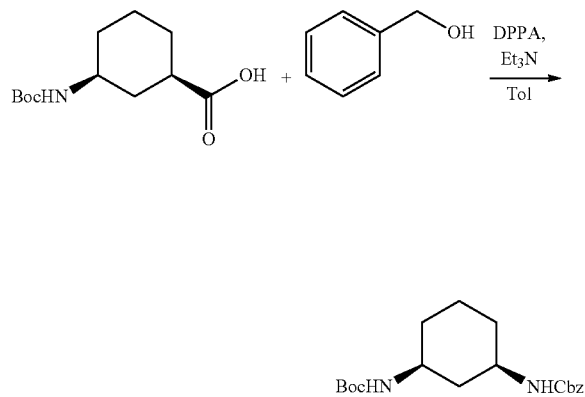

To a solution of (1R,3S)-3-(tert-butoxycarbonylamino)cyclohexanecarboxylic acid (prepared following Tetrahedron: Asymmetry 2010 (21), 864-866) (8.77 g, 36.1 mmol) was added Et₃N (5.53 mL, 39.7 mmol) and DPPA (7.7 mL, 36.1 mmol). The resulting solution was stirred 2 h at 110° C. then cooled to 80° C. Benzyl alcohol (4.66 mL, 45.1 mmol) and triethylamine (5.53 mL, 39.7 mmol) were added and the mixture was stirred for 20 h at 80° C. The cooled solution was diluted with EtOAc (100 mL) and water (50 mL). The layers were separated and the aqueous layer was extracted with EtOAc (2×50 mL). The combined organics were dried (MgSO₄), filtered, and evaporated to dryness. The residue was purified by SiO₂ chromatography (Hex/EtOAc 1 to 100% gradient), to afford the title compound (9.89 g, 28.4 mmol, 79%) as a white solid.

tert-butyl (1 S,3R)-3-aminocyclohexylcarbamate

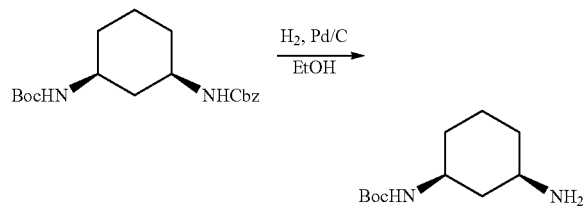

To a degassed solution of (1S,3R)-3-(benzyloxycarbonylamino)cyclohexylamino 2,2-dimethylpropionate (10 g, 28.4 mmol) in EtOH (473 mL) was added 10% w/w Pd/C (450 mg). The reaction mixture was stirred 5 h under H₂ (1 atm). The reaction mixture was filtered through a pad of celite (EtOH), then the filtrate was evaporated to dryness to afford the title compound (6.08 g, 28.4 mmol, 100%) as a white solid.

tert-butyl (1 S, 3R)-3-(5-chloro-4-(1-methyl-1H-indol-3-yl)pyrimidin-2-ylamino)cyclohexylcarbamate

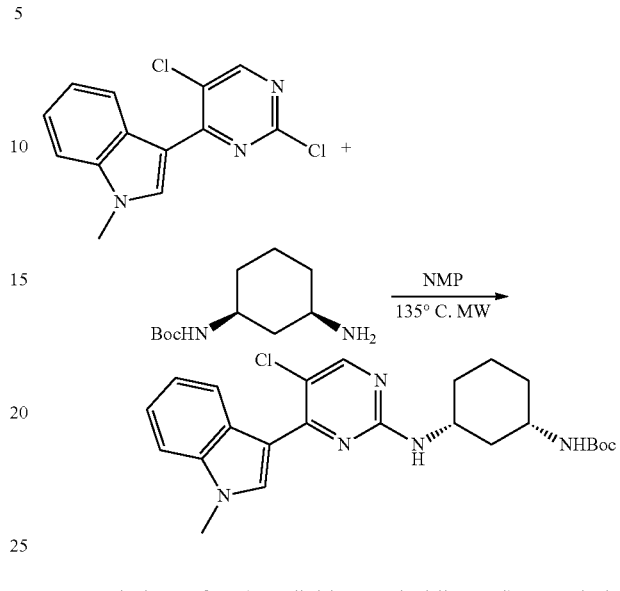

A solution of 3-(2,5-dichloropyrimidin-4-yl)-1-methyl-1H-indole (2.91 g, 7.20 mmol), tert-butyl (1S,3R)-3-aminocyclohexylcarbamate (1.24 g, 5.76 mmol) and diisopropylethylamine (1.05 mL, 6.05 mmol) in NMP (14.5 mL) was heated 1.5 h at 135° C. (mW). The mixture was diluted with EtOAc (200 mL), washed with water (50 mL), brine (50 mL), dried (MgSO₄), then filtered and evaporated to dryness. The residue was purified by SiO₂ chromatography (DCM/EtOAc 0 to 30% gradient) to afford the title compound (1.88 g, 3.23 mmol, 56%) as a light yellow foam.

(1R,3S)—N1-(5-chloro-4-(1-methyl-1H-indol-3-yl)pyrimidin-2-yl)cyclohexane-1,3-diamine.HCl

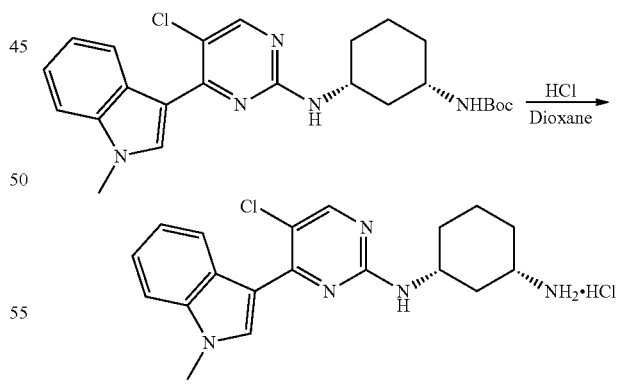

To a solution of tert-butyl (1S,3R)-3-(5-chloro-4-(1-methyl-1H-indol-3-yl)pyrimidin-2-ylamino)cyclohexylcarbamate (1.88 g, 3.23 mmol) in DCM (16.1 mL) was added a solution of 4 N HCl in dioxane (12.11 mL, 48.44 mmol). The resulting mixture was stirred 1.5 h at rt before being evaporated to dryness to afford the title compound (1.72 g, 3.10 mmol, 96%) as a light yellow solid which was used in the next step without further purification.

5-amino-N-((1S,3R)-3-(5-chloro-4-(1-methyl-1H-indol-3-yl)pyrimidin-2-ylamino)cyclohexyl)picolinamide

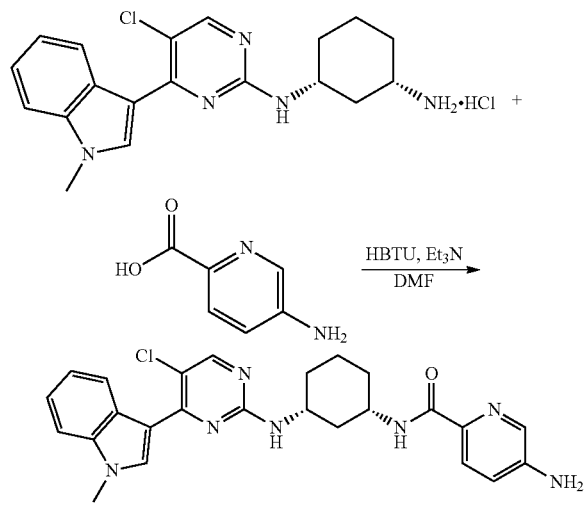

To a solution of (1R,3S)—N1-(5-chloro-4-(1-methyl-1H-indol-3-yl)pyrimidin-2-yl)cyclohexane-1,3-diamine.HCl (300 mg, 0.579 mmol) in DMF (4 mL) was added Et₃N (322 µL, 2.315 mmol), 5-amino-2-pyridinecarboxylic acid (96 mg, 0.694 mmol), and HBTU (329 mg, 0.868 mmol). The mixture was stirred overnight at rt and then diluted with EtOAc (20 mL). The mixture was then washed twice with a saturated solution of NaHCO₃ (10 mL) followed by brine (5 mL), then dried (MgSO₄), filtered, and evaporated to dryness. The residue was triturated with MTBE and filtered, and the filtrate was evaporated to dryness which afforded the title compound (282 mg, 0.468 mmol, 81%) as a yellow solid.

Example 24. Synthesis of N-((1S,3R)-3-((5-chloro-4-(1H-indol-3-yl)pyrimidin-2-yl)amino)cyclohexyl)-4-(4-(dimethylamino)butanamido)benzamide (Compound 105)

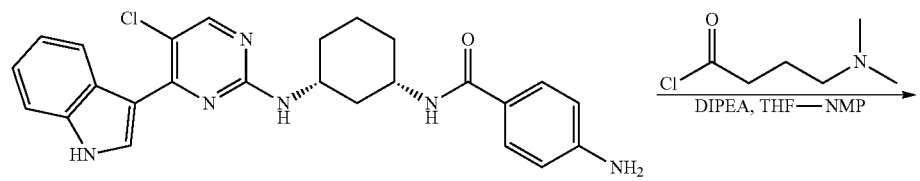

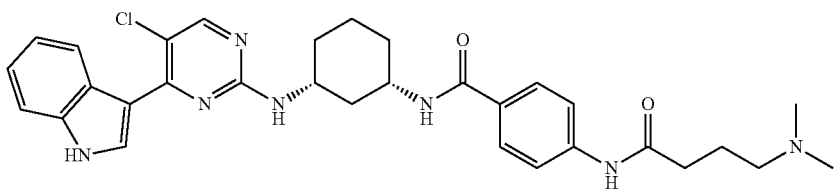

A cooled (−78° C.) solution of 4-amino-N-((1S,3R)-3-(5-chloro-4-(1H-indol-3-yl)pyrimidin-2-ylamino)cyclohexyl)benzamide (Compound 102; 300 mg, 0.651 mmol), and DIPEA (340 µL, 1.95 mmol) in THF/NMP (4.34 mL/0.65 mL) was treated with a 40.84 mg/mL solution of 4-(dimethylamino)butanoyl chloride in DCM (4.96 mL, 0.651 mmol). The resulting mixture was stirred 2 h. The resulting mixture was then evaporated to dryness, and the residue was purified by reverse phase chromatography (C₁₈, H₂O/ACN+ 0.1% HCO₂H, 5 to 60% gradient) to afford the title compound (205 mg, 0.357 mmol, 55%) as a light yellow solid after lyophilisation.

Example 25. Synthesis of N1-(4-(((1S,3R)-34(5-chloro-4-(1H-indol-3-yl)pyrimidin-2-yl)amino)cyclohexyl)carbamoyl)phenyl)oxalamide (Compound 113)

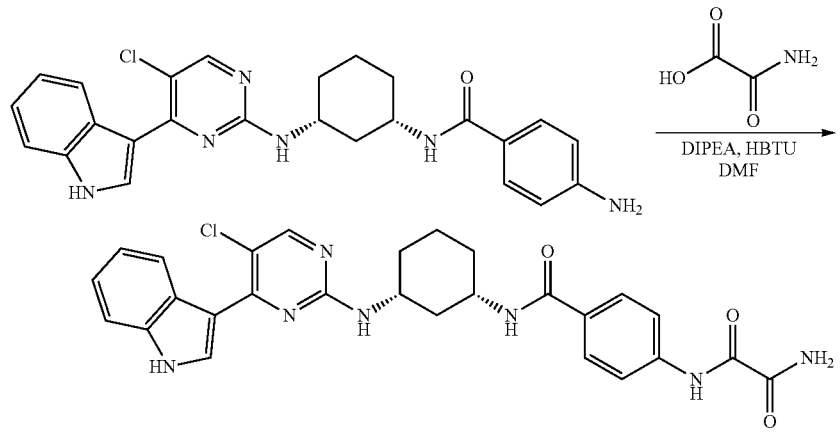

4-amino-N-((1S,3R)-3-(5-chloro-4-(1H-indol-3-yl)pyrimidin-2-ylamino)cyclohexyl)benzamide (Compound 102; 50 mg, 0.11 mmol), oxamic acid (10 mg, 0.11 mmol), HBTU (62 mg, 0.16 mmol) and diisopropylethylamine (38 µL, 0.22 mmol) were dissolved with DMF (1.4 mL) and stirred at room temperature overnight. The resulting mixture was then directly purified by reverse phase chromatography (C$_{18}$, H$_2$O/ACN+0.1% HCO$_2$H, 0 to 60% gradient) to afford the title compound (6.0 mg, 0.011 mmol, 10%) as a light yellow solid after lyophilisation.

Example 26. Synthesis of 4-amino-N-((1S,3R)-34 (5-chloro-4-(1H-indazol-3-yl)pyrimidin-2-yl)amino) cyclohexyl)benzamide (Compound 124)

3-iodo-1H-indazole

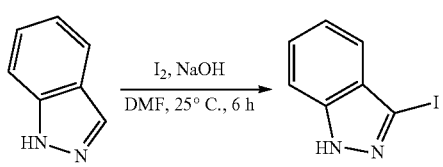 [SMILES: c1ccc2[nH]ncc2c1 ; Ic1n[nH]c2ccccc12]

To a mixture of 1H-indazole (5 g, 42.32 mmol) and NaOH (3.4 g, 84.6 mmol) in DMF (50 mL) was added I$_2$ (16.1 g, 63.4 mmol) in one portion at 25° C. and the mixture was stirred for 6 h. The mixture was concentrated, diluted with water (150 mL) extracted with EA (100 mL*3), and the combined organic phase was washed with saturated brine (200 mL*2), dried with anhydrous Na$_2$SO$_4$ and concentrated in vacuum. The residue was purified by silica gel chromatography to afford the title compound (8 g, 77.5%) as white solid.

Tert-butyl 3-iodo-1H-indazole-1-carboxylate

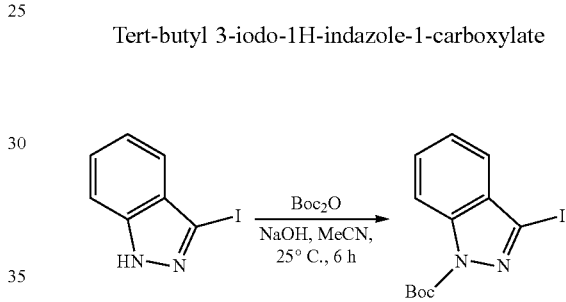

To a mixture of 3-iodo-1H-indazole (8 g, 32.7 mmol) and Boc$_2$O (8.6 g, 39.2 mmol) in MeCN (100 mL) was added NaOH (2.0 g, 49.1 mmol) at 25° C. and the mixture was stirred for 12 h. The mixture was poured into water (150 mL), extracted with EA (50 mL*2), and the combined organic phase was washed with saturated brine (200 mL*2), dried with anhydrous Na$_2$SO$_4$ and concentrated in vacuum. The residue was purified by silica gel chromatography to afford the title compound (11.2 g, 97.5%) as white solid.

Tert-butyl 3-(trimethylstannyl)-1H-indazole-1-carboxylate

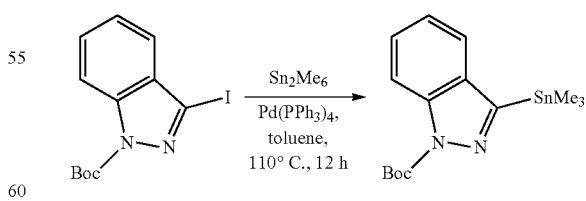

A mixture of tert-butyl 3-iodoindazole-1-carboxylate (4.0 g, 11.6 mmol), Sn$_2$Me$_6$ (5.7 g, 17.4 mmol) and Pd(PPh$_3$)$_4$ (1.3 g, 1.2 mmol) in toluene (20 mL) was heated to 110° C. and stirred for 12 h. The mixture was concentrated in vacuum to give title compound (4.43 g, crude), which was used directly in next step.

103

Tert-butyl 3-(2,5-dichloropyrimidin-4-yl)-1H-indazole-1-carboxylate

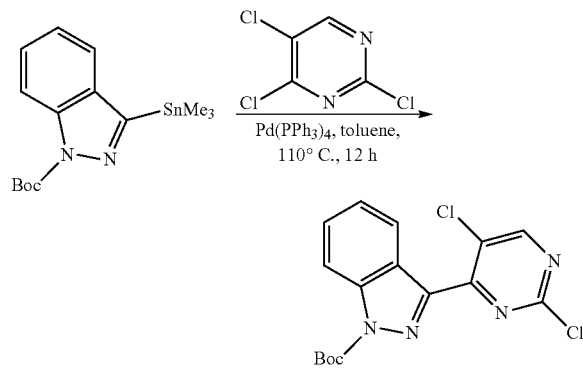

A mixture of tert-butyl 3-trimethylstannylindazole-1-carboxylate (5.0 g, 13.1 mmol), 2,4,5-trichloropyrimidine (2.4 g, 13.1 mmol) and Pd(PPh₃)₄ (1.5 g, 1.3 mmol) in toluene (100 mL) was heated to 110° C. and stirred for 12 h. The mixture was concentrated in vacuum, and the residue was purified by silica gel chromatography to afford the title compound (1.5 g, 31.3% for two steps).

Benzyl((1S,3R)-3-((5-chloro-4-(1H-indazol-3-yl)pyrimidin-2-yl)amino)cyclohexyl)carbamate

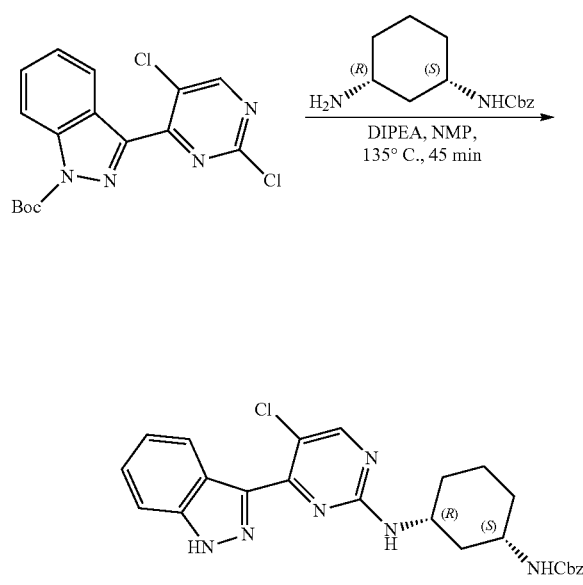

To a mixture of tert-butyl 3-(2,5-dichloropyrimidin-4-yl)indazole-1-carboxylate (1 g, 2.74 mmol), benzyl N-[(1S,3R)-3-aminocyclohexyl]carbamate (0.816 g, 3.3 mmol) and DIPEA (2.1 g, 16.2 mmol) in NMP (20 mL) was stirred at 135° C. for 45 min by microwave. The mixture was poured into water (20 mL), extracted with ethyl acetate (20 mL*2), and the combined organic phase was washed with saturated brine (20 mL*3), dried with anhydrous Na₂SO₄ and concentrated in vacuum. The residue was purified by pre-HPLC to afford the title compound (0.75 g, 57.3%) as yellow solid.

104

5-chloro-N-((1R,3S)-3-(piperazin-1-yl)cyclohexyl)-4-(pyrazolo[1,5-a]pyridin-3-yl)pyrimidin-2-amine

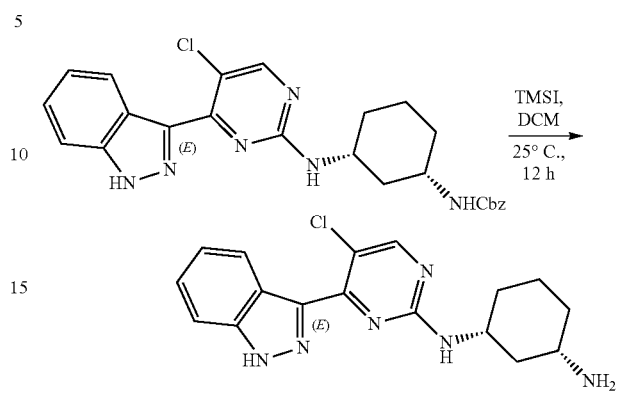

To a mixture of benzyl N-[(1S,3R)-3-[[5-chloro-4-(1H-indazol-3-yl)pyrimidin-2-yl]amino]cyclohexyl]carbamate (0.7 g, 1.5 mmol) in DCM (10 mL) was added TMSI (1.47 g, 7.3 mmol) at 25° C., the mixture was stirred for 12 h. The mixture was poured into water (20 mL), extracted with ethyl acetate (10 mL*2), and the aqueous phase was concentrated in vacuum to afford the title compound (0.32 g, crude)

Tert-butyl (4-(((1S,3R)-3-((5-chloro-4-(1H-indazol-3-yl)pyrimidin-2-yl)amino)cyclohexyl) carbamoyl) phenyl)carbamate

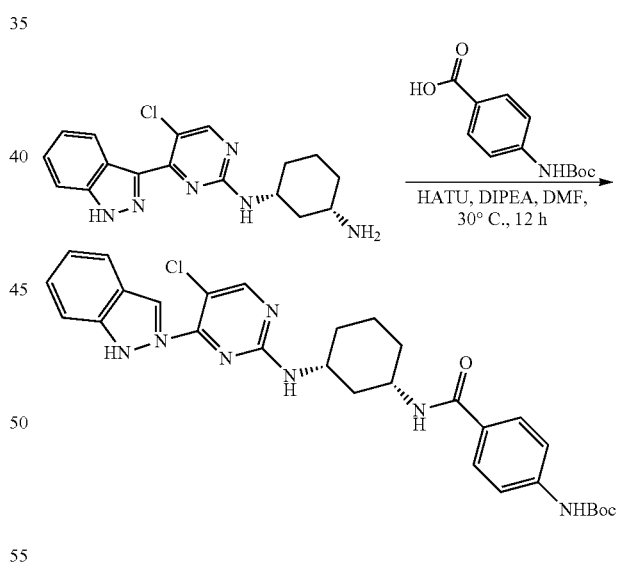

To a mixture of (1R,3S)—N1-[5-chloro-4-(1H-indazol-3-yl)pyrimidin-2-yl]cyclohexane-1,3-diamine (300 mg, 0.9 mmol) and 4-(tert-butoxycarbonylamino)benzoic acid (249.1 mg, 1.1 mmol) in DMF (10 mL) was added HATU (499.1 mg, 1.3 mmol) and DIPEA (226.2 mg, 1.8 mmol) at 30° C. and the mixture was stirred for 12 h. The mixture was poured into water (50 mL), extracted with EA (20 mL*2), and the combined organic phase was washed with saturated brine (50 mL*2), dried with anhydrous Na₂SO₄, and concentrated in vacuum. The residue was purified by silica gel chromatography to afford the title compound (200 mg, 25.8% for two steps).

4-amino-N-((1S,3R)-3-((5-chloro-4-(1H-indazol-3-yl)pyrimidin-2-yl)amino)cyclohexyl)benzamide (Compound 124)

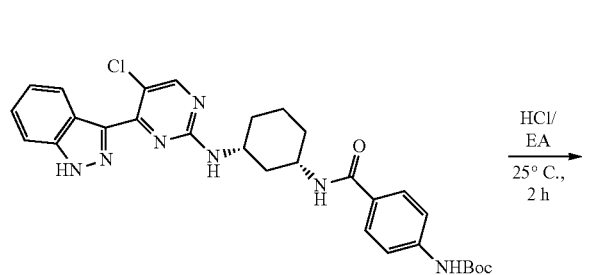

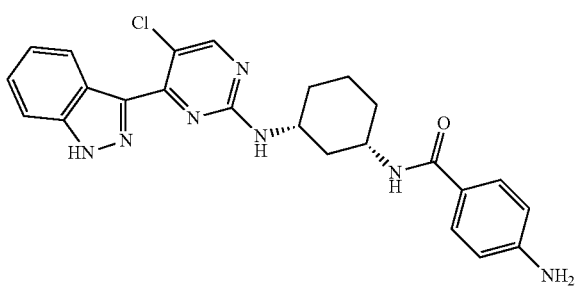

A mixture of tert-butyl N-[4-[[(1S,3R)-3-[[5-chloro-4-(1H-indazol-3-yl)pyrimidin-2-yl]amino]cyclohexyl]carbamoyl]phenyl]carbamate (200 mg, 0.35 mmol) in HCl/MeOH (20 mL) was stirred at 25° C. for 2 h. The mixture was concentrated in vacuum to afford the title compound (150 mg, crude). LCMS: ET1741-37-P2B (M+H$^+$): 462.2 @ 0.748 min (5-95% ACN in H$_2$O, 1.5 min).

Example 27. Synthesis of 4-amino-N-((1S,3R)-34 (5-chloro-4-(2-methyl-1H-indol-3-yl)pyrimidin-2-yl)amino)cyclohexyl)benzamide (Compound 126)

3-iodo-2-methyl-1H-indole

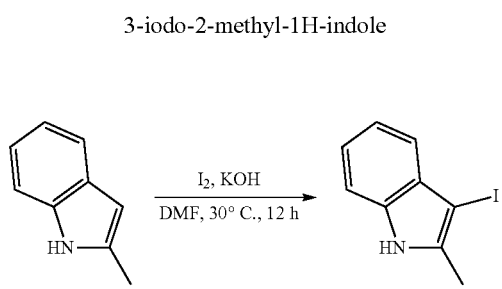

To a mixture of 2-methyl-1H-indole (20 g, 152.47 mmol) and KOH (21.39 g, 381.18 mmol) in DMF (200 mL) was added I$_2$(38.7 g, 152.47 mmol) at 30° C. and the mixture was stirred for 12 h. The mixture was poured into water, extracted with EA, and the organic layer was dried over Na$_2$SO$_4$ and concentrated and the residue was purified by column (PE:EA=15:1) to afford the title compound (25 g, 63.8%).

3-iodo-2-methyl-1-(phenylsulfonyl)-1H-indole

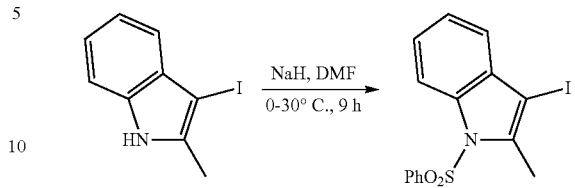

To a solution of 3-iodo-2-methyl-1H-indole (25 g, 97.25 mmol) in DMF (320 mL) was added NaH (4.67 g, 116.70 mmol) at 0° C. and the mixture was stirred at 30° C. for 1 h. Then benzenesulfonyl chloride (18.04 g, 102.11 mmol) was added and the mixture was stirred at 30° C. for 8 h. The mixture was poured into water, extracted with EA, and the organic layer was dried over Na$_2$SO$_4$ and concentrated. The residue was purified by column (PE:EA=20:1) to afford the title compound (28 g, 72.8%).

3-(2,5-dichloropyrimidin-4-yl)-2-methyl-1-(phenylsulfonyl)-1H-indole

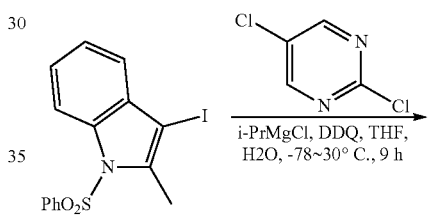

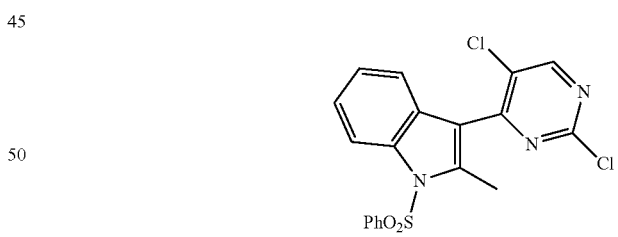

To a solution of 3-iodo-2-methyl-1-(phenylsulfonyl)-1H-indole (20 g, 50.35 mmol) in THF (400 mL) was added i-PrMgCl·LiCl (14.63 g, 100.70 mmol) at −78° C. and the mixture was stirred under N$_2$ for 1 h. Then 2,5-dichloropyrimidine (15 g, 100.70 mmol) was added at −78° C., the reaction was stirred at 30° C. for 3 h, then H$_2$O (2.09 g, 115.80 mmol) in THF (10 mL) was added at 0° C., finally DDQ (22.86 g, 100.70 mmol) was added, and the final mixture was stirred at 30° C. for 6 h. The mixture concentrated, diluted with water, extracted with EA, and the organic layer was concentrated. The residue was purified by column (PE:EA=10:1) to afford the title compound (6 g, 28.5%).

107

Benzyl ((1S, 3R)-3-((5-chloro-4-(2-methyl-1-(phenylsulfonyl)-1H-indol-3-yl)pyrimidin-2-yl)amino)cyclohexyl)carbamate

108

(1R,3S)—N1-(5-chloro-4-(2-methyl-1-(phenylsulfonyl)-1H-indol-3-yl)pyrimidin-2-yl)cyclohexane-1,3-diamine

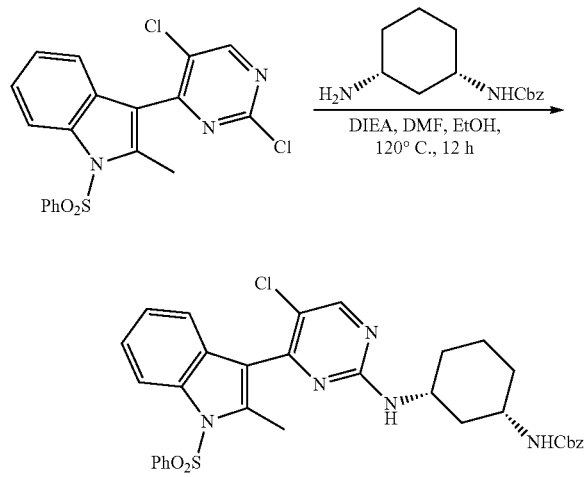

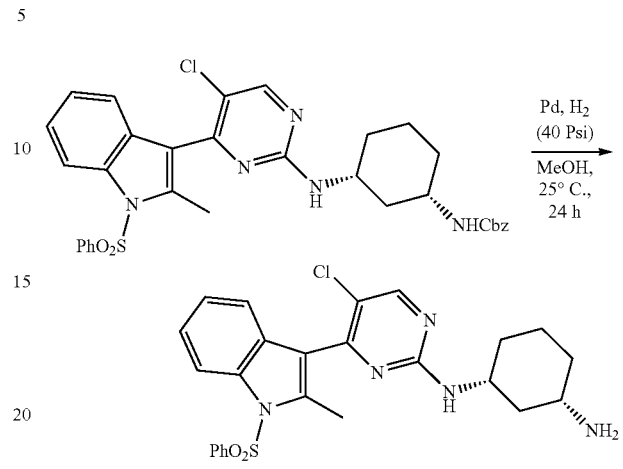

A mixture of 3-(2,5-dichloropyrimidin-4-yl)-2-methyl-1-(phenylsulfonyl)-1H-indole (5.0 g, 11.95 mmol), benzyl ((1S,3R)-3-aminocyclohexyl)carbamate (3.4 g, 11.95 mmol) and DIEA (5.41 g, 41.83 mmol) in DMF (30 mL) and EtOH (30 mL) was stirred at 120° C. for 12 h. The mixture was concentrated, and the residue was purified by column (PE:EA=4:1) to afford the title compound (5.1 g, 67.7%).

A mixture of benzyl ((1S,3R)-3-((5-chloro-4-(2-methyl-1-(phenylsulfonyl)-1H-indol-3-yl)pyrimidin-2-yl)amino)cyclohexyl)carbamate (5.0 g, 7.93 mmol) and Pd/C (0.80 g) in MeOH (100 mL) was stirred at 25° C. for 24 h under $H_2$ (40 psi). The mixture was filtered and concentrated to afford the title compound (2.7 g, crude).

Tert-butyl (4-(((1S, 3R)-3-((5-chloro-4-(2-methyl-1-(phenylsulfonyl)-1H-indol-3-yl)pyrimidin-2-yl)amino)cyclohexyl)carbamoyl)phenyl)carbamate

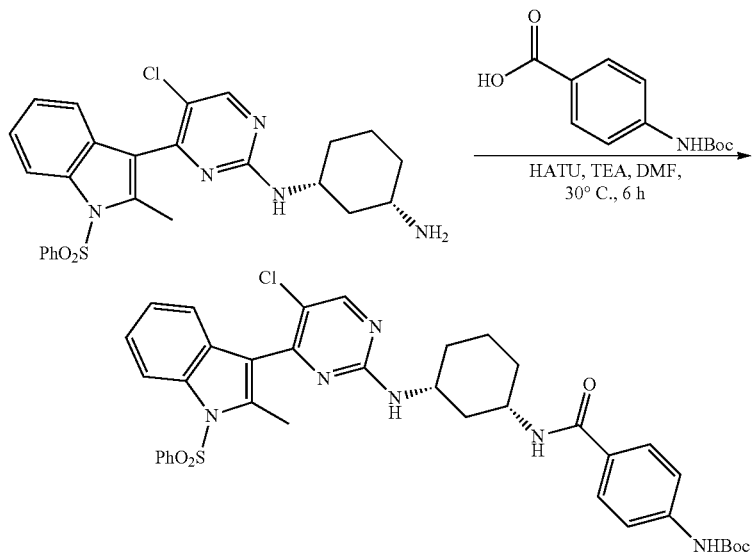

A mixture of (1R,3S)—N1-(5-chloro-4-(2-methyl-1-(phenylsulfonyl)-1H-indol-3-yl)pyrimidin-2-yl)cyclohexane-1,3-diaminetrifluoromethanesulfonate (1.5 g, 3.02 mmol), 4-((tert-butoxycarbonyl)amino)benzoic acid (0.72 g, 3.02 mol), HATU (1.21 g, 3.18 mmol) and DIEA (0.47 g, 3.63 mmol) in DMF (30 mL) was stirred at 30° C. for 6 h. The reaction solution was poured into water, extracted with EA, and the organic layer was dried and concentrated to afford the title compound (2.0, crude).

Tert-butyl (4-(((1S,3R)-34(5-chloro-4-(2-methyl-1H-indol-3-yl)pyrimidin-2-yl)amino)cyclohexyl)carbamoyl)phenyl)carbamate

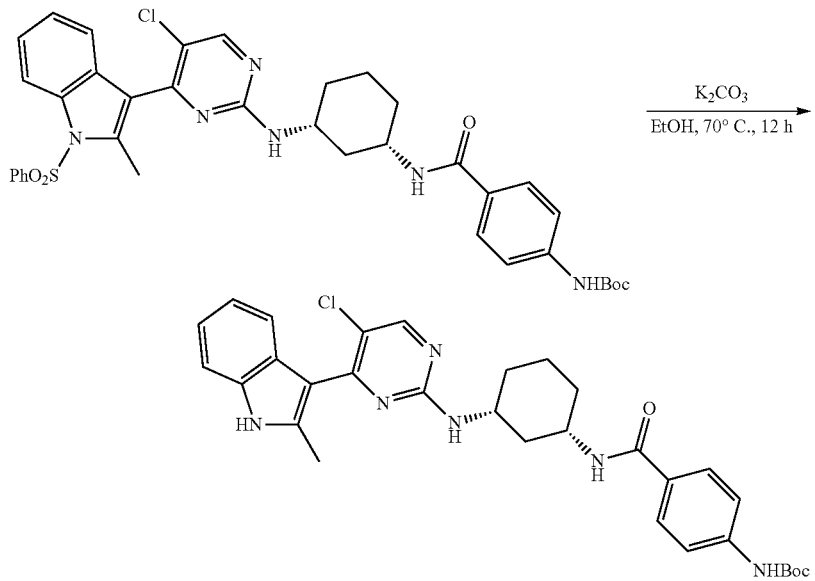

A mixture of tert-butyl (4-(((1S,3R)-3-((5-chloro-4-(2-methyl-1-(phenylsulfonyl)-1H-indol-3-yl)pyrimidin-2-yl)amino)cyclohexyl)carbamoyl)phenyl)carbamate (1.8 g, 2.52 mmol), K$_2$CO$_3$ (6.97 g, 0.44 mmol) and morpholine (0.44 g, 5.04 mmol) in EtOH (50 mL) was stirred at 70° C. for 12 h. The mixture was filtered, and the filtrate was concentrated to provide a residue that was purified by HPLC (acid condition) to afford the title compound (0.63 g, 43.6%).

4-amino-N-((1S,3R)-3-((5-chloro-4-(2-methyl-1H-indol-3-yl)pyrimidin-2-yl)amino)cyclohexyl)benzamide (Compound 126)

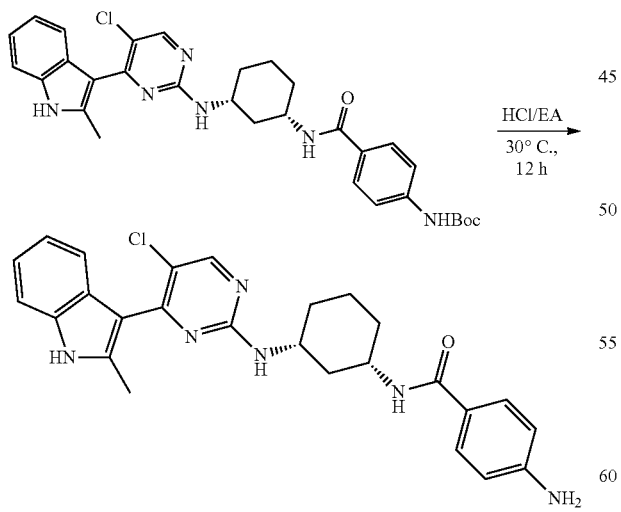

To a solution of tert-butyl (4-(((1S,3R)-3-((5-chloro-4-(2-methyl-1H-indol-3-yl)pyrimidin-2-yl)amino)cyclohexyl)carbamoyl)phenyl)carbamate (700 mg, 1.22 mmol) in EA (5 mL) was added into a solution of HCl/EA (25 mL) and the mixture was stirred at 30° C. for 12 h. The mixture was concentrated to afford the title compound (500 mg, 80.1%).

A mixture of (1R,3S)—N1-(5-chloro-4-(2-methyl-1-(phenylsulfonyl)-1H-indol-3-yl)pyrimidin-2-yl)cyclohexane-1,3-diaminetrifluoromethanesulfonate (1.5 g, 3.02 mmol), 4-((tert-butoxycarbonyl)amino)benzoic acid (0.72 g, 3.02 mol), HATU (1.21 g, 3.18 mmol) and DIEA (0.47 g, 3.63 mmol) in DMF (30 mL) was stirred at 30° C. for 6 h. The reaction solution was poured into water, extracted with EA, and the organic layer was dried and concentrated to afford the title compound (2.0, crude).

Example 28. Synthesis of 4-amino-3-fluoro-N-[(1S,3R)-3-[[4-(1H-indazol-3-yl)-5-(trifluoromethyl)pyrimidin-2-yl]amino]-1-methyl-cyclohexyl]benzamide (Compound 127)

2-(2-benzhydrylidenehydrazino)benzonitrile

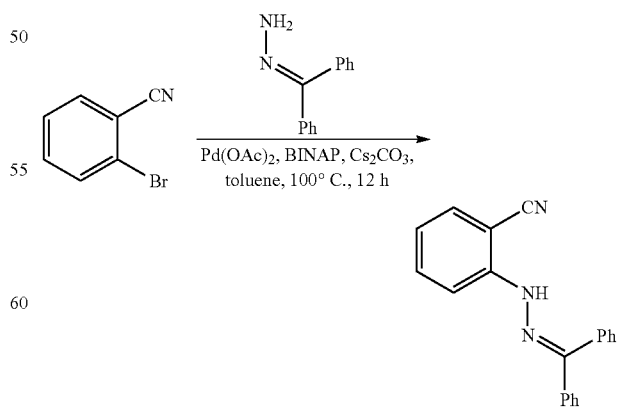

To a mixture of 2-bromobenzonitrile (27 g, 148 mmol), Cs$_2$CO$_3$ (68 g, 208 mmol) 2,2'-Bis(diphenylphosphino)-1, 1'-binaphthyl (5.5 g, 8.9 mmol) and diphenylmethanone hydrazone (32 g, 163 mmol) in toluene (100 mL) was added Pd(OAc)$_2$ (1.7 g, 7.4 mmol) under N$_2$. The mixture was heated to 100° C. and stirred for 12 h, then cooled to 25° C. and filtered. The filtrate was concentrated to afford the title compound (54 g, crude).

2-[(benzhydrylideneamino)-benzyl-amino]benzonitrile

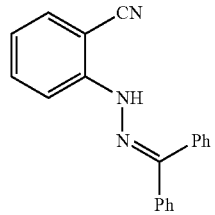

To a mixture of 2-(2-benzhydrylidenehydrazino)benzonitrile (54 g, 182 mmol) and (bromomethyl)benzene (47 g, 272 mmol) in DMF (200 mL) was added K$_2$CO$_3$ (50 g, 363 mmol) in one portion at 25° C. under N$_2$. The mixture was stirred at 25° C. for 12 h, then filtered. The filtrate was concentrated and purified by re-crystallization from EA (150 mL) and PE (500 mL) to afford the title compound (50 g, crude) as a yellow solid.

1-benzyl-1H-indazol-3-amine

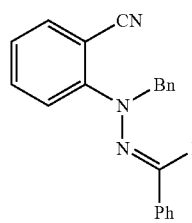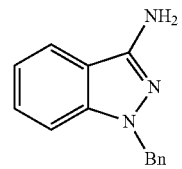

To a solution of 2-[(benzhydrylideneamino)-benzyl-amino]benzonitrile (21 g, 54 mmol) in MeOH (120 mL) was added 4-methylbenzenesulfonic acid (23 g, 135 mmol) in one portion at 25° C. under N$_2$. The mixture was heated to 80° C. and stirred for 12 h. The mixture was cooled to 25° C. and concentrated. The residue was dissolved with water. The aqueous phase was extracted with EA (150 mL*3). The combined organic phase were washed with saturated brine (150 mL), dried with anhydrous Na$_2$SO$_4$, filtered and concentrated in vacuum. The residue was purified by silica gel chromatography (PE/EA=5/1) to afford the title compound (10 g, 74%) as a yellow solid.

1-methyl-3-(4,4,5,5-tetramethyl-1,3,2-dioxaborolan-2-yl)indazole

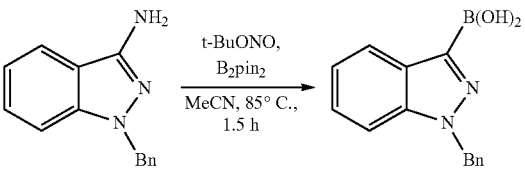 [SMILES: Nc1nn(Cc2ccccc2)c2ccccc12 ; OB(O)c1nn(Cc2ccccc2)c2ccccc12]

To a mixture of 1-benzylindazol-3-amine (6.5 g, 29 mmol) and 4,4,5,5-tetramethyl-2-(4,4,5,5-tetramethyl-1,3,2-dioxaborolan-2-yl)-1,3,2-dioxaborolane (10.4 g, 41 mmol) in MeCN (100 mL) was added tert-butyl nitrite (3.3 g, 32 mmol) in one portion at 25° C. under N$_2$. The mixture was heated to 85° C. and stirred for 1.5 h. The mixture was purified by prep-HPLC (TFA) to afford the title compound (2.6 g, 22%, TFA) as a yellow solid.

1-benzyl-3-[2-chloro-5-(trifluoromethyl)pyrimidin-4-yl]indazole

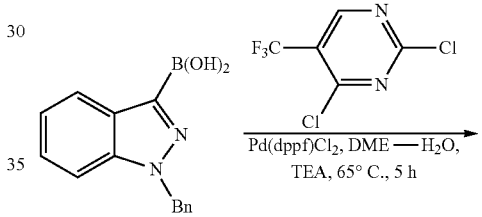

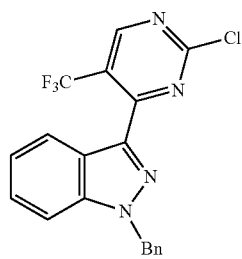

To a mixture of (1-benzylindazol-3-yl)boronic acid (1 g, 2.7 mmol, TFA) and 2,4-dichloro-5-(trifluoromethyl)pyrimidine (889 mg, 4.1 mmol) in H$_2$O (4 mL) and 1,2-dimethoxyethane (20 mL) was added Pd(dppf)Cl$_2$ (100 mg, 0.14 mmol) and TEA (553 mg, 5.5 mmol) under N$_2$. The mixture was heated to 65° C. and stirred for 5 h. The reaction mixture was concentrated under reduced pressure. The residue was diluted with water (30 mL) and extracted with DCM (30 mL*2). The combined organic layers were washed with brine (50 mL), dried over Na$_2$SO$_4$, filtered, concentrated and purified by column chromatography (SiO$_2$, PE/EA=40/1) to provide title compound (0.9 g, 76%) as a white solid.

Benzyl-((1S, 3R)-3-((4-(1-benzyl-3a,7a-dihydro-1H-indazol-3-yl)-5-(trifluoromethyl)pyrimidin-2-yl)amino)cyclohexyl)carbamate

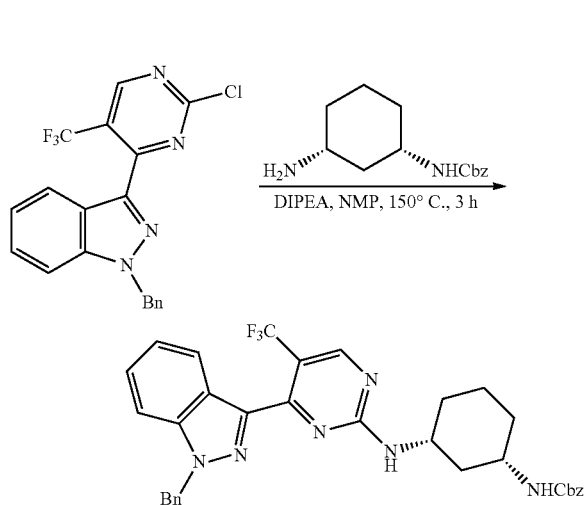

To a mixture of 1-benzyl-3-(2-chloro-5-(trifluoromethyl)pyrimidin-4-yl)-1H-indazole (700 mg, 1.8 mmol) and benzyl ((1S,3R)-3-aminocyclohexyl)carbamate (667 mg, 2.34 mmol HCl) in NMP (10 mL) was added DIPEA (698 mg, 5.4 mmol). The mixture was heated to 150° C. and stirred for 3 h, then cooled to 25° C. and poured into water (30 mL). The aqueous phase was filtered. The cake was dried under reduced pressure to afford the title compound (800 mg, 49%) as a white solid.

(1R,3S)—N1-[4-(1-benzylindazol-3-yl)-5-(trifluoromethyl)pyrimidin-2-yl]cyclohexane-1,3-diamine

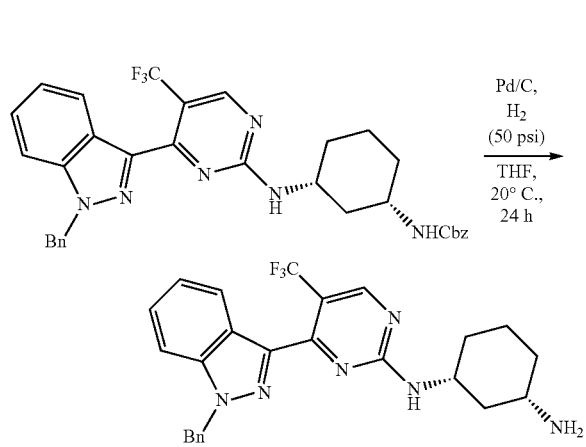

To a solution of benzyl N-[(1S,3R)-3-[[4-(1-benzyl-3a,7a-dihydroindazol-3-yl)-5-(trifluoromethyl)pyrimidin-2-yl]amino]cyclohexyl]carbamate (800 mg, 1.33 mmol) in THF (30 mL) was added Pd/C (2 g) under $N_2$. The suspension was degassed under vacuum and purged with $H_2$ several times. The reaction was stirred under $H_2$ (50 psi) at 20° C. for 24 h. The reaction mixture was filtered and concentrated under reduced pressure to give the title compound (500 mg, crude) as a white solid.

(1R,3S)—N1-[4-(1H-indazol-3-yl)-5-(trifluoromethyl)pyrimidin-2-yl]cyclohexane-1,3-diamine

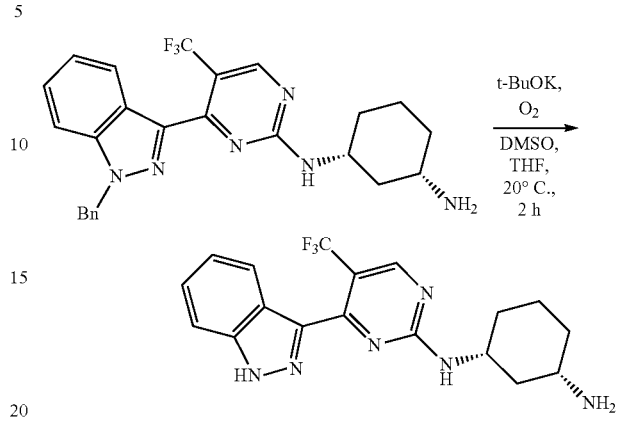

To a solution of (1R,3S)—N1-[4-(1-benzylindazol-3-yl)-5-(trifluoromethyl)pyrimidin-2-yl]cyclohexane-1,3-diamine (500 mg, 1.07 mmol) in DMSO (2 mL) and THF (2 mL) was added t-BuOK (960 mg, 8.56 mmol) under $N_2$. Then oxygen was bubbled into the reaction at 20° C. for 2 h. The reaction mixture was quenched by addition of TFA to pH=6. The mixture was purified by prep-HPLC (TFA) to give the title compound (400 mg, 76%, TFA) as a yellow solid.

4-amino-3-fluoro-N-[(1S,3R)-3-[[4-(1H-indazol-3-yl)-5-(trifluoromethyl)pyrimidin-2-yl]amino]-1-methyl-cyclohexyl]benzamide (Compound 127)

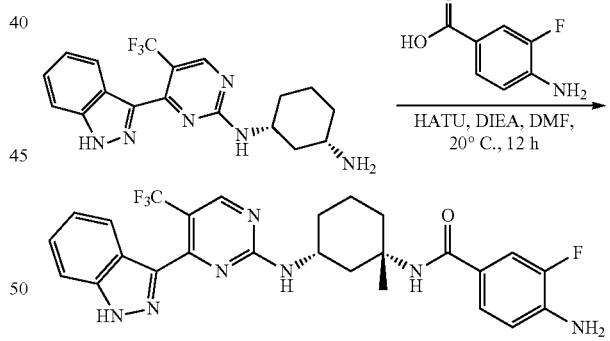

To a mixture of (1S,3R)—N3-[4-(1H-indazol-3-yl)-5-(trifluoromethyl)pyrimidin-2-yl]-1-methyl-cyclohexane-1,3-diamine (60 mg, 102 μmol, TFA) and 4-amino-3-fluoro-benzoic acid (14.6 mg, 92 μmol) in DMF (2 mL) was added DIEA (68 mg, 512 μmol) and HBTU (39.6 mg, 102 μmol) under $N_2$. The mixture was stirred at 20° C. for 12 h. The mixture was purified by prep-HPLC (HCl) to provide the title compound (7.3 mg, 13%, HCl) as a yellow solid. LCMS: (M+H$^+$): 528.3 @ 3.006 min (10-80% ACN in $H_2O$, 4.5 min). $^1$H NMR: (MeOD, 400 MHz): δ 8.64 (s, 1H), 8.45 (s, 1H), 8.67-8.51 (m, 4H), 7.37 (s, 1H), 7.14 (s, 1H), 4.57-4.50 (m, 1H), 2.65 (s, 1H), 2.16 (s, 1H), 2.04-1.95 (m, 3H), 1.91-1.52 (m, 6H).

Example 29. Synthesis of 4-amino-N-((1S,3R)-34 (5-chloro-4-(1H-indol-3-yl) pyrimidin-2-yl)amino)-1-methylcyclohexyl)benzamide (Compound 128)

tert-butyl (4-(((1S,3R)-34(5-chloro-4-(1H-indol-3-yl)pyrimidin-2-yl)amino)-1-methylcyclohexyl) carbamoyl)phenyl)carbamate

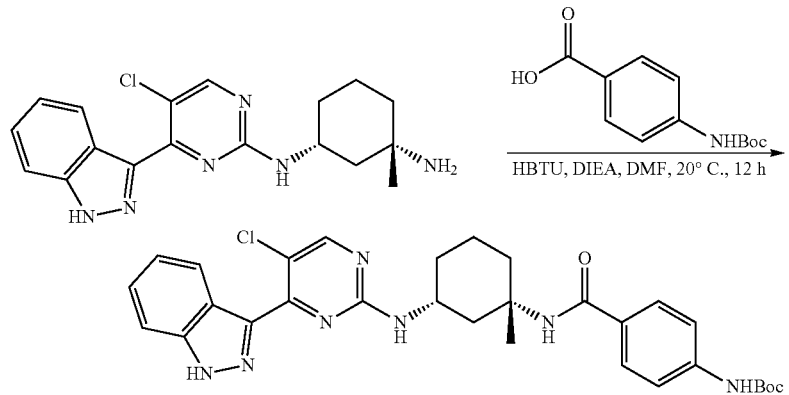

To a solution of (1R,3S)—N1-(5-chloro-4-(1H-indol-3-yl)pyrimidin-2-yl)-3-methyl-cyclohexane-1,3-diamine (1.0 g, 2.81 mmol), and 4-((tert-butoxycarbonyl)amino)benzoic acid (0.73 g, 3.09 mmol) in DMF (20 mL) was added HBTU (1.4 g, 3.65 mmol) and DIPEA (0.54 g, 4.22 mmol). The mixture was stirred at 20° C. for 12 h, then diluted with water (30 mL) and extracted with EA (50 mL*3). The organic layer was combined, dried over $Na_2SO_4$, filtered, and concentrated. The residue was purified by column chromatography ($SiO_2$, PE/EA=5:1 to 2:1) to give title compound (1.5 g, 92.8%)

4-amino-N-((1S,3R)-34(5-chloro-4-(1H-indol-3-yl) pyrimidin-2-yl)amino)-1-methylcyclohexyl)benzamide (Compound 128)

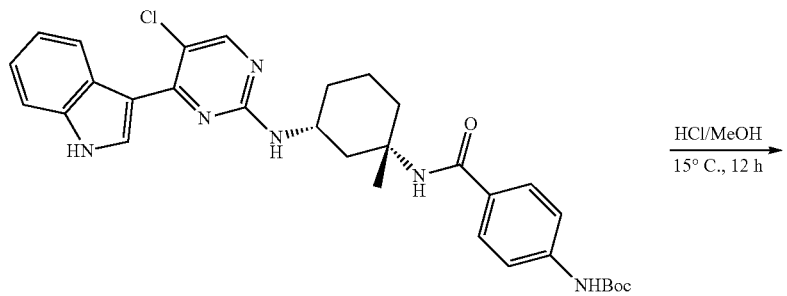

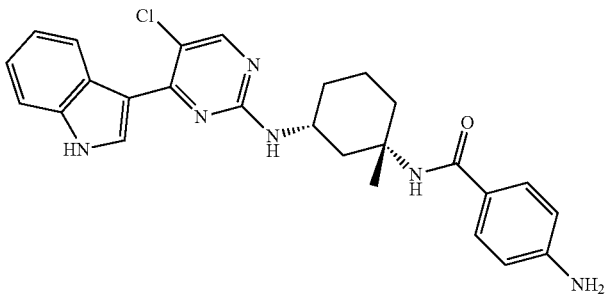

To a solution of tert-butyl(4-(((1S,3R)-3-((5-chloro-4-(1H-indol-3-yl)pyrimidin-2-yl) amino)-1-methylcyclohexyl)carbamoyl)phenyl)carbamate (100 mg, 0.17 mmol) was added HCl/MeOH (50 mL), and the mixture was stirred at 15° C. for 12 h. The reaction mixture was concentrated, and the residue was purified by prep-HPLC (HCl) to afford the title compound (40 mg, 48.4%). LCMS: M+H$^+$: 475.3@ 2.472 min (10-80% ACN in H$_2$O, 4.5 min). $^1$H NMR (MeOD, 400 MHz): δ 8.67 (d, J=7.53 Hz, 1H), 8.48 (br. s., 1H), 8.26 (br. s., 1H), 7.53 (d, J=8.53 Hz, 2H), 7.23-7.12 (m, 3H), 6.51 (d, J=8.53 Hz, 2H), 5.53 (br. s., 2H), 4.11 (br. s., 1H), 2.34 (br. s., 2H), 1.94 (d, J=12.05 Hz, 2H), 1.75 (d, J=8.03 Hz, 3H), 1.52 (br. s., 4H), 1.31 (d, J=11.54 Hz, 1H).

Example 30. Synthesis of 3-chloro-4-[[4-(dimethylamino)-3-hydroxy-butanoyl]amino]-N-[(1S,3R)-3-[[4-(1H-indazol-3-yl)-5-(trifluoromethyl)pyrimidin-2-yl]amino]-1-methyl-cyclohexyl]benzamide (Compound 129)

4-amino-3-chloro-N-[(1 S, 3R)-3-[[4-(1H-indazol-3-yl)-5-(trifluoromethyl)pyrimidin-2-yl]amino]-1-methyl-cyclohexyl]benzamide

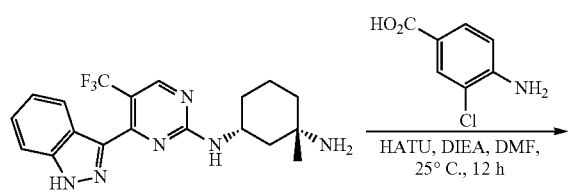

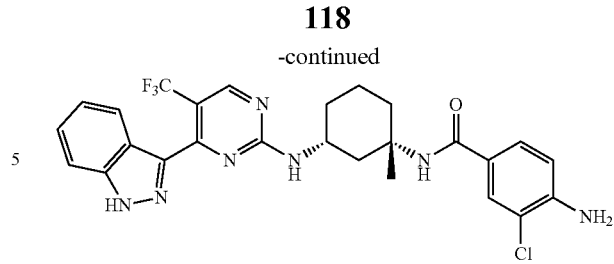

A solution of 4-amino-3-chloro-benzoic acid (68.03 mg, 396.49 mol), HATU (158.30 mg, 416.31 μmol) and DIPEA (102.48 mg, 792.98 mol) in DMF (10 mL) was stirred at 25° C. for 0.5 h, then (1S,3R)—N3-[4-(1H-indazol-3-yl)-5-(trifluoromethyl)pyrimidin-2-yl]-1-methyl-cyclohexane-1,3-diamine (200 mg, 396.49 mol, TFA) was added. The mixture was stirred at 25° C. for 11.5 h, then diluted with water (60 mL). The aqueous phase was extracted with ethyl acetate (50 mL*3), and the combined organic phase was washed with brine (50 mL*2), dried over anhydrous Na$_2$SO$_4$, filtered, and concentrated under vacuum. The residue was purified by silica gel chromatography (DCM:MeOH=120:1-100:1-80:1) to afford the title compound (170 mg, 78%) as white solid.

3-chloro-4-[[4-(dimethylamino)-3-hydroxy-butanoyl]amino]-N-[(1 S,3R)-3-[[4-(1H-indazol-3-yl)-5-(trifluoromethyl)pyrimidin-2-yl]amino]-1-methyl-cyclohexyl]benzamide (Compound 129)

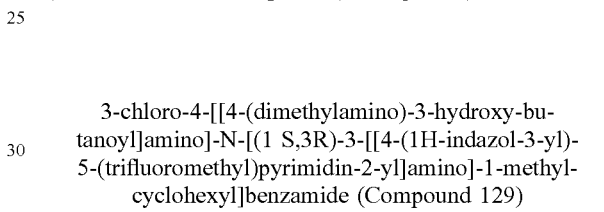

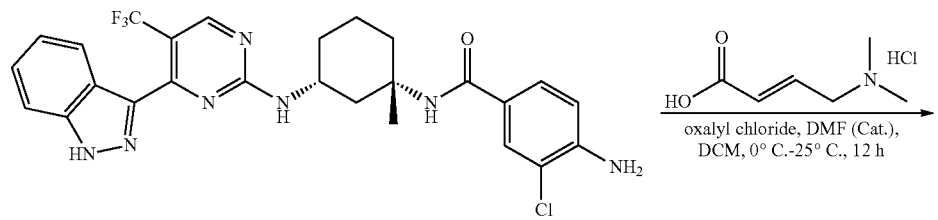

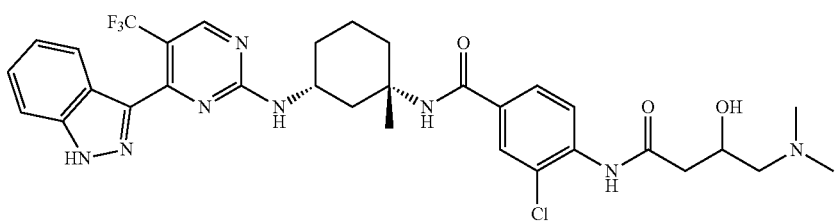

To a stirred solution of (E)-4-(dimethylamino)but-2-enoic acid (121.04 mg, 735.35 mol) in DCM (2 mL) was added oxalyl dichloride (93.33 mg, 735.35 mol) at 0° C., followed by DMF (4.9 mg, 0.14 mol), then the reaction mixture was stirred at 0° C. for 1 h. The solution was then added to a mixture of 4-amino-3-chloro-N-[(1S,3R)-3-[[4-(1H-indazol-3-yl)-5-(trifluoromethyl)pyrimidin-2-yl]amino]-1-methyl-cyclohexyl]benzamide (80 mg, 147.07 µmol) and pyridine (34.90 mg, 441.21 mol) in THF (3 mL) and NMP (3 mL). After the addition the mixture was stirred at 25° C. for 11 h, at which point the mixture was concentrated under vacuum. The residue was purified by prep-HPLC (neutral) to afford the title compound (28.6 mg, 28%) as white solid. LCMS: ET3428-395-P1A, M+H$^+$: 673.3@2.576 min (10-80% ACN in H$_2$O, 4.5 min). $^1$H NMR ET3428-395-P1A (MeOD, 400 MHz) δ 8.61 (s, 1H), 7.75 (s, 1H), 7.64-7.63 (m, 2H), 7.51 (s, 1H), 7.44-7.41 (m, 1H), 7.24 (s, 1H), 6.91 (s, 1H), 4.8 (m, 2H), 4.27 (s, 2H), 2.86 (s, 6H), 2.64-2.60 (m, 3H), 2.08-2.01 (m, 1H), 1.99-1.91 (m, 1H), 1.85-1.81 (m, 3H), 1.66-1.63 (m, 1H), 1.57 (s, 3H), 1.45-1.42 (m, 1H).

Example 31. Synthesis of 3-fluoro-4-(methylamino)-N-[(1S,3R)-1-methyl-3-[[4-(7-methyl-1H-indol-3-yl)-5-(trifluoromethyl)pyrimidin-2-yl]amino]cyclohexyl]benzamide (Compound 130)

Benzyl N-[(1 S, 3R)-1-methyl-3-[[4-(7-methyl-1H-indol-3-yl)-5-(trifluoromethyl) pyrimidin-2-yl]amino]cyclohexyl]carbamate

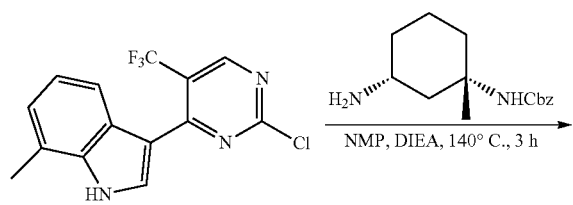

A solution of 3-[2-chloro-5-(trifluoromethyl)pyrimidin-4-yl]-7-methyl-1H-indole (4.7 g, 14.93 mmol), benzyl N-[(1S,3R)-3-amino-1-methyl-cyclohexyl]carbamate (3.92 g, 14.93 mmol) and DIEA (4.82 g, 37.32 mmol) in NMP (40 mL) was stirred at 140° C. for 3 h. The mixture was diluted with water (100 mL), and the aqueous phase was extracted with ethyl acetate (50 mL*3). The combined organic phase was washed with brine (50 mL*3), dried over anhydrous Na$_2$SO$_4$, filtered and concentrated in vacuum. The residue was purified by silica gel chromatography (PE:EA=10:1-5:1-3:1) to give the title compound (8 g, 92%) as a yellow solid.

(1S,3R)-1-methyl-N3-[4-(7-methyl-1H-indol-3-yl)-5-(trifluoromethyl)pyrimidin-2-yl]cyclohexane-1,3-diamine

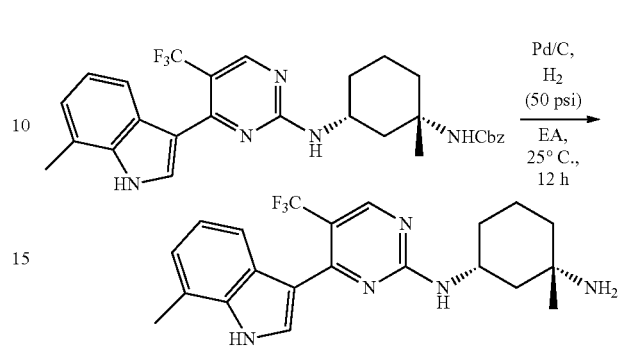

A solution of benzyl N-[(1S,3R)-1-methyl-3-[[4-(7-methyl-1H-indol-3-yl)-5-(trifluoromethyl)pyrimidin-2-yl]amino]cyclohexyl]carbamate (6 g, 11.16 mmol), Pd/C (2 g, 10% wet) in EA (80 mL) was stirred at 25° C. under H$_2$ (50 psi) for 12 h. The mixture was filtered through a celite pad and the filtrate was concentrated under vacuum to give the title compound (5 g, crude) as a white solid and used directly in next step without further purification.

4-amino-3-fluoro-N-[(1S,3R)-1-methyl-3-[[4-(7-methyl-1H-indol-3-yl)-5-(trifluoromethyl)pyrimidin-2-yl]amino]cyclohexyl]benzamide

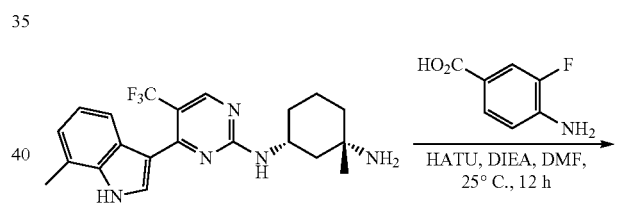

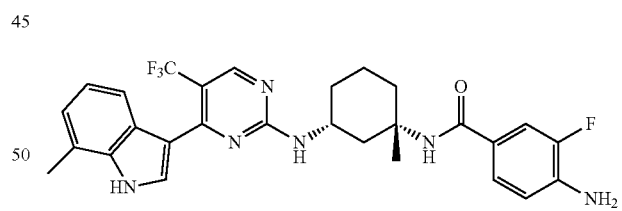

A solution of (1S,3R)-1-methyl-N3-[4-(7-methyl-1H-indol-3-yl)-5-(trifluoromethyl)pyrimidin-2-yl]cyclohexane-1, 3-diamine (600 mg, 1.49 mmol), 4-amino-3-fluorobenzoic acid (231.14 mg, 1.49 mmol), HATU (623.20 mg, 1.64 mmol) and DIPEA (288.85 mg, 2.24 mmol) in DMF (15 mL) was stirred at 25° C. for 12 h. The mixture was diluted with water (50 mL), and the aqueous phase was extracted with ethyl acetate (50 mL*3). The combined organic phase was washed with brine (20 mL*3), dried over anhydrous Na$_2$SO$_4$, filtered and concentrated in vacuum. The residue was purified by silica gel chromatography (DCM:MeOH=120:1-100:1-70:1) to give the title compound (600 mg, 69%) as a yellow solid.

3-fluoro-4-(methylamino)-N-[(1S,3R)-1-methyl-3-[[4-(7-methyl-1H-indol-3-yl)-5-(trifluoromethyl)pyrimidin-2-yl]amino]cyclohexyl]benzamide (Compound 130)

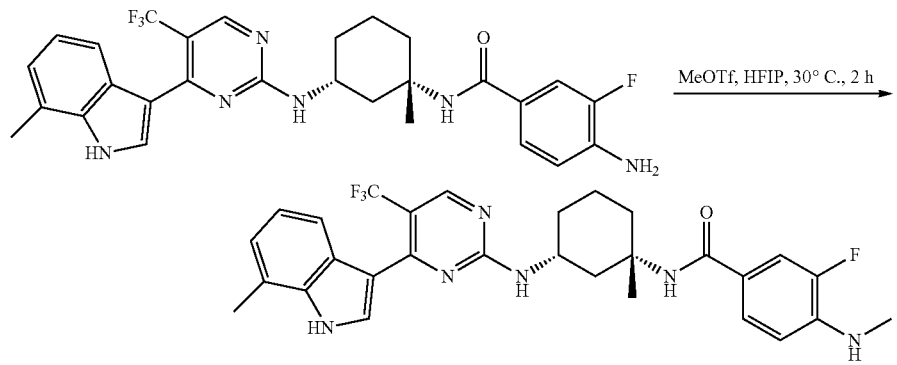

A solution of 4-amino-3-fluoro-N-[(1S,3R)-1-methyl-3-[[4-(7-methyl-1H-indol-3-yl)-5-(trifluoromethyl)pyrimidin-2-yl]amino]cyclohexyl]benzamide (250 mg, 462.49 μmol) and methyl trifluoromethanesulfonate (60.72 mg, 369.99 μmol) in HFIP (10 mL) was stirred at 30° C. for 2 h. The reaction was quenched with HCl (1 N, 30 mL) and extracted with EA (30 mL*3), then the combined organic phase was dried over anhydrous $Na_2SO_4$, filtered, and concentrated under vacuum. The residue was purified by prep-TLC (PE: EA=2:1) and prep-HPLC (TFA). The solution of prep-HPLC was based with sat. $NaHCO_3$ (10 mL) and extracted with ethyl acetate (30 mL*3). The combined organic phase was dried over anhydrous $Na_2SO_4$, filtered and concentrated in vacuum to give title compound (50 mg, 19%) as yellow oil. The residue (40 mg) was purified by prep-HPLC (HCl) to give 3-fluoro-4-(methylamino)-N-[(1S,3R)-1-methyl-3-[[4-(7-methyl-1H-indol-3-yl)-5-(trifluoromethyl)pyrimidin-2-yl]amino]cyclohexyl]benzamide (27.1 mg, HCl salt). LCMS: $M+H^+$: 555.3 @3.173 min (10-80% ACN in $H_2O$, 4.5 min). $^1H$ NMR (MeOD, 400 MHz) δ 8.47 (s, 1H), 8.37 (s, 1H), 8.18 (s, 1H), 7.49 (d, J=7.6 Hz, 1H), 7.40 (d, J=12.8 Hz, 1H), 7.19-7.13 (m, 2H), 6.67 (s, 1H), 4.55-4.51 (m, 1H), 2.85 (s, 3H), 2.56 (s, 3H), 2.16-2.03 (m, 2H), 1.94-1.87 (m, 3H), 1.74-1.70 (m, 1H), 1.67-1.46 (m, 4H), 1.28 (s, 1H).

Example 32. CDK7 Kinase Activity

Compounds of the invention were assayed for CDK7 activity at Life Technologies™ (Grand Island, N.Y.) using their commercially available Adapta® kinase assay services. Test compounds were tested at concentrations ranging from 10 μM down to 0.514 nM in a series of 3-fold serial dilutions. Details of this assay, including substrates used, are available on the Life Technologies web site (http://www.lifetechnologies.com/us/en/home/life-science/drug-discovery/target-and-lead-identification-and-validation/kinasebiology/kinase-activity-assays.html). The results of the assay are shown below in Table 3 where "A" represents a calculated $IC_{50}$ of less than 100 nM; "B" represents a calculated $IC_{50}$ of between 100 nM and 1 μM; and "C" represents a calculated $IC_{50}$ of greater than 1 μM.

TABLE 3

CDK7 Inhibitory Activity of Selected Compounds of the Invention.

| Compound No. | CDK7 Inhibition ($IC_{50}$) |
|---|---|
| 100 | C |
| 101 | A |
| 102 | B |
| 103 | B |
| 104 | B |
| 105 | A |
| 106 | A |
| 107 | A |
| 108 | C |
| 109 | B |
| 110 | B |
| 111 | B |
| 112 | B |
| 113 | B |
| 114 | C |

Example 33. Inhibition of Cell Proliferation

Representative compounds of the invention were tested at different concentrations (from 10 μM to 316 pM; 0.5 log serial dilutions) for their ability to inhibit the proliferation of Jurkat cells. Known CDK inhibitors flavopiridol and triptolide were used as positive controls. Cells were grown in RPMI 1640+10% FBS+1% Glutamax. The cells were supplemented with FBS (Life Technologies) and 100 $U·mL^{-1}$ penicillin, 100 $μg·mL^{-1}$ streptomycin (Invitrogen) and cultured at 37° C. in a humidified chamber in the presence of 5% $CO_2$. Proliferation assays were conducted over a 72 hour time period. CellTiter-Glo® (Promega Corporation, Madison, Wis. USA) was used to assess the anti-proliferative effects of the compounds following manufacturer's directions and utilizing the reagents supplied with the CellTiter-Glo® kit. In this table, "A" represents an $IC_{50}$ of less than 500 nM; "B" an $IC_{50}$ of between 500 nM and 5 μM; and "C" an $IC_{50}$ of greater than 5 μM.

TABLE 4

Inhibition of Proliferation of Jurkat Cells by Compounds of the Invention.

| Compound No. | Jurkat IC$_{50}$ |
|---|---|
| 101 | B |
| 102 | C |
| 103 | C |
| 104 | C |
| 105 | B |
| 106 | C |
| 107 | A |
| 108 | C |
| 109 | B |
| 111 | C |
| 112 | B |
| 113 | B |

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one or all of the group members are present in, employed in, or otherwise relevant to a given product or process.

Furthermore, the invention encompasses all variations, combinations, and permutations in which one or more limitations, elements, clauses, and descriptive terms from one or more of the listed claims are introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed is:

1. A pharmaceutical composition comprising a pharmaceutically acceptable excipient and a therapeutically effective amount of a compound having the structural formula I:

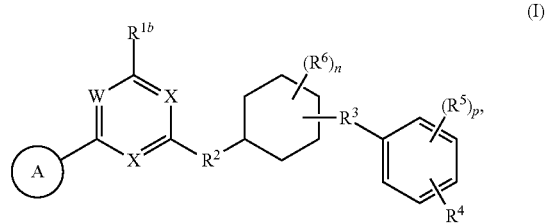

or a pharmaceutically acceptable salt, isotopically labeled derivative, or stereoisomer thereof, wherein ring A is an optionally substituted heteroaryl ring of Formula (i-1), (i-2), (i-3), (i-4), (i-5) or (i-6):

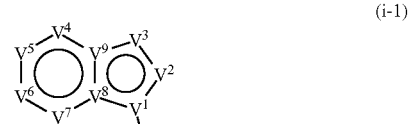

(i-1)

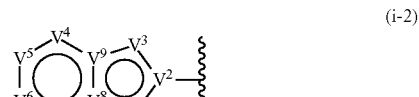

(i-2)

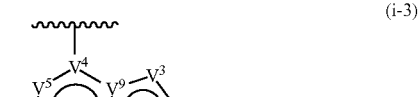

(i-3)

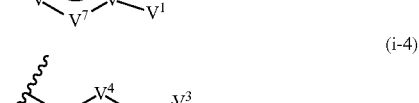

(i-4)

125

-continued (i-5)

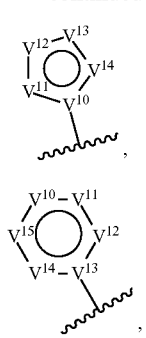

(i-6)

wherein
each instance of $V^1$, $V^2$, $V^3$, $V^4$, $V^5$, $V^6$, $V^7$, $V^8$, $V^9$, $V^{10}$, $V^{11}$, $V^{12}$, $V^{13}$, $V^{14}$ and $V^{15}$ is, independently, O, S, N, $N(R^{A1})$, C, or $C(R^{A2})$;
each instance of $R^{A1}$ is, independently, hydrogen, deuterium, optionally substituted acyl, optionally substituted alkyl, optionally substituted alkenyl, optionally substituted alkynyl, optionally substituted carbocyclyl, optionally substituted heterocyclyl, optionally substituted aryl, or optionally substituted heteroaryl;
each instance of $R^{A2}$ is, independently, hydrogen, deuterium, halogen, —CN, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, —$OR^{A2a}$, —$N(R^{A2a})_2$, or —$SR^{A2a}$, wherein each occurrence of $R^{A2a}$ is, independently, hydrogen, optionally substituted acyl, optionally substituted alkyl, optionally substituted alkenyl, optionally substituted alkynyl, optionally substituted carbocyclyl, optionally substituted heterocyclyl, optionally substituted aryl, or optionally substituted heteroaryl, or
any two $R^{A1}$, any two $R^{A2}$, or one $R^{A1}$ and one $R^{A2}$ are joined to form an optionally substituted carbocyclic, optionally substituted heterocyclic, optionally substituted aryl, or optionally substituted heteroaryl ring;
each X is, independently, N or CH, wherein at least one X is N;
W is N or $C(R^{1a})$;
each of $R^{1a}$, if present, and $R^{1b}$ is, independently, hydrogen, deuterium, halogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, —CN, —$OR^{B1a}$, —$N(R^{B1a})_2$, or —$SR^{B1a}$, wherein each occurrence of $R^{B1a}$ is, independently, hydrogen, optionally substituted acyl, optionally substituted alkyl, optionally substituted alkenyl, optionally substituted alkynyl, optionally substituted carbocyclyl, optionally substituted heterocyclyl, optionally substituted aryl, or optionally substituted heteroaryl, or
$R^{1a}$ and $R^{1b}$ are joined to form an optionally substituted carbocyclic, optionally substituted heterocyclic, optionally substituted aryl, or optionally substituted heteroaryl ring;
$R^2$ is an optionally substituted $C_1$-$C_4$ alkylene or an optionally substituted $C_2$-$C_4$ alkenylene or alkynylene, wherein one or more methylene units of the alkylene,

126 alkenylene or alkynylene are optionally and independently replaced with —O—, —S—, or —$N(R^7)$—;
$R^3$ is a bond, an optionally substituted $C_1$-$C_4$ alkylene, or an optionally substituted $C_2$-$C_4$ alkenylene or alkynylene, wherein one or more methylene units of the alkylene, alkenylene or alkynylene is optionally and independently replaced with —O—, —S—, —$N(R^7)$—, or —$S(O)_2$—;
$R^4$ is —$NH_2$, —NH—C(O)—$(CH_2)_3$—$N(CH_3)_2$, —NH—C(O)—$CH_2$—CH(OH)—$CH_2$—$N(CH_3)_2$, —NH—$CH_3$, or —NH—C(O)—C(O)—$NH_2$;
p is 0, 1, 2 or 3,
wherein the compound is other than

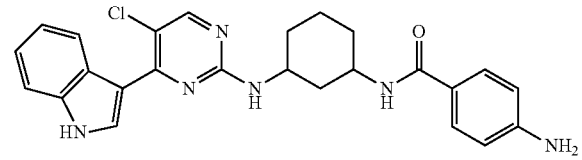 [SMILES: Nc1ccc(C(=O)NC2CCCC(Nc3ncc(Cl)c(-c4c[nH]c5ccccc45)n3)C2)cc1]

or a pharmaceutically acceptable salt, isotopically labeled derivative or stereoisomer thereof.
2. The pharmaceutical composition of claim 1, wherein, within the compound or the pharmaceutically acceptable salt, isotopically labeled derivative, or stereoisomer thereof, ring A is a heteroaryl ring of Formula (i-1), (i-2), (i-3), (i-4), (i-5) or (i-6) optionally substituted with methyl;
each instance of $R^{A1}$ is, independently, hydrogen, deuterium, unsubstituted acyl, unsubstituted alkyl, unsubstituted alkenyl, unsubstituted alkynyl, unsubstituted carbocyclyl, unsubstituted heterocyclyl, unsubstituted aryl, or unsubstituted heteroaryl;
each instance of $R^{A2}$ is, independently, hydrogen, deuterium, halogen, —CN, unsubstituted acyl, unsubstituted alkyl, unsubstituted alkenyl, unsubstituted alkynyl, unsubstituted carbocyclyl, unsubstituted heterocyclyl, unsubstituted aryl, unsubstituted heteroaryl, —$OR^{A2a}$, —$N(R^{A2a})_2$, or —$SR^{A2a}$, wherein each occurrence of $R^{A2a}$ is, independently, hydrogen, unsubstituted acyl, unsubstituted alkyl, unsubstituted alkenyl, unsubstituted alkynyl, unsubstituted carbocyclyl, unsubstituted heterocyclyl, unsubstituted aryl, or unsubstituted heteroaryl, or
any two $R^{A1}$, any two $R^{A2}$, or one $R^{A1}$ and one $R^{A2}$ are joined to form an unsubstituted carbocyclic, unsubstituted heterocyclic, unsubstituted aryl, or unsubstituted heteroaryl ring;
each X is, independently, N or CH, wherein at least one X is N;
W is N or $C(R^{1a})$;
each of $R^{1a}$, if present, and $R^{1b}$ is, independently, hydrogen, deuterium, halogen, unsubstituted acyl, unsubstituted alkyl, unsubstituted alkenyl, unsubstituted alkynyl, unsubstituted carbocyclyl, unsubstituted heterocyclyl, unsubstituted aryl, unsubstituted heteroaryl, —CN, —$OR^{B1a}$, —$N(R^{B1a})_2$, or —$SR^{B1a}$, wherein each occurrence of $R^{B1a}$ is, independently, hydrogen, unsubstituted acyl, unsubstituted alkyl, unsubstituted alkenyl, unsubstituted alkynyl, unsubstituted carbocyclyl, unsubstituted heterocyclyl, unsubstituted aryl, or unsubstituted heteroaryl, or
$R^{1a}$ and $R^{1b}$ are joined to form an unsubstituted carbocyclic, unsubstituted heterocyclic, unsubstituted aryl, or unsubstituted heteroaryl ring;

R² is an unsubstituted C₁-C₄ alkylene or an unsubstituted C₂-C₄ alkenylene or alkynylene, wherein one or more methylene units of the alkylene, alkenylene or alkynylene are optionally and independently replaced with —O—, —S—, or —N(R⁷)—;

R³ is a bond, a C₁-C₄ alkylene optionally substituted with =O or =S, or an unsubstituted C₂-C₄ alkenylene or alkynylene, wherein one or more methylene units of the alkylene, alkenylene or alkynylene is optionally and independently replaced with —O—, —S—, —N(R⁷)—, or —S(O)₂—;

R⁴ is —NH₂, —NH—C(O)—(CH₂)₃—N(CH₃)₂, —NH—C(O)—CH₂—CH(OH)—CH₂—N(CH₃)₂, —NH—CH₃, or —NH—C(O)—C(O)—NH₂;

each R⁵, if present, is, independently, deuterium, halogen, unsubstituted acyl, unsubstituted alkyl, unsubstituted alkenyl, unsubstituted alkynyl, unsubstituted carbocyclyl, unsubstituted heterocyclyl, unsubstituted aryl, unsubstituted heteroaryl, —OR^{D1}, —N(R^{D1})₂, or —SR^{D1}, wherein each occurrence of R^{D1} is, independently, hydrogen, unsubstituted acyl, unsubstituted alkyl, unsubstituted alkenyl, unsubstituted alkynyl, unsubstituted carbocyclyl, unsubstituted heterocyclyl, unsubstituted aryl, or unsubstituted heteroaryl;

each R⁶, if present, is, independently, deuterium, halogen, unsubstituted acyl, unsubstituted alkyl, unsubstituted alkenyl, unsubstituted alkynyl, unsubstituted carbocyclyl, unsubstituted heterocyclyl, unsubstituted aryl, unsubstituted heteroaryl, =O, —CN, —OR^{C1}, —N(R^{C1})₂, or —SR^{C1}, wherein each occurrence of R^{C1} is, independently, hydrogen, unsubstituted acyl, unsubstituted alkyl, unsubstituted alkenyl, unsubstituted alkynyl, unsubstituted carbocyclyl, unsubstituted heterocyclyl, unsubstituted aryl, unsubstituted heteroaryl, a nitrogen protecting group when attached to a nitrogen atom, an oxygen protecting group when attached to an oxygen atom, or a sulfur protecting group when attached to a sulfur atom, or two R^{C1} groups are joined to form an unsubstituted heterocyclic ring; or each R⁵, if present, is, independently, deuterium, halogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, —OR^{D1}, —N(R^{D1})₂, or —SR^{D1}, wherein each occurrence of R^{D1} is, independently, hydrogen, optionally substituted acyl, optionally substituted alkyl, optionally substituted alkenyl, optionally substituted alkynyl, optionally substituted carbocyclyl, optionally substituted heterocyclyl, optionally substituted aryl, or optionally substituted heteroaryl;

each R⁶, if present, is, independently, deuterium, halogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, =O, —CN, —OR^{C1}, —N(R^{C1})₂, or —SR^{C1}, wherein each occurrence of R^{C1} is, independently, hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, a nitrogen protecting group when attached to a nitrogen atom, an oxygen protecting group when attached to an oxygen atom, or a sulfur protecting group when attached to a sulfur atom, or two R^{C1} groups are joined to form an optionally substituted heterocyclic ring; or two R⁶ are taken together to form a first 5-7 membered optionally substituted, heterocyclyl or carbocyclyl ring fused to the ring to which the R⁶ are bound, wherein two substituents on the substituted heterocyclyl or carbocyclyl ring, or one substituent on the substituted heterocyclyl or carbocyclyl ring and a third R⁶ may be taken together with the atoms to which they are bound to form a second optionally substituted, heterocyclyl or carbocyclyl ring fused to the ring to the first optionally substituted, heterocyclyl or carbocyclyl ring and/or the ring to which the third R⁶ is bound;

each R⁷ is, independently, hydrogen or optionally substituted —C₁-C₆ alkyl;

n is 0, 1, 2, 3, 4, 5 or 6; and two R⁶ are taken together to form a first 5-7 membered unsubstituted, heterocyclyl or carbocyclyl ring fused to the ring to which the R⁶ are bound, wherein two substituents on the substituted heterocyclyl or carbocyclyl ring, or one substituent on the substituted heterocyclyl or carbocyclyl ring and a third R⁶ may be taken together with the atoms to which they are bound to form a second optionally substituted, heterocyclyl or carbocyclyl ring fused to the ring to the first optionally substituted, heterocyclyl or carbocyclyl ring and/or the ring to which the third R⁶ is bound; and each R⁷ is, independently, hydrogen or unsubstituted —C₁-C₆ alkyl.

3. The pharmaceutical composition of claim 2, wherein, ring A is

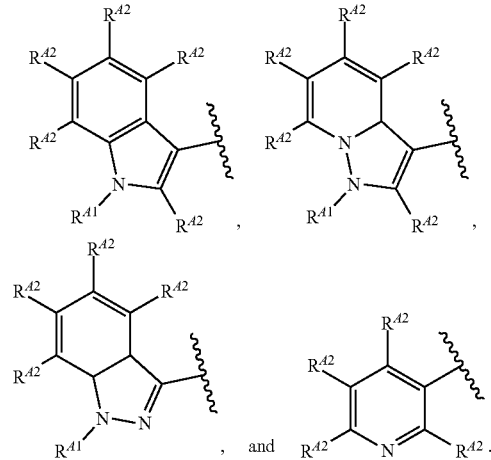

4. The pharmaceutical composition of claim 2, wherein ring A is

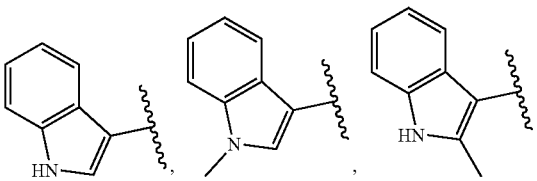

-continued

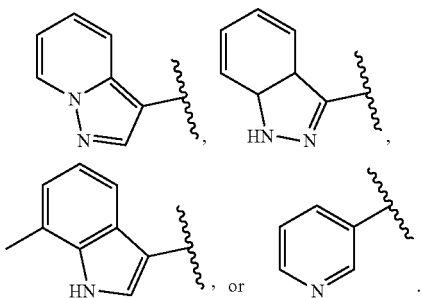, or

5. The pharmaceutical composition of claim 2, wherein ring A is; and/or each X is N; and/or W is C(R$^{1a}$).

6. The pharmaceutical composition of claim 5, wherein R$^{1a}$ is hydrogen, halo, —OH, —C$_1$-C$_3$ alkyl, —O—C$_1$-C$_3$ alkyl, —CN, —NH$_2$, —NH(C$_1$-C$_3$ alkyl), —N(C$_1$-C$_3$ alkyl)$_2$, or C$_3$-C$_6$ cycloalkyl.

7. The pharmaceutical composition of claim 6, wherein R$^{1a}$ is hydrogen, chloro, fluoro, —CN, or cyclopropyl.

8. The pharmaceutical composition of claim 2, wherein R$^{1b}$ is hydrogen.

9. The pharmaceutical composition of claim 8, wherein R$^2$ is —NH—; —N(C$_1$-C$_3$ alkyl)-; —NH—CH$_2$—*; or C$_1$-C$_2$ alkylene, wherein "*" represents a portion of R$^2$ bound to a cyclohexyl ring.

10. The pharmaceutical composition of claim 9, wherein R$^2$ is —NH—.

11. The pharmaceutical composition of claim 2, wherein R$^3$ is †—NH—C(O)—, †—C(O)—NH—, †—NH—S(O)$_2$—, or —N(CH$_3$)—CH$_2$—, wherein "†" represents a portion of R$^3$ bound to a cyclohexyl ring.

12. The pharmaceutical composition of claim 2, wherein R$^4$ is —NH$_2$.

13. The pharmaceutical composition of claim 2, wherein R$^5$ is absent or each R$^5$ is, independently, fluoro, chloro or morpholin-4-yl.

14. The pharmaceutical composition of claim 2, wherein each R$^6$ is, independently, —OH, fluoro, or methyl, or two or three R$^6$ are taken together with the carbon atoms in the cyclohexyl ring depicted in Formula I to form:

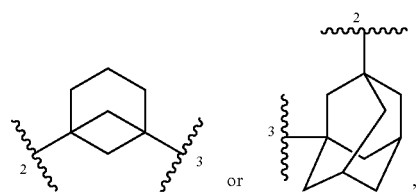 [SMILES: *C12CCCC(*)(C1)C2 ; *C12CC3CC(C1)CC(*)(C3)C2]

wherein "2" represents a portion of the ring bound to R$^2$, and "3" represents a portion of the ring bound to R$^3$.

15. The pharmaceutical composition of claim 2, wherein the compound or the pharmaceutically acceptable salt, isotopically labeled derivative, or stereoisomer thereof is of Formula (Ia):

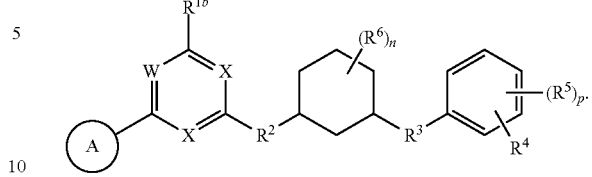

16. The pharmaceutical composition of claim 2, wherein the compound or the pharmaceutically acceptable salt, isotopically labeled derivative, or stereoisomer thereof is of Formula (Ib):

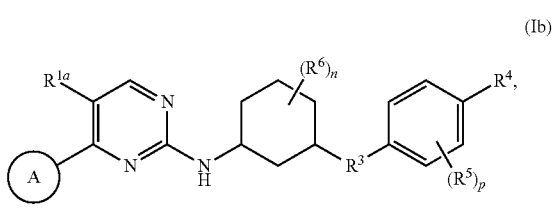

wherein:

ring A is

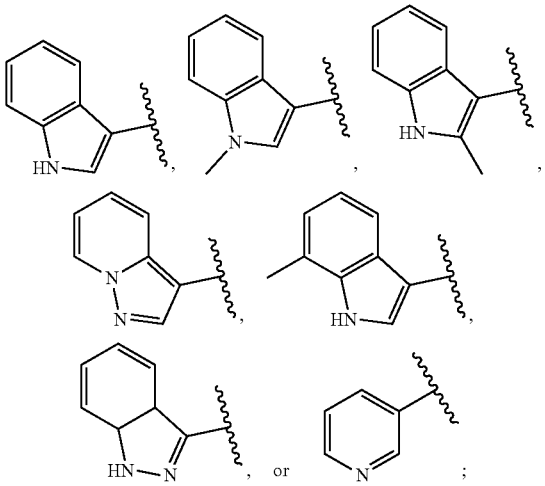

R$^{1a}$ is hydrogen, chloro, fluoro, —CN, or cyclopropyl;

R$^3$ is †—NH—C(O)—, †—C(O)—NH—, †—NH—S(O)$_2$—, or —N(CH$_3$)—CH$_2$—, wherein "t†" represents a portion of R$^3$ bound to a cyclohexyl ring;

R$^4$ is —NH$_2$, —NH—C(O)—(CH$_2$)$_3$—N(CH$_3$)$_2$, —NH—C(O)—CH$_2$—CH(OH)—CH$_2$—N(CH$_3$)$_2$, —NH—CH$_3$, or —NH—C(O)—C(O)—NH$_2$;

R$^5$ is absent, or each R$^5$ is, independently, fluoro, chloro, or morpholin-4-yl; and R$^6$ is absent, or each R$^6$ is, independently, —OH, halo, or C$_1$-C$_3$ alkyl; or two or three R$^6$ bound to separate carbon atoms are taken together with the carbon atoms to form:

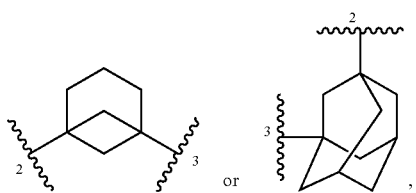 [SMILES: *C12CCCC(*)(C1)C2 ; *C12CC3CC(C1)CC(*)(C3)C2]

wherein "2" represents a portion of the ring bound to R², and "3" represents a portion of the ring bound to R³.

17. A method of treating a subject suffering from a disease or condition associated with aberrant activity of a cyclin-dependent kinase (CDK), wherein the disease or condition is cancer, a benign neoplasm, pathological angiogenesis, an inflammatory disease, an autoinflammatory disease, an autoimmune disease, or an infectious disease, and the method comprises the step of administering to the subject a therapeutically effective amount of the pharmaceutical composition of claim 2.

18. The method of claim 17, wherein the subject is suffering from a cancer associated with aberrant activity of cyclin-dependent kinase 7 (CDK7).

19. The method of claim 18, wherein the cancer is a breast cancer, brain cancer, Ewing's sarcoma, hematopoietic cancer, lung cancer, or ovarian cancer.

20. The method of claim 17, wherein the subject is a human.

21. A pharmaceutical composition comprising a pharmaceutically acceptable excipient and a therapeutically effective amount of a compound or a pharmaceutically acceptable salt, isotopically labelled derivative, or stereoisomer thereof, wherein the compound is Compound 100

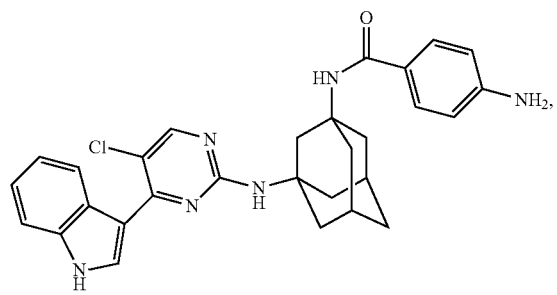

Compound 101

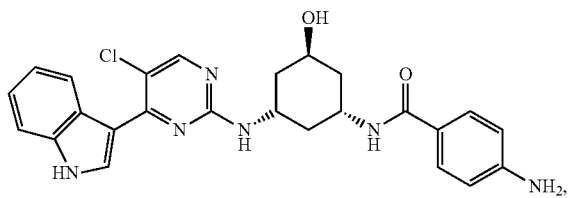

Compound 102

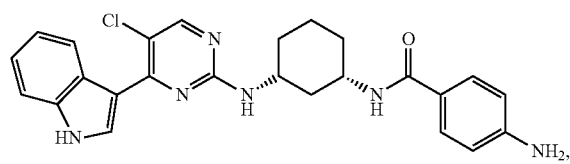

Compound 103

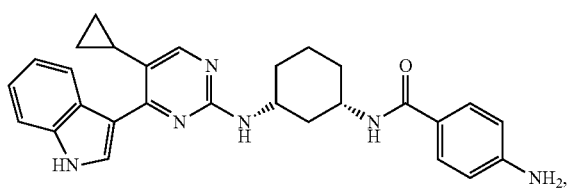

Compound 104

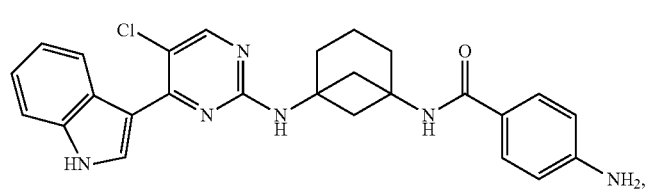

Compound 105

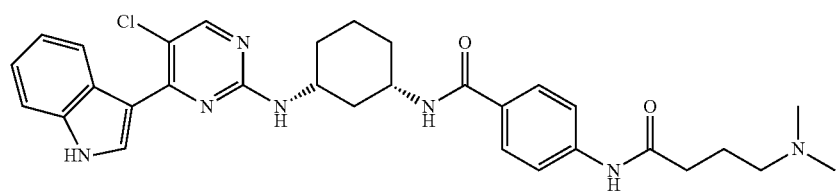

Compound 106

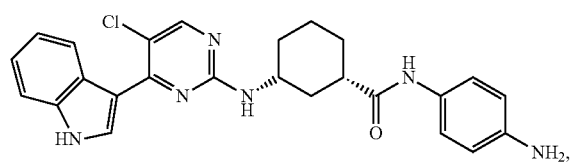

Compound 107

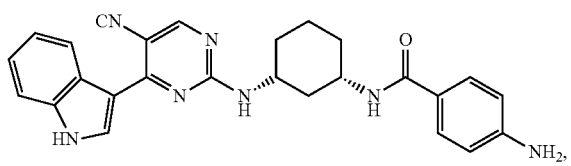

-continued
Compound 108
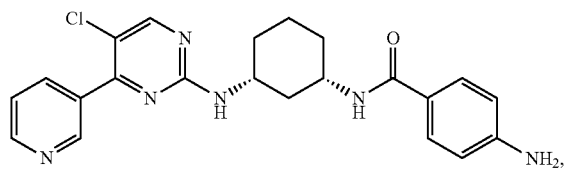
Compound 110
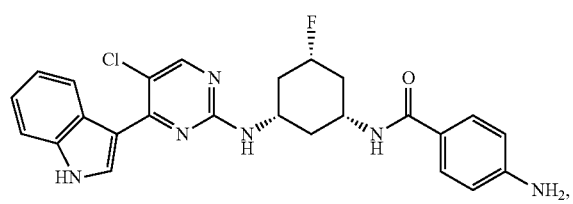
Compound 112
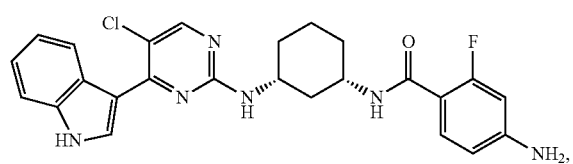
Compound 114
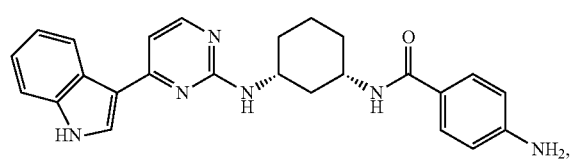
Compound 116
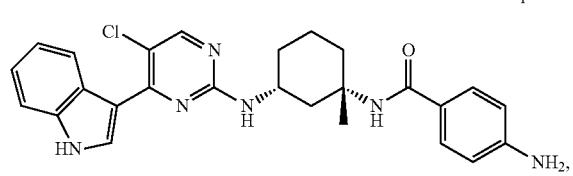
Compound 118
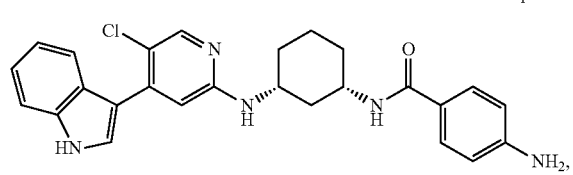
Compound 120
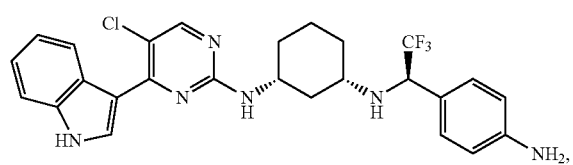
Compound 109
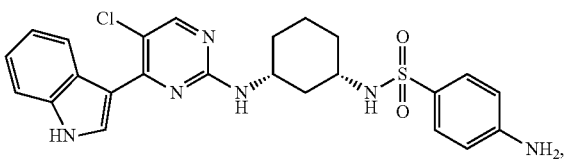
Compound 111
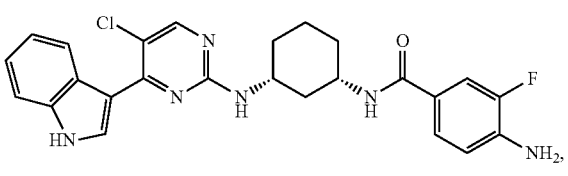
Compound 113
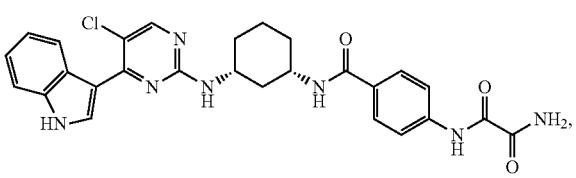
Compound 115
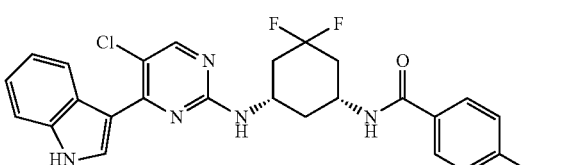
Compound 117
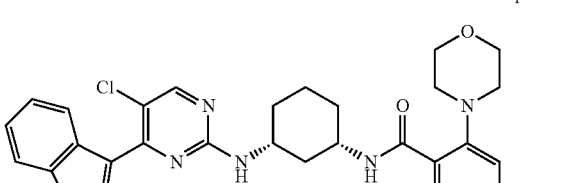
Compound 119
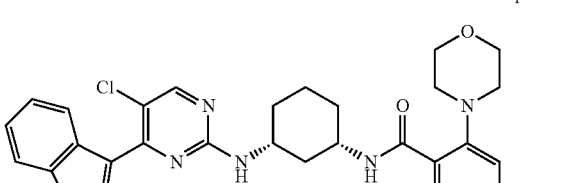
Compound 121
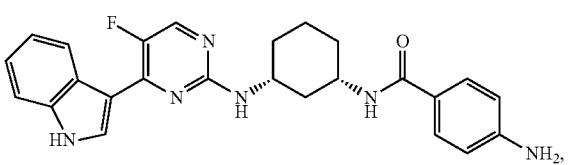

Compound 122
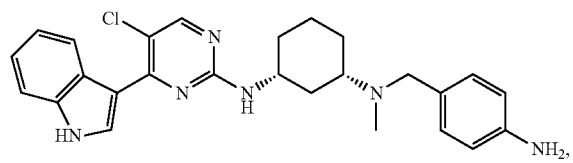
Compound 124
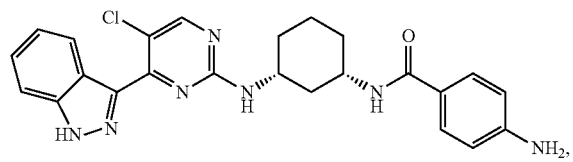
Compound 126
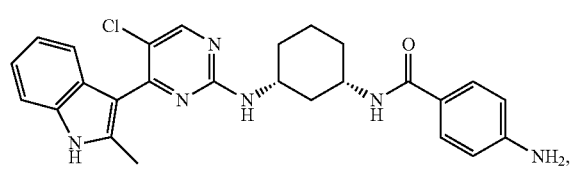
Compound 128
or
Compound 130
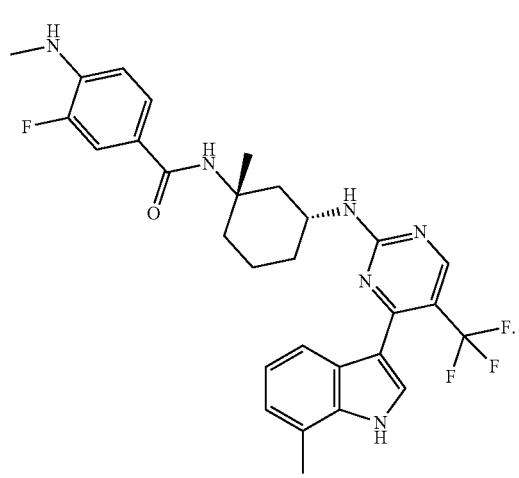
Compound 123
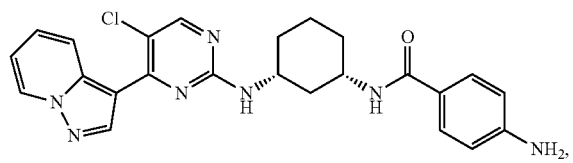
Compound 125
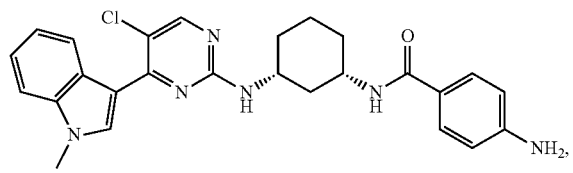
Compound 127
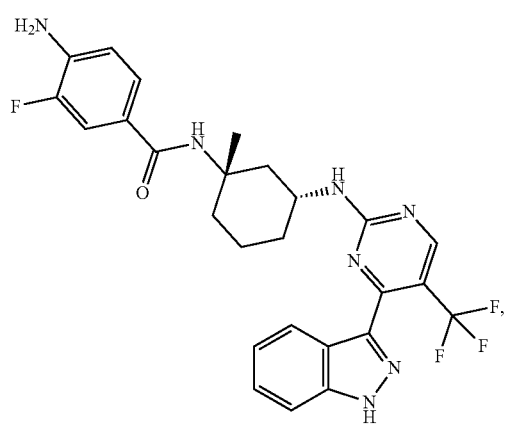
Compound 129
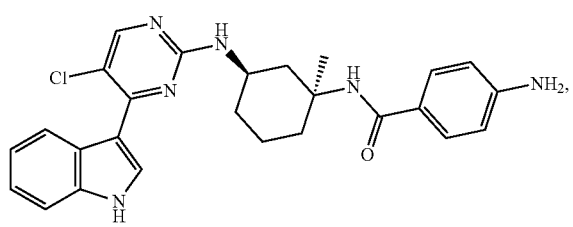

22. A method of treating a subject suffering from a disease or condition associated with aberrant activity of a CDK, wherein the disease or condition is cancer, a benign neoplasm, pathological angiogenesis, an inflammatory disease, an autoinflammatory disease, an autoimmune disease, or an infectious disease, and the method comprises the step of administering to the subject a therapeutically effective amount of the pharmaceutical composition of claim 21.

23. The method of claim 22, wherein the subject is suffering from a cancer associated with aberrant activity of CDK7.

24. The method of claim 23, wherein the cancer is a breast cancer, brain cancer, Ewing's sarcoma, hematopoietic cancer, lung cancer, or ovarian cancer.

25. The method of claim 22, wherein the subject is a human.

\* \* \* \* \*